US012357680B2

(12) United States Patent
Schüle et al.

(10) Patent No.: US 12,357,680 B2
(45) Date of Patent: Jul. 15, 2025

(54) INHIBITION OF HISTONE METHYL TRANSFERASES TO TREAT CANCER

(71) Applicant: Albert-Ludwigs-Universitat Freiburg, Freiburg (DE)

(72) Inventors: Roland Schüle, Weisweil (DE); Eric Metzger, Algolsheim (FR); Sheng Wang, Freiburg (DE); Manfred Jung, Gundelfingen (DE); Nicolas Barthes, Blodelsheim (FR); Bernhard Breit, Gundelfingen (DE); Daad Sarraf, Freiburg (DE); Tabea Pappert, Harxheim (DE)

(73) Assignee: Albert-Ludwigs-Universitat Freiburg, Freiburg (DE)

( * ) Notice: Subject to any disclaimer, the term of this patent is extended or adjusted under 35 U.S.C. 154(b) by 970 days.

(21) Appl. No.: 17/277,183

(22) PCT Filed: Sep. 18, 2019

(86) PCT No.: PCT/EP2019/075062
§ 371 (c)(1),
(2) Date: Mar. 17, 2021

(87) PCT Pub. No.: WO2020/058358
PCT Pub. Date: Mar. 26, 2020

(65) Prior Publication Data
US 2022/0184195 A1 Jun. 16, 2022

(30) Foreign Application Priority Data
Sep. 18, 2018 (EP) ..................................... 18195101

(51) Int. Cl.
*A61K 39/00* (2006.01)
*A61K 31/437* (2006.01)
*A61K 31/519* (2006.01)
*A61K 31/7076* (2006.01)
*A61K 31/7105* (2006.01)
*A61P 35/00* (2006.01)
*C07K 16/40* (2006.01)
*C12N 9/10* (2006.01)
*C12N 15/113* (2010.01)

(52) U.S. Cl.
CPC .... *A61K 39/001154* (2018.08); *A61K 31/437* (2013.01); *A61K 31/519* (2013.01); *A61K 31/7076* (2013.01); *A61K 31/7105* (2013.01); *A61P 35/00* (2018.01); *C07K 16/40* (2013.01); *C12N 9/1007* (2013.01); *C12N 15/1137* (2013.01); *A61K 2039/505* (2013.01); *C12N 2310/14* (2013.01)

(58) Field of Classification Search
None
See application file for complete search history.

(56) References Cited

FOREIGN PATENT DOCUMENTS

| CA | 3112958 A1 | 3/2020 |
|---|---|---|
| CN | 107815493 A | 3/2018 |
| EP | 1084705 B1 | 6/2014 |
| WO | WO 2021/053158 A1 | 3/2021 |
| WO | WO 2023/017152 A1 | 2/2023 |

OTHER PUBLICATIONS

Wang, et al. (2019) "KMT9 is an epigenetic writer that controls prostate cancer cell growth", Cancer Discovery, 9(7): 824. (Year: 2019).*
Wang, et al. (2024) "Structure-guided design of a selective inhibitor of methyltransferase KMT9 with cellular activity" Nature Communications, 15:43, 12 pages. (Year: 2024).*
Wang, et al. (2019) "KMT9 monomethylates histone H4 lysine 12 and controls proliferation of prostate cancer cells" Nature Structural & Molecular Biology, 26: 361-71. (Year: 2019).*
Ganesan, et al. (2011) "Rapid and Efficient Clearance of Blood-borne Virus by Liver Sinusoidal Endothelium", PLoS Pathogens, 7(9): e1002281, 11 pages. (Year: 2011).*
Randolph, et al. (2017) "The Lymphatic System: Integral Roles in Immunity", Annual Reviews of Immunology, 35: 31-52.*
Adams et al., "PHENIX: a comprehensive Python-based system for macromolecular structure solution." Acta Crystallogr. D. Biol. Crystallogr., vol. 66, pp. 213-221 (2010).
Afonine et al., "Towards automated crystallographic structure refinement with phenix.refine." Acta Crystallogr. D. Biol. Crystallogr., vol. 68, pp. 352-367 (2010).
Alabert et al., "Two distinct modes for propagation of histone PTMs across the cell cycle." Genes Dev., vol. 29, pp. 585-590 (2015).
Alsamraae, "Investigating aberrant signaling in enzalutamide-resistant prostate cancer." Newcastle University Thesis (260 Pages) (2017).
Arrowsmith et al., "Epigenetic protein families: a new frontier for drug discovery." Nat. Rev. Drug. Discov., vol. 11, pp. 384-400 (2012).
Battye et al., "iMOSFLM: a new graphical interface for diffraction-image processing with MOSFLM." Acta Crystallogr. D. Biol. Crystallogr., vol. 67, pp. 271-281 (2011).
Cai et al., "Synthesis and Assays of Inhibitors of Methyltransferases." Methods Enzymol., vol. 574, pp. 245-308 (2016).
Chakraborty et al., "Therapeutic miRNA and siRNA: Moving from Bench to Clinic as next generation medicine." Mol. Ther. Nucleic Acids, vol. 8, pp. 132-143 (2017).
Chen et al., "MolProbity: all atom structure validation for macromolecular crystallography." Acta Crystallogr. D. Biol. Crystallogr., vol. 66, pp. 12-21 (2010).
Cheng, "Structure and function of DNA methyltransferases." Annu. Rev. Biophys. Biomol. Struct., vol. 24, pp. 293-318 (1995).

(Continued)

*Primary Examiner* — Robert M Kelly
(74) *Attorney, Agent, or Firm* — Jenkins, Taylor & Hunt, P.A.

(57) ABSTRACT

The present invention is inter alia concerned with an inhibitor selected from the group consisting of a selective KMT9-inhibitor, a selective METTL21A-inhibitor and a selective METTL21B-inhibitor for use in the treatment of cancer. KMT9, METTL21A and METTL21B are characterized herein for the first time as histone methyl transferases, and inhibitors of the same can be used for treating cancer.

2 Claims, 31 Drawing Sheets
Specification includes a Sequence Listing.

(56) References Cited

OTHER PUBLICATIONS

Copeland et al., "Protein methyltransferases as a target class for drug discovery." Nature, vol. 8, pp. 724-732 (2009).
De Robertis et al., "The AOM/DSS murine model for the study of colon carcinogenesis: From pathways to diagnosis and therapy studies." J. Carcinog., vol. 10(9) (2011).
Devkota et al., "Analogues of the natural product sinefungin as inhibitors of EHMT1 and EHMT2." Acs Med. Chem. Lett., vol. 5, pp. 293-297 (2014).
Dillon et al., "The SET-domain protein superfamily: protein lysine methyltransferases." Genome Biol., vol. 6, p. 227 (2005).
Dobin et al., "STAR: ultrafast universal RNA-seq aligner." Bioinformatics, vol. 29, pp. 15-21 (2013).
Emsley et al., "Features and development of Coot." Acta Crystallogr. D. Biol. Crystallogr., vol. 66, pp. 486-501 (2010).
European Office Action Corresponding to European Patent Application No. 19768860.9-1111 dated May 4, 2022.
Evans et al., "How good are my data and what is the resolution?" Acta Crystallogr. D. Biol. Crystallogr., vol. 69, pp. 1204-1214 (2013).
Feller et al., "Global and specific responses of the histone acetylome to systematic perturbation." Mol. Cell., vol. 57, pp. 559-571 (2015).
Figaro et al., "HemK2 protein, encoded on human chromosome 21, methylates translation termination factor eRF1." FEBS Lett., vol. 582, pp. 2352-2356 (2008).
Fiskus et al., "Synergistic Pre-Clinical Activity of Combined Epigenetic Therapy with the Novel Histone Methyltransferase EZH2 Inhibitor 3-Deazaneplanocin and Histone Deacetylase Inhibitor Panobinostat against Human AML Cells." Blood, vol. 112(11), Article No. 3356 (2 pages) (2008).
Gross et al., "Enzymatic synthesis of S-adenosyl-L-methionine from L-methionine and ATP." Appl. Biochem. Biotechnol., vol. 8, pp. 415-422 (1983).
Heinz et al., "Simple combinations of lineage-determining transcription factors prime cis-regulatory elements required for macrophage and B cell identities." Molecular Cell., vol. 38, pp. 576-589 (2010).
Heurgue-Hamard et al., "The zinc finger protein Ynr046w is plurifunctional and a component of the eRF1 methyltransferase in yeast." J. Biol. Chem., vol. 281, pp. 36140-36148 (2006).
Hoefer et al., "Critical role of androgen receptor level in prostate cancer cell resistance to new generation antiandrogen enzalutamide." Oncotarget, vol. 7, pp. 59781-59794 (2016).
International Preliminary Report on Patentability Corresponding to International Application No. PCT/EP 2019/075062 dated Mar. 23, 2021.
International Search Report and the Written Opinion of the International Searching Authority Corresponding to International Application No. PCT/EP 2019/075062 dated Dec. 10, 2019.
Kusevic et al., "Substrate Specificity of the HEMK2 Protein Glutamine Methyltransferase and Identification of Novel Substrates." J. Biol. Chem., vol. 291, pp. 6124-6133 (2016).
Le Guen et al., "Functional analysis of the hemK gene product involvement in protoporphyrinogen oxidase activity in yeast." FEMS Microbiol. Lett., vol. 173, pp. 175-182 (1999).
LeRoy et al., "A quantitative atlas of histone modification signatures from human cancer cells." Epigenetics Chromatin., vol. 6, Article No. 20 (14 pages) (2013).
Liger et al., "Mechanism of activation of methyltransferases involved in translation by the Trm112 'hub' protein." Nucleic Acids Res., vol. 39, pp. 6249-6259 (2001).
Liu et al., "Deficiency in a glutamine-specific methyltransferase for release factor causes mouse embryonic lethality." Mol. Cell. Biol., vol. 30, pp. 4245-4253 (2010).
Liu et al., "Histone lysine methyltransferases as anti-cancer targets for drug discovery." Acta Pharm. Sinica, vol. 37, pp. 1273-1280 (2016).
McCoy et al., "Phaser crystallographic software." J. Appl. Crystallogr., vol. 40, pp. 658-674 (2007).

Metzger et al., "Assembly of methylated KDM1A and CHD1 drives androgen receptor-dependent transcription and translocation." Nat. Struc. Mol. Biol., vol. 23, pp. 132-139 (2016).
Metzger et al., "KMT9 monomethylates histone H4 lysine 12 and controls proliferation of prostate cancer cells." Nat. Stru. Mol. Biol., vol. 26, pp. 361-371 (2019).
Metzger et al., "LSD1 demethylates repressive histone marks to promote androgen-receptor-dependent transcription." Nature, vol. 437, pp. 436-439 (2005).
Morera et al., "Targeting histone methyltransferases and demethylases in clinical trials for cancer therapy." Clinical Epigenetics, vol. 8(57) (2016).
Nadal et al., "The evolving role of enzalutamide on the treatment of prostate cancer." Future Oncol., vol. 12, pp. 607-616 (2016).
Ong et al., Identifying and quantifying in vivo methylation sites by heavy methyl SILAC. Nat. Methods, vol. 1 (8 pages) (2004).
Petrossian et al., "Uncovering the human methyltransferasome." Mol. Cell Proteomics, vol. 10, DOI 10.1074/mcp.M110.000976 (2011).
Ratel et al., "Undetectable levels of N6-methyl adenine in mouse DNA: Cloning and analysis of PRED28, a gene coding for a putative mammalian DNA adenine methyltransferase." FEBS Lett., vol. 580, pp. 3179-3184 (2006).
Robinson et al., "Small-sample estimation of negative binomial dispersion, with applications to SAGE data." Biostatistics, vol. 9, pp. 321-332 (2008).
Ruggero et al., "Epigenetic regulation in prostate cancer progression." Curr. Mol. Biol. Rep., vol. 4, pp. 101-115 (2018).
Schiffers et al., "Quantitative LC-MS Provides No Evidence for m(6)dA or m(4)dC in the Genome of Mouse Embryonic Stem Cells and Tissues." Angew. Chem. Int. Ed. Engl., vol. 56, pp. 11268-11271 (2017).
Schmid-Burgk et al., "OutKnocker: a web tool for rapid and simple genotyping of designer nuclease edited cell lines." Genome Res., vol. 24, pp. 1719-1723 (2014).
Schmidt et al., "Synthesis of an arrayed sgRNA library targeting the human genome." Sci. Rep., vol. 5, p. 14987 (2015).
Schubert et al., "Many paths to methyltransfer: a chronicle of convergence." Trends Biochem. Sci., vol. 28, pp. 329-335 (2003).
Schubert et al., "Structures along the catalytic pathway of PrmC/HemK, an N5-glutamine AdoMet-dependent methyltransferase." Biochemistry, vol. 42, pp. 5592-5599 (2003).
Schule, "The novel histone methyltransferase KMT9 writes the histone mark H4K12 and controls metabolism and proliferation of castration-resistant prostate cancer." Ulm University, International Graduate School in Molecular Medicine Ulm, Spring Meeting, Wed., Apr. 11, 2018.
Stein et al., "The DOT1L inhibitor pinometostat reduces H3K79 methylation and has modest clinical activity in adult acute leukemia." Blood, vol. 131(24), pp. 2661-2669 (2018).
Strahl et al., "The language of covalent histone modifications." Nature, vol. 403, pp. 41-45 (2000).
Thorvaldsdottir et al., "Integrative Genomics Viewer (IGV): high-performance genomics data visualization and exploration." Brief Bioinform., vol. 14, pp. 178-192 (2012).
Uchiyama et al., "Aristeromycin and DZNeP cause growth inhibition of prostate cancer via induction of mir-26a." Eur. J. Pharmacol., vol. 812, pp. 138-146 (2017).
Van de Wetering et al., "Prospective derivation of a living organoid biobank of colorectal cancer patients." Cell, vol. 161, pp. 933-945 (2015).
Van Leeuwen et al., "Dot1p modulates silencing in yeast by methylation of the nucleosome core." Cell, vol. 109, pp. 745-756 (2002).
Vooijs et al., "A highly efficient ligan-regulated Cre recombinase mouse line shows that LoxP recombination is position dependent." EMBO Rep., vol. 2(4), pp. 292-297 (2001).
Waddington et al., "A broad overview and review of CRISPR-Cas technology and stem cells." Curr. Stem Cell Rep., vol. 2, pp. 9-20 (2016).
Xiao et al., "N(6)-Methyladenine DNA Modification in the Human Genome." Mol. Cell., (2018).

(56) References Cited

OTHER PUBLICATIONS

Yang et al., "Structural characterization and comparative phylogenetic analysis of *Escherichia coli* HemK, a protein (N5)-glutamine methyltransferase." J. Mol. Biol., vol. 340, pp. 695-706 (2004).

Zagni et al., "Histone methyltransferase inhibitors: novel epigenetic agents for cancer treatment." Curr. Med. Chem., vol. 20, pp. 167-185 (2013).

Zhang et al., "Model-based analysis of ChIP-Seq (MACS)." Genome Biol., vol. 9, Article No. R137 (9 pages) (2008).

Zorbas et al., "The human 18S rRNA base methyltransferases DIMT1L and WBSCR22-TRMT112 but not rRNA modification are required for ribosome biogenesis." Mol. Biol. Cell., vol. 26, pp. 2080-2095 (2015).

Bacher, J.A., et al., "Assay Development and Inhibitor Optimization for the Histone Lysine Methyltransferase KMT," PhD Thesis, University of Freiburg., pp. 196 (2020).

Letoquart, J., et al., "Insights into molecular plasticity in protein complexes from Trm9-Trm112 (RNA modifying enzyme crystal structure," NAR, vol. 43, No. 22, pp. 10989-11002, 2015.

Letoquart, J., et al., "Structural and functional studies of Bud23-Trm112 reveal 18S rRNA N7-G1575 methylation occurs on late 40S precursor ribosomes," PNAS, vol. 111, No. 51, e5518-e5526, 2014.

Mori, S., et al., "Development of novel bisubstrate-type inhibitors of histone methyltransferase SET7/9," Bioorganic & Medicinal Chemistry, vol. 18, pp. 8158-8166 (2010).

Office Action (Annex to the communication) corresponding to European Patent Application No. 19768860.9 dated Feb. 7, 2024, 10 pages.

Office Action (Annex to the communication) corresponding to European Patent Application No. 19768860.9 dated Jan. 15, 2024, 27 pages.

Office Action (Annex to the communication) corresponding to European Patent Application No. 19768860.9 dated May 8, 2023, 9 pages.

Office Action (Decision to Refusal) corresponding to European Patent Application No. 19768860.9 dated Feb. 12, 2024, 26 pages.

Watson, V.G., et al., "Abstract 3878: A highly sensitive assay for the discovery of inhibitors of the histone methyltransferase DOT1L to treat MLL-rearranged leukemia," Cancer Research, vol. 72, Issue 8_Supplement: 3878, pp. 9, Apr. 15, 2012.

Woodcock, C.B., et al., "Human HemK2/KMT9/N6AMT1 is an active protein methyltransferase, but does not act on DNA in vitro, in the presence of Trm112," Cell Discovery, vol. 5, No. 50, pp. 3, 2019.

\* cited by examiner

Figure 1
A
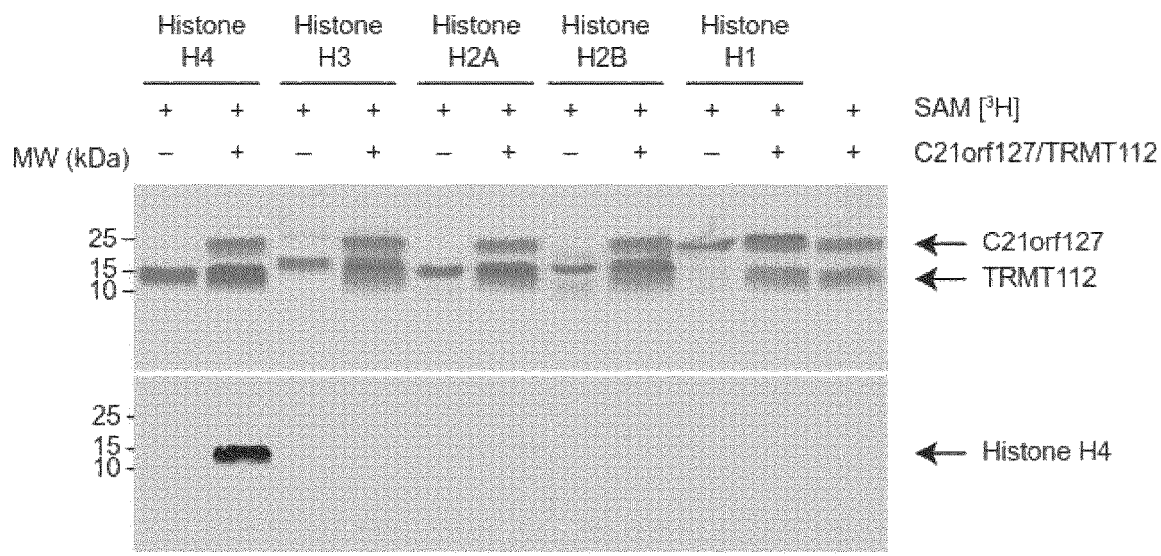
B
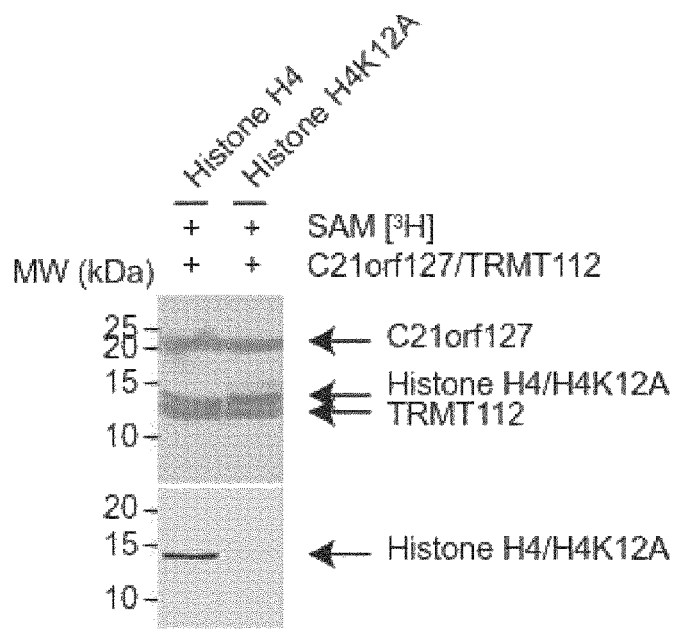

Figure 1 - continued
C
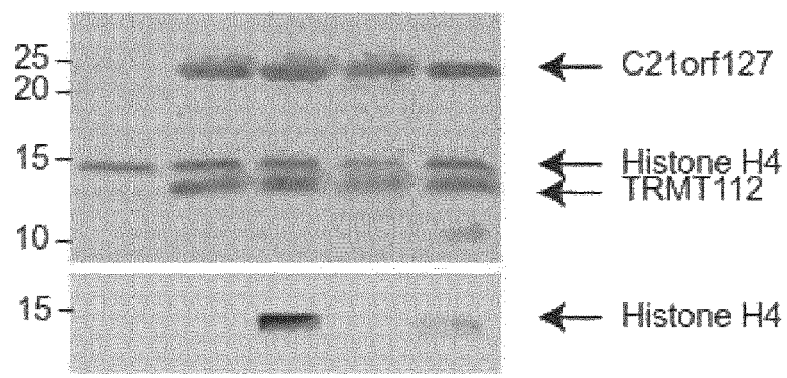
D
Histone H4 / C21orf127 / TRMT112 / SAH co-crystal structure
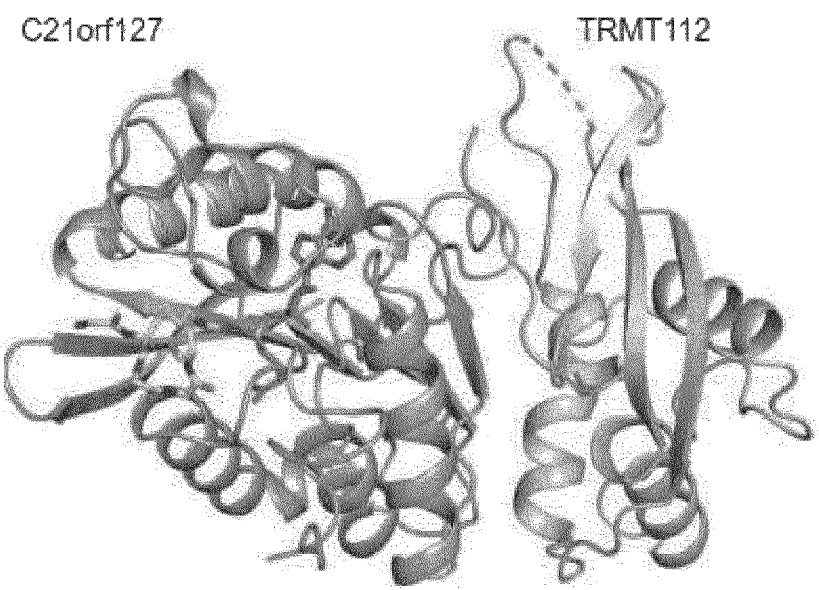

Figure 2 – continued
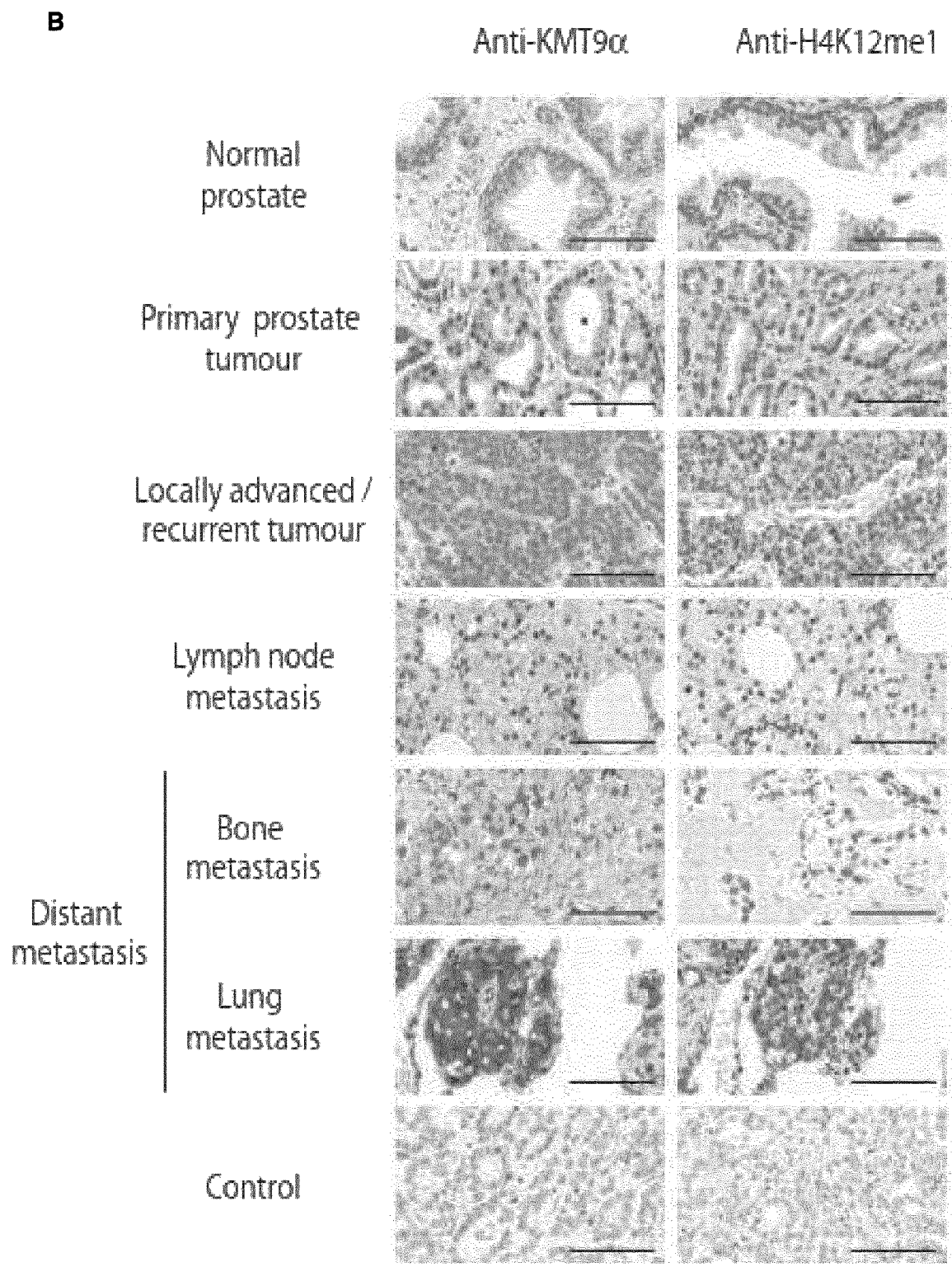

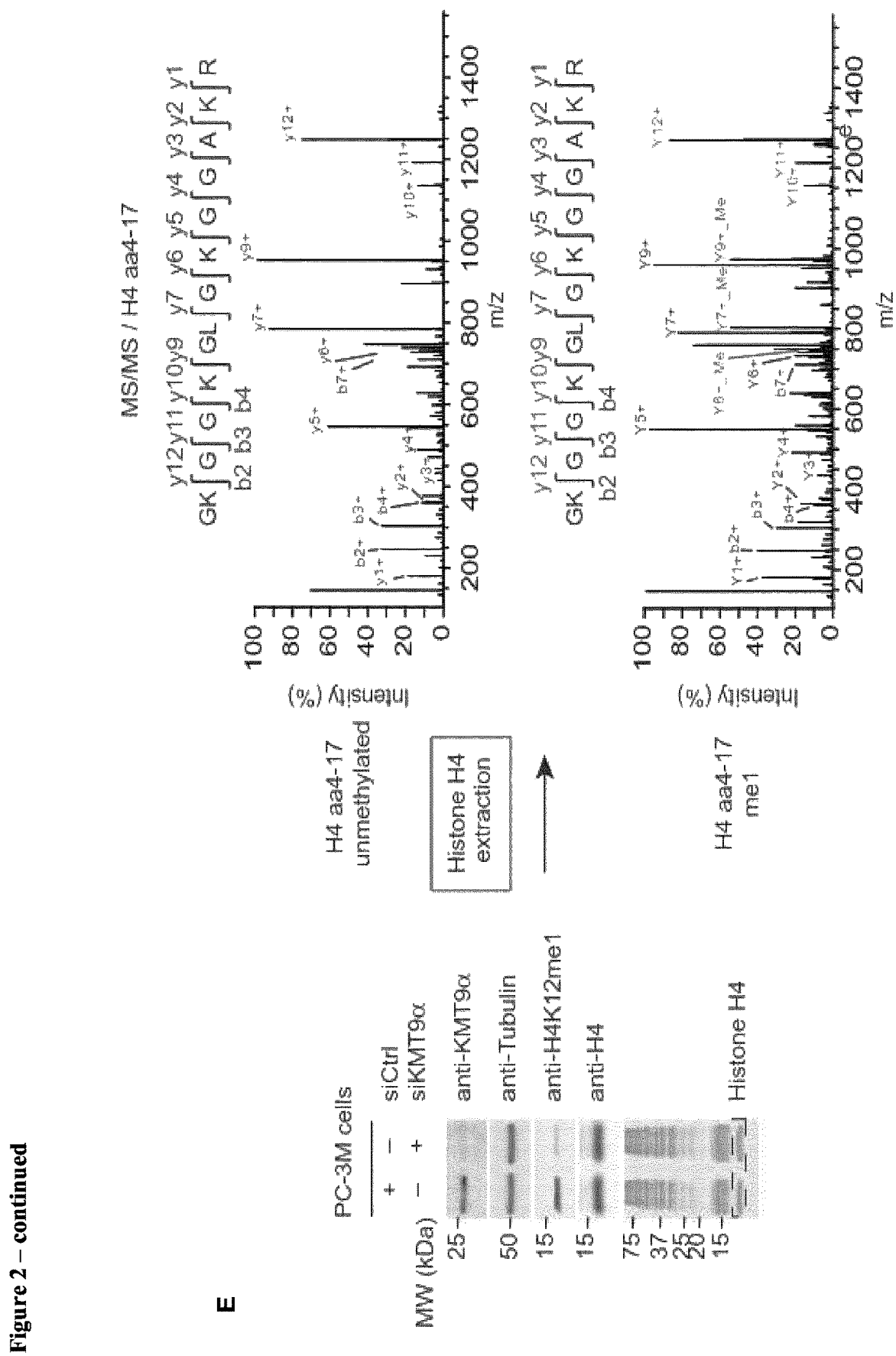
Figure 2 – continued

Figure 2 – continued
E - cont.
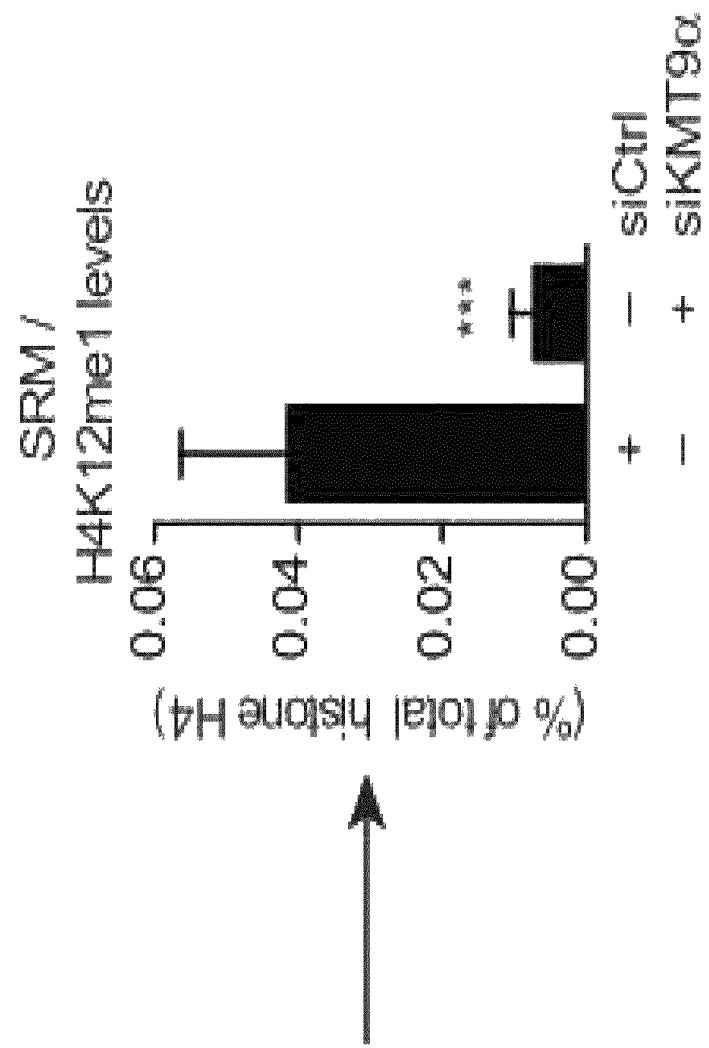

Figure 3
A
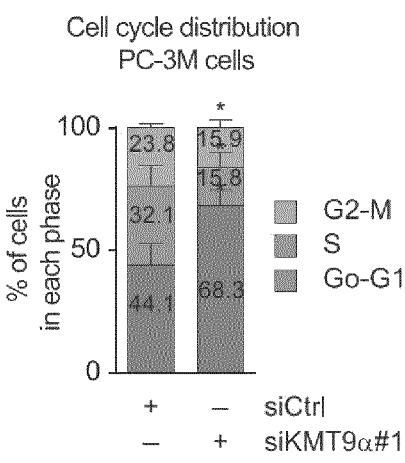
B
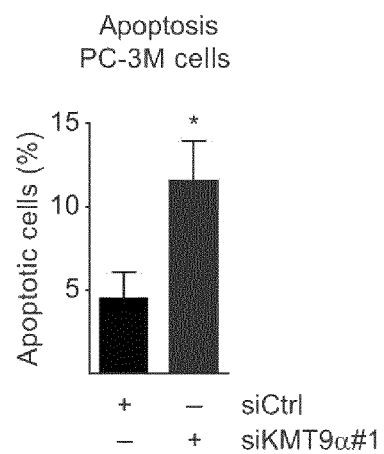
C
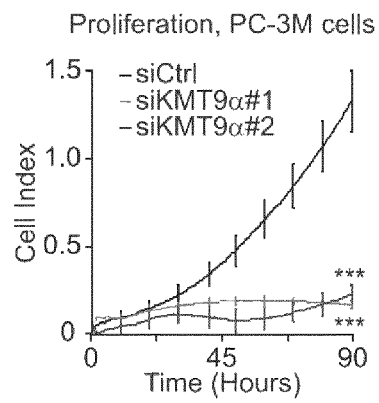
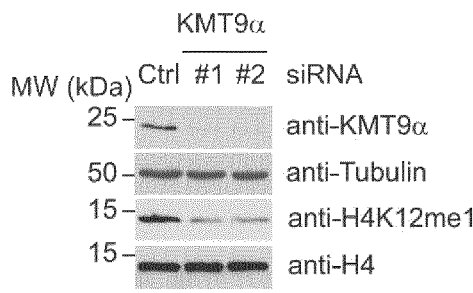
D
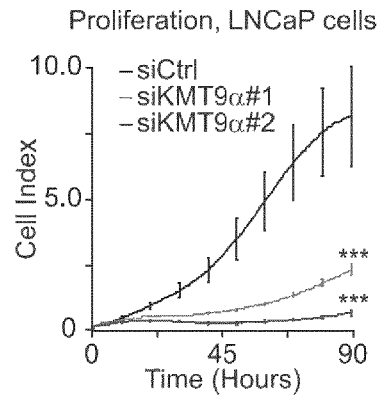
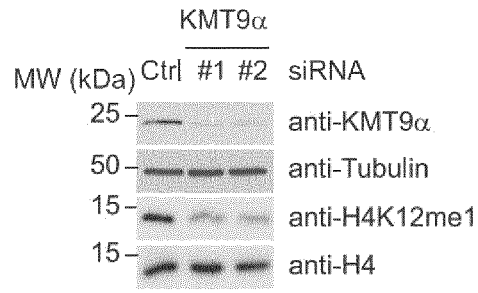

Figure 3- continued
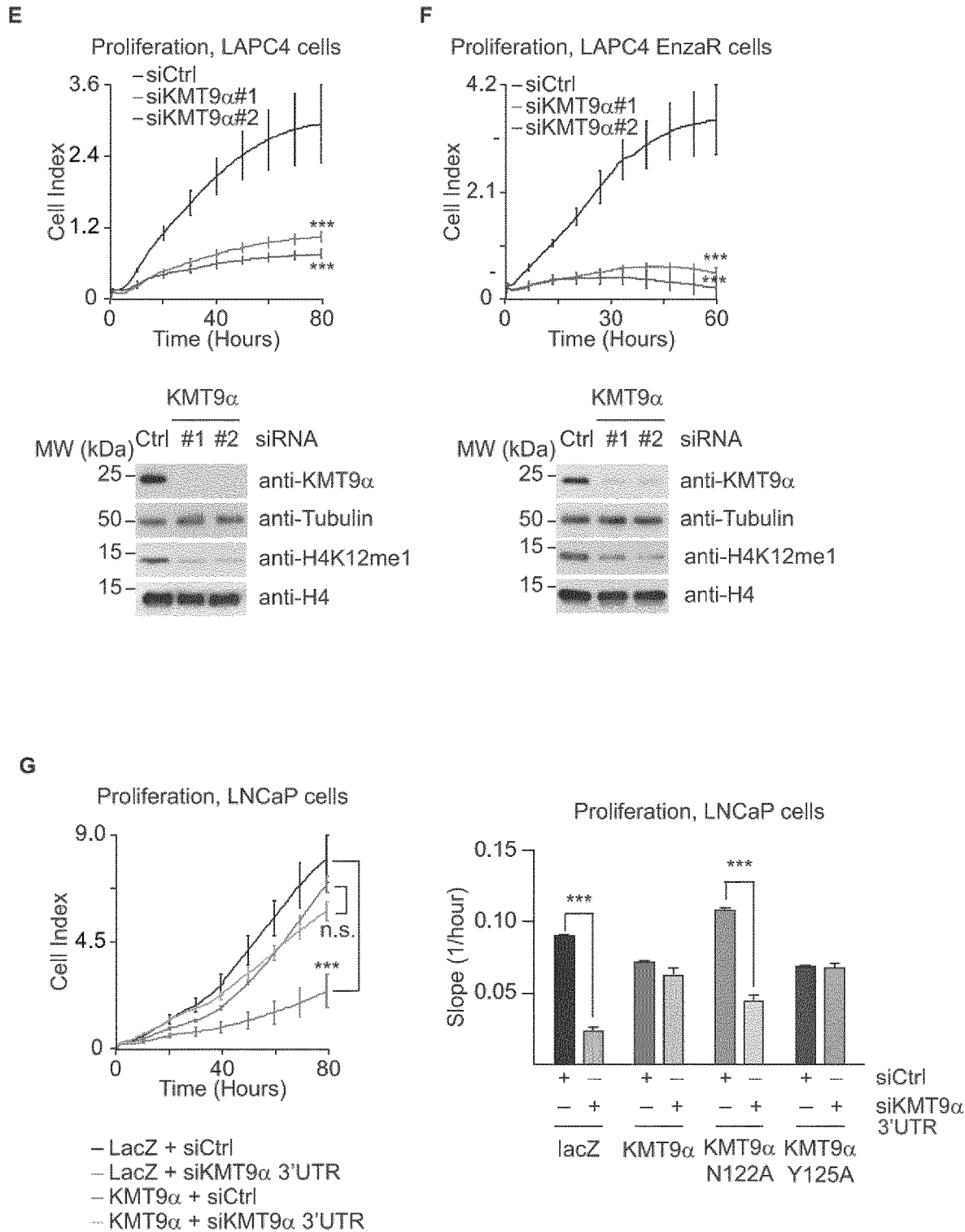

Figure 3- continued
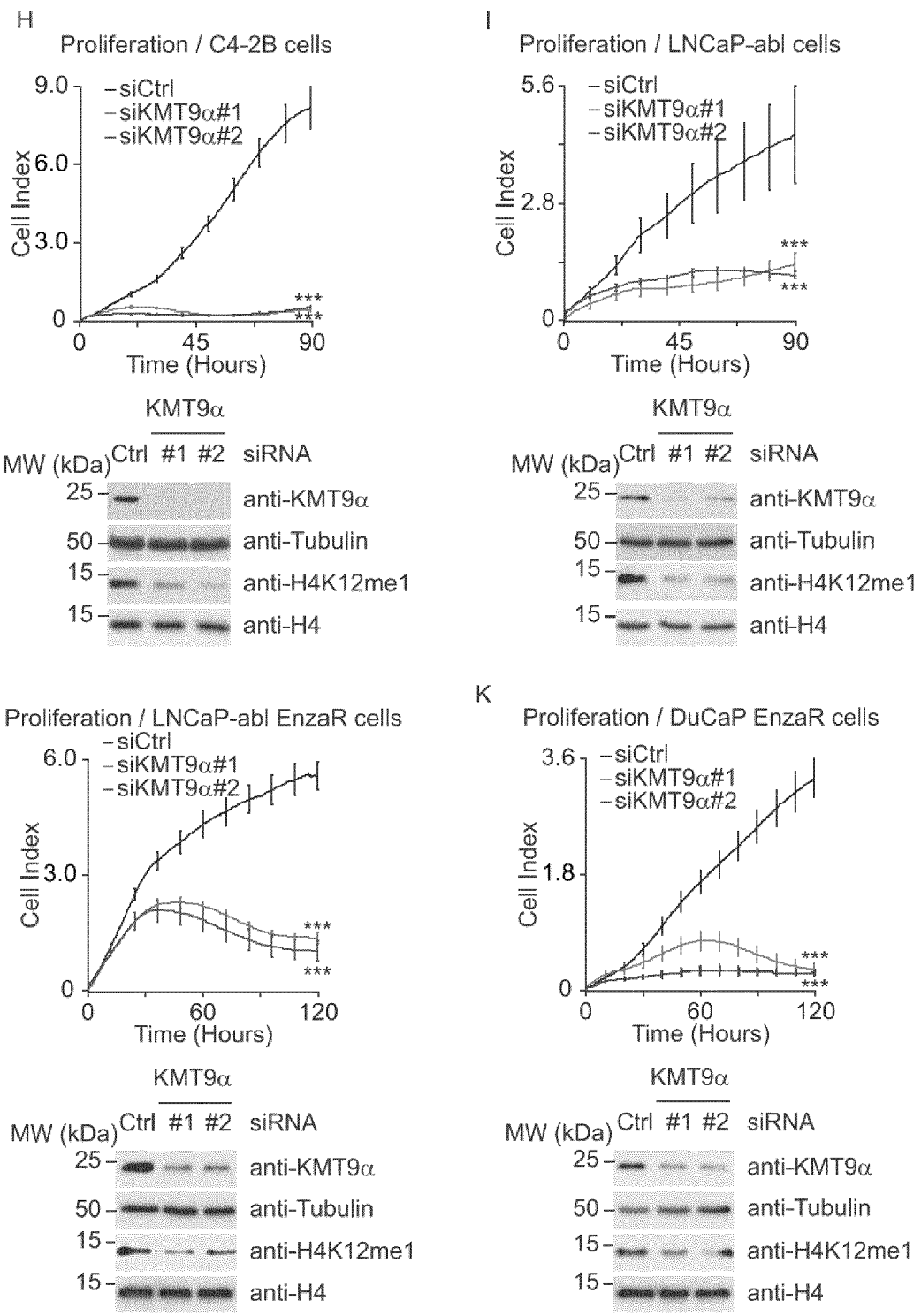

Figure 3- continued
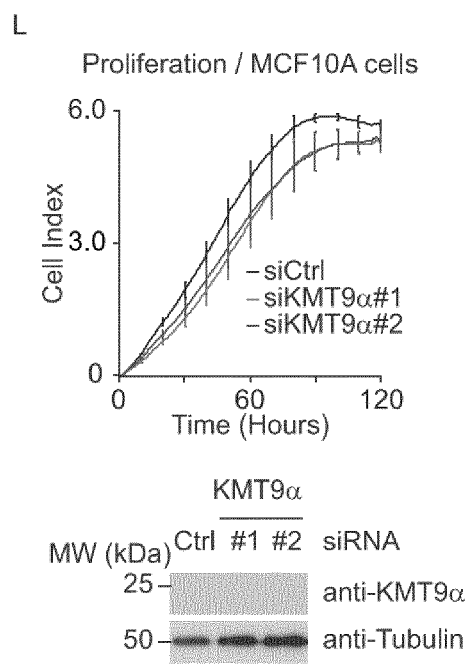

Figure 4 – continued
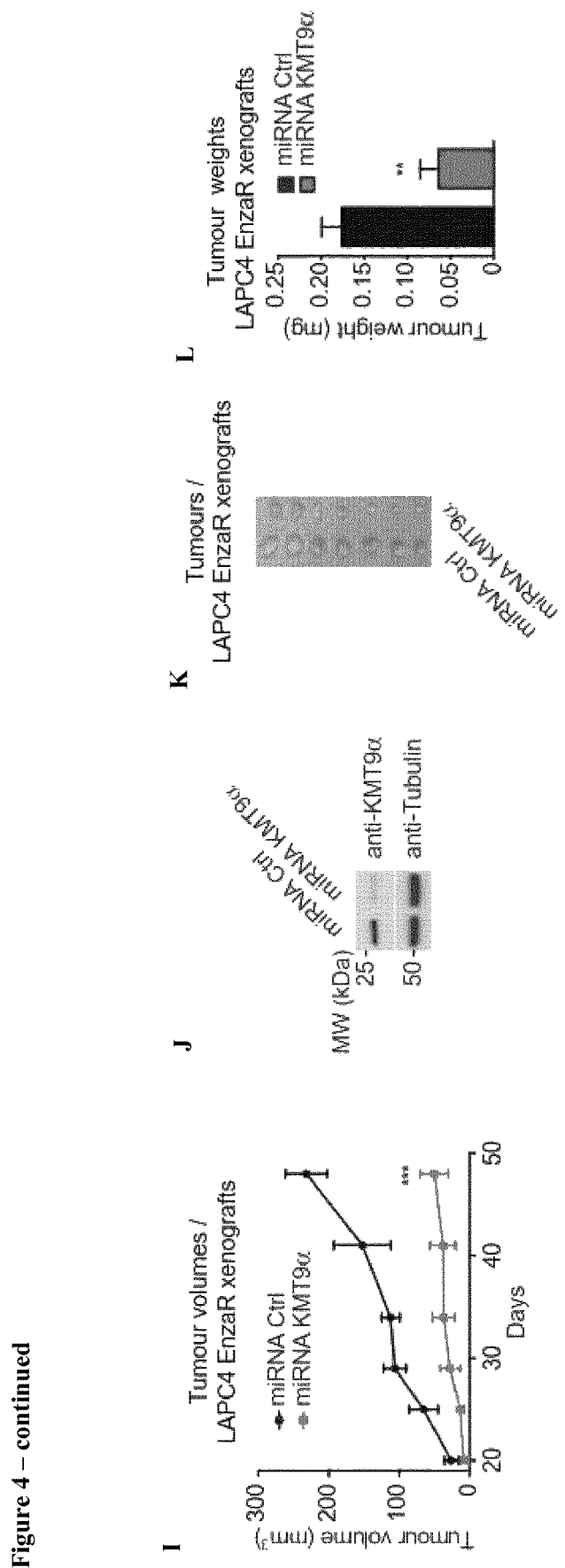

Figure 5
A
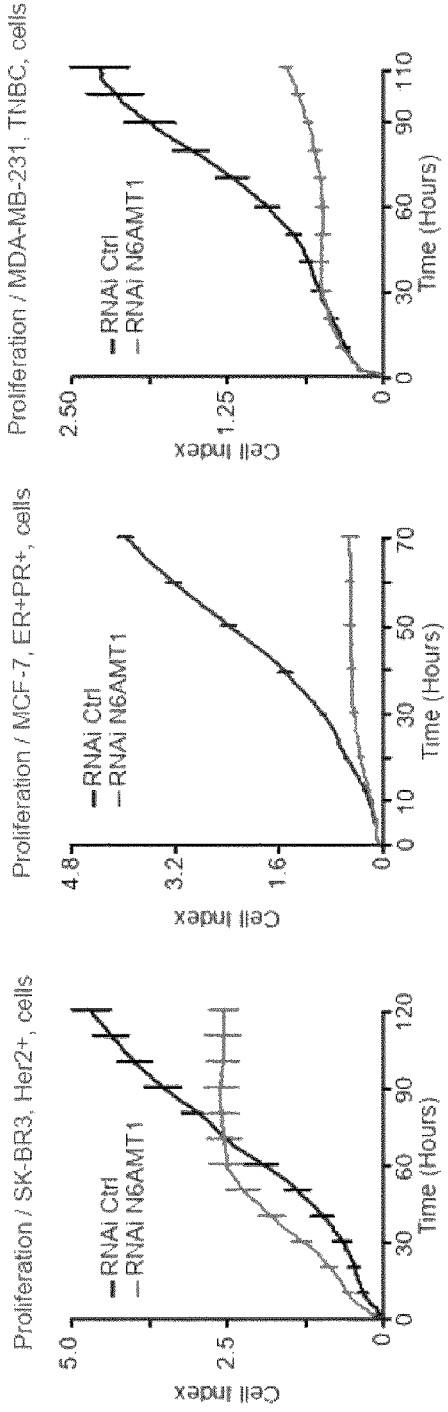
B
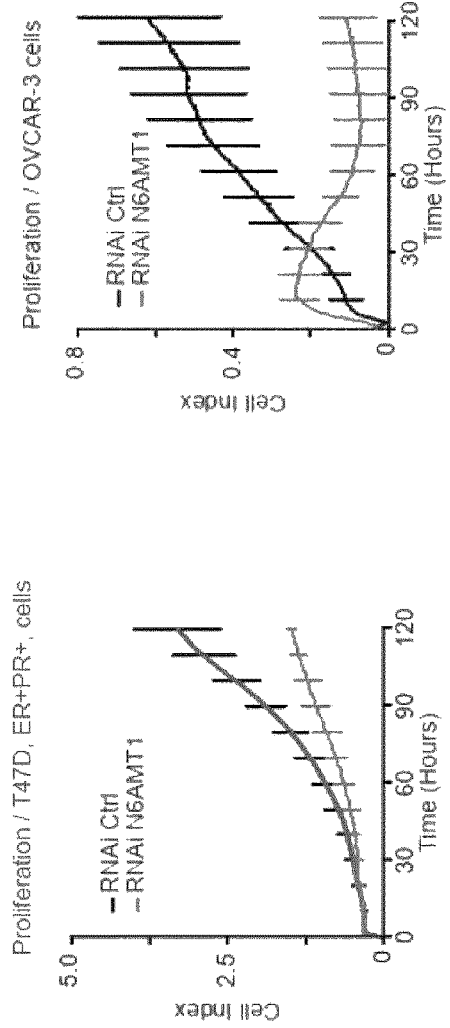

Continue Figure 5
Colon cancer cells
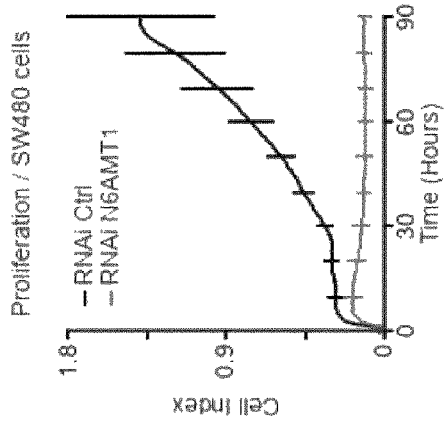
Glioblastoma cells
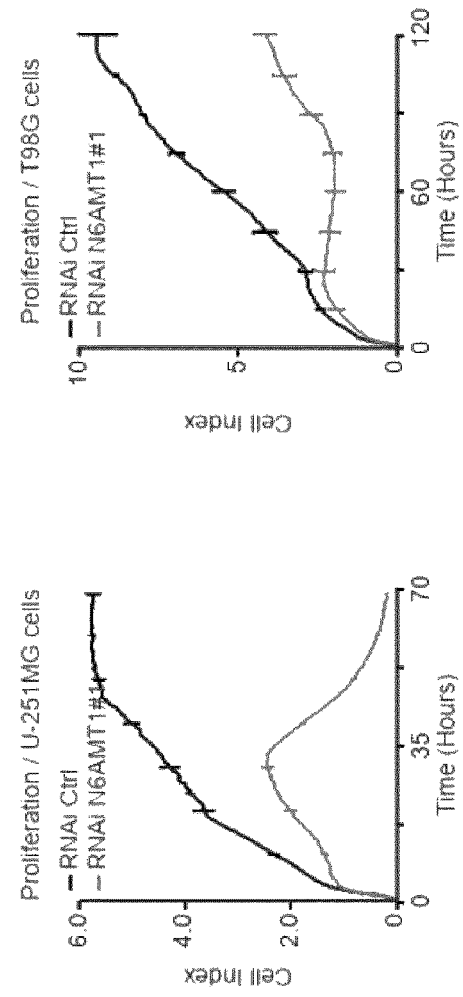

A

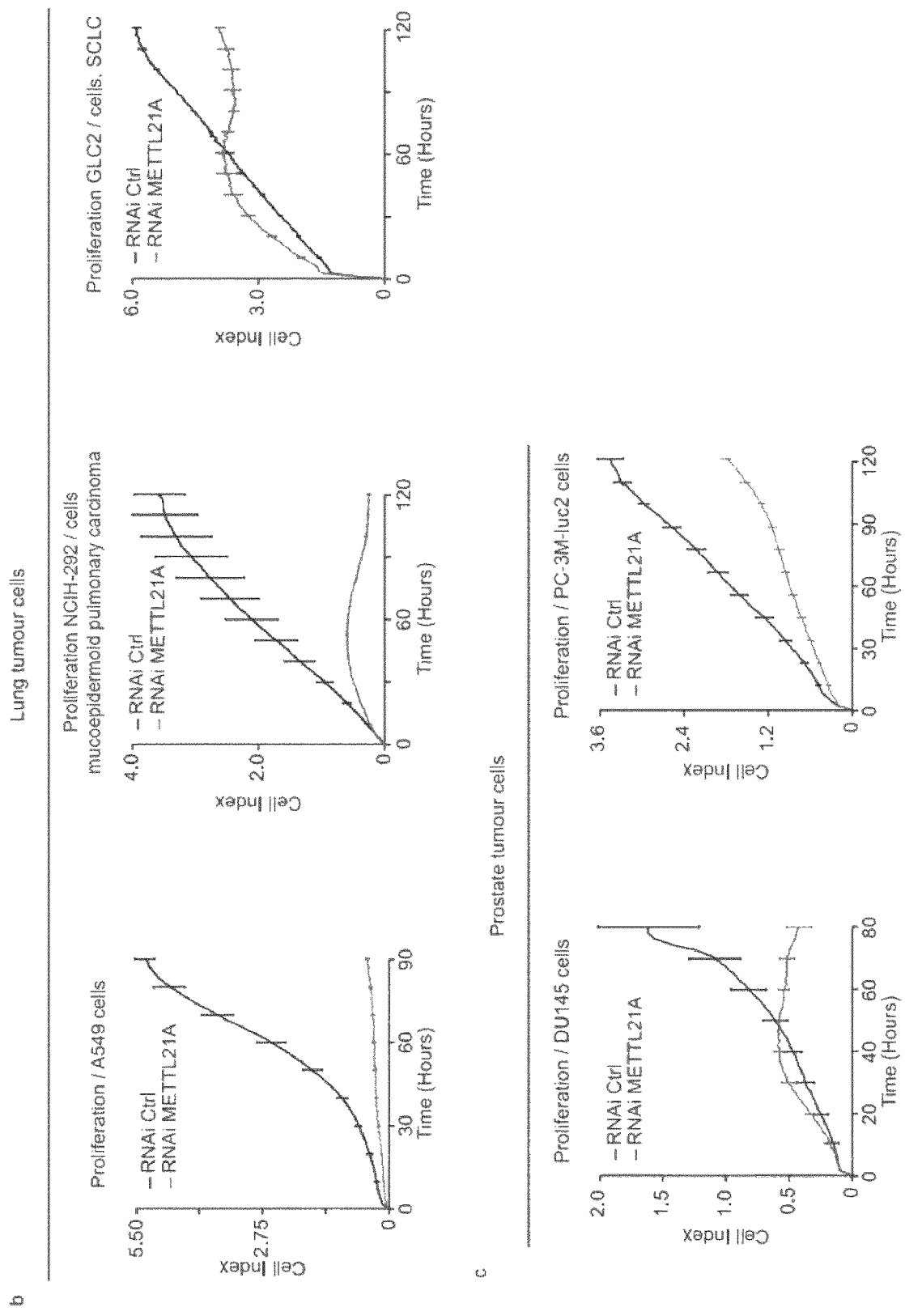
Figure 7 - continued

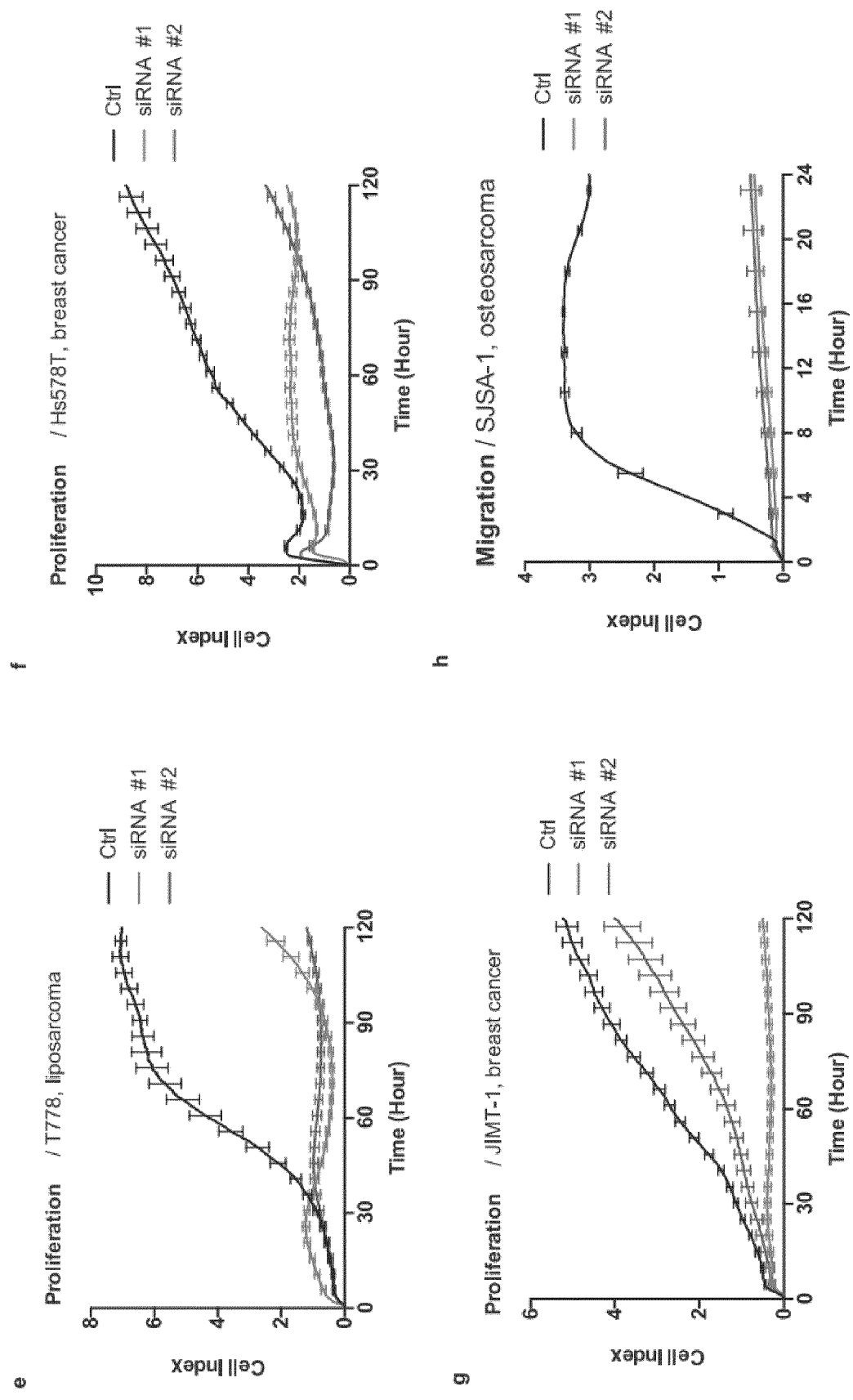

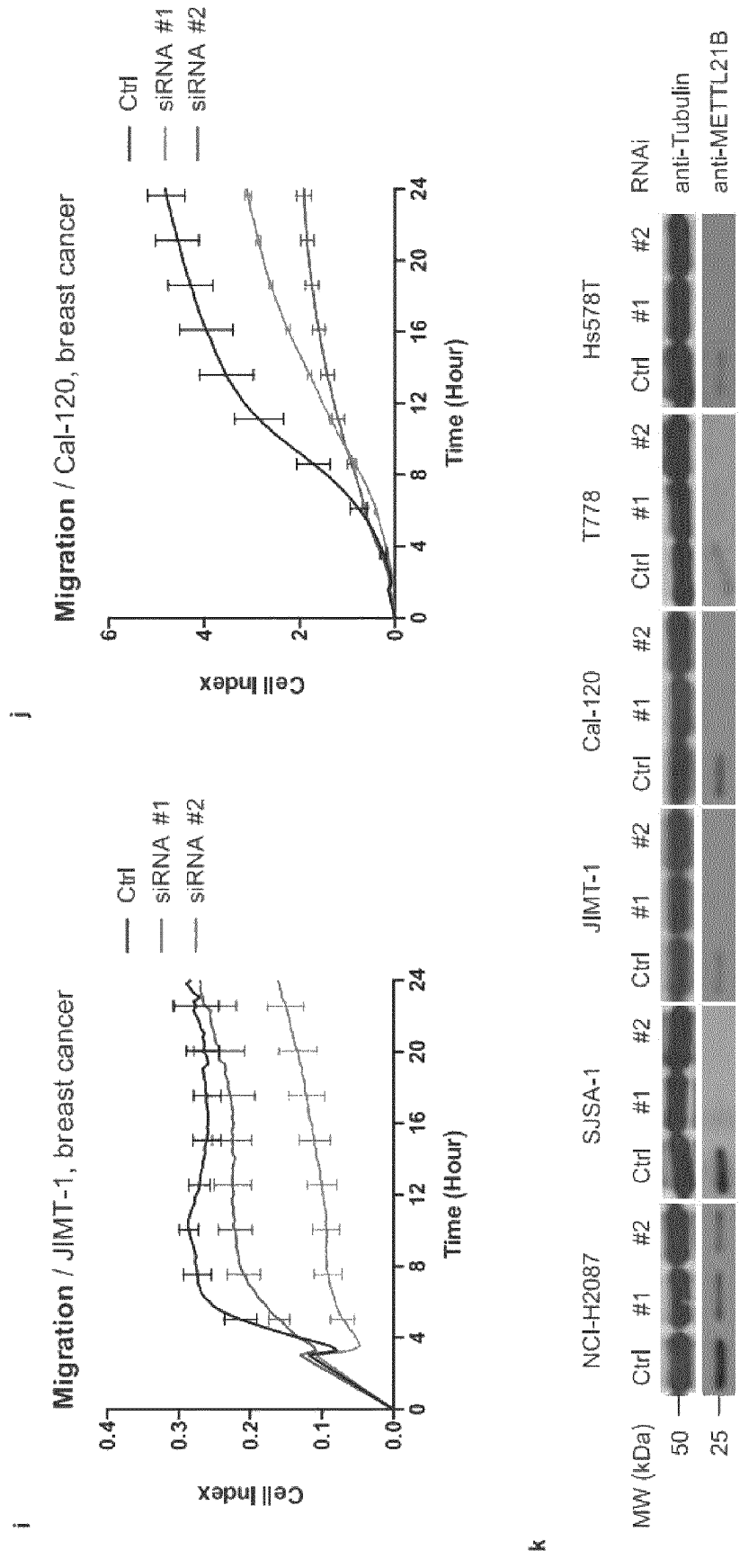
Figure 8- continued

Figure 10
A
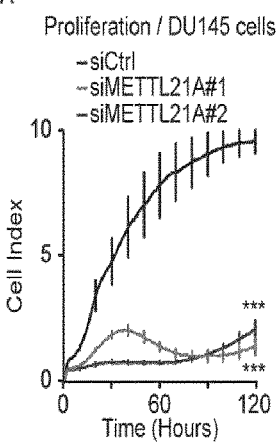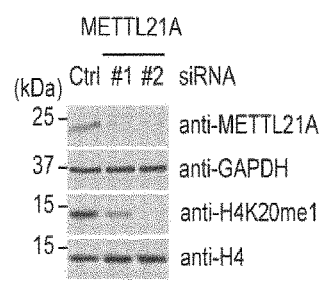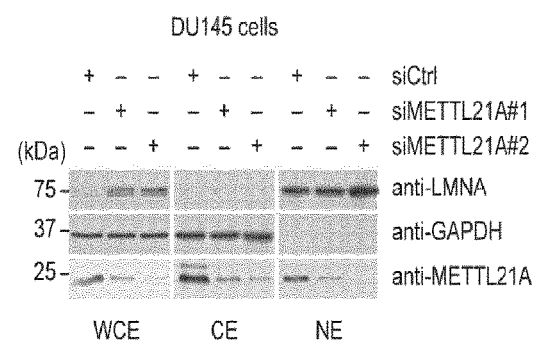
B
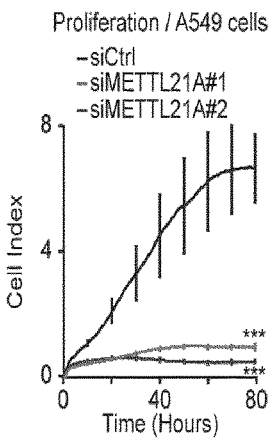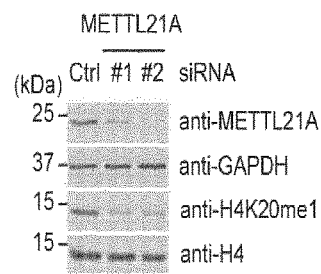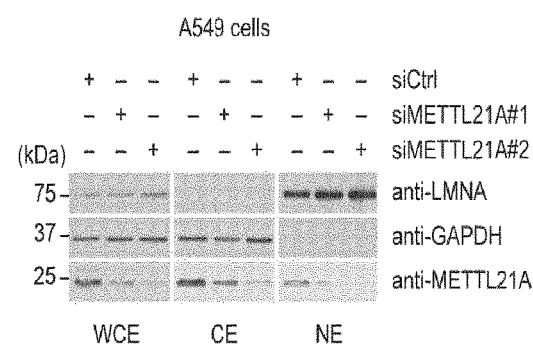

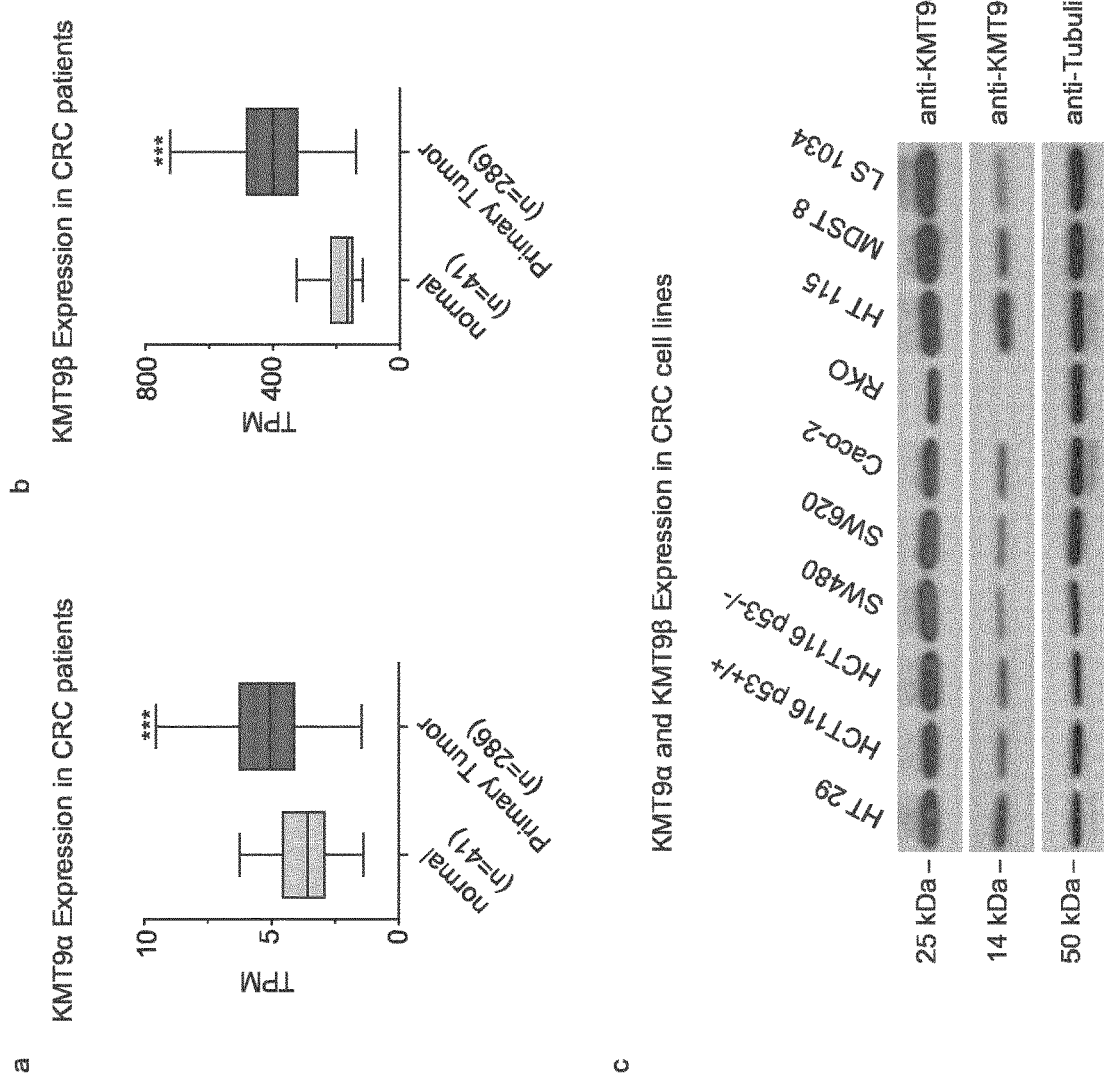

Figure 11- continued
d
Subcellular localization of KMT9α in human CRC cell lines
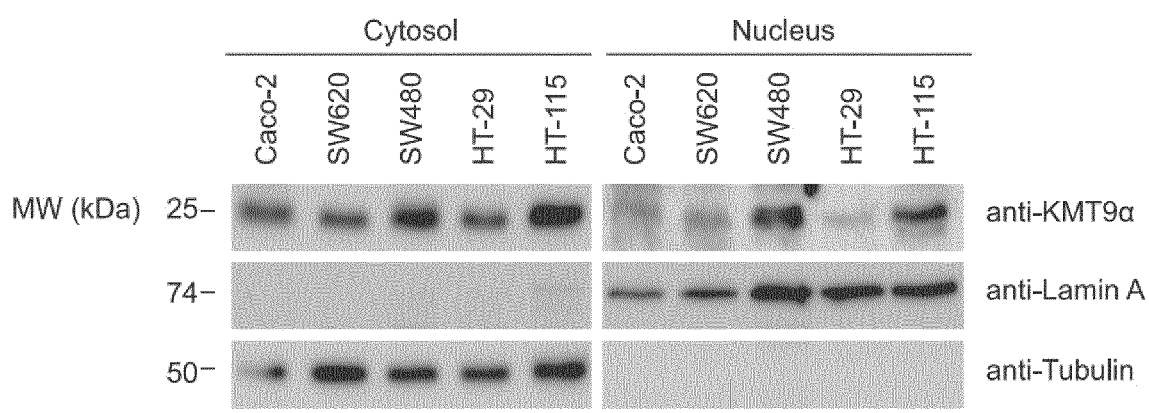
e
Subcellular localization of KMT9α in human CRC samples
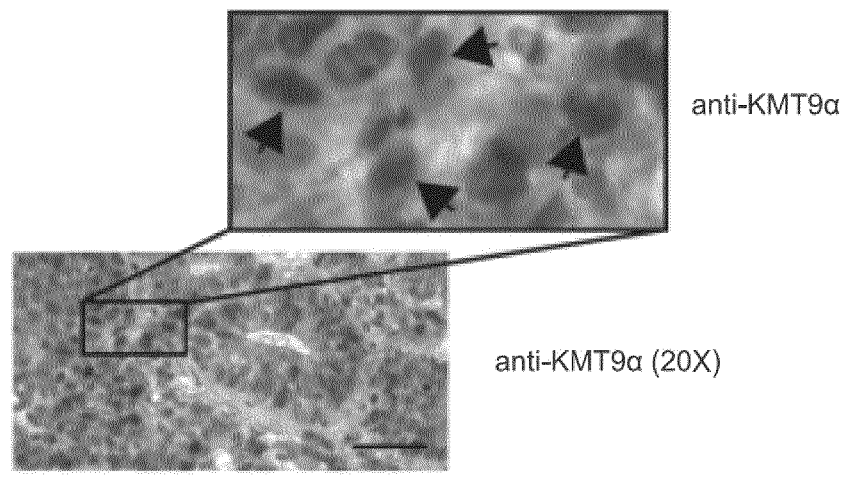

Figure 12- continued
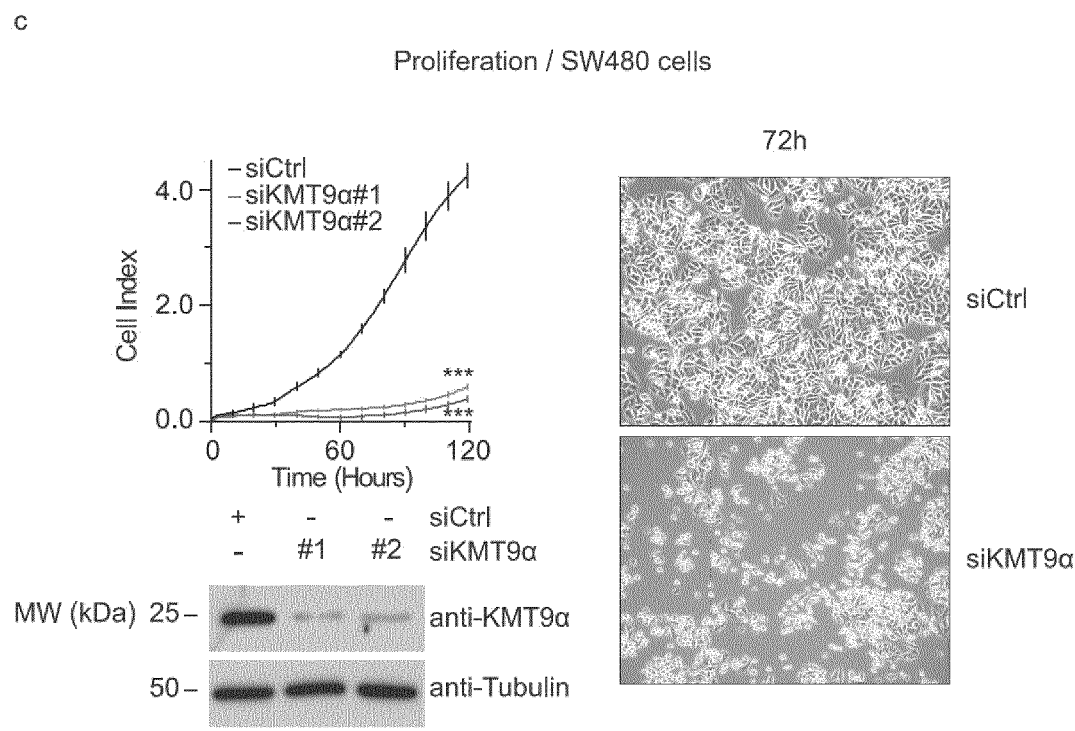

Figure 13- continued
e  Invasion / HCT116 p53-/- cells
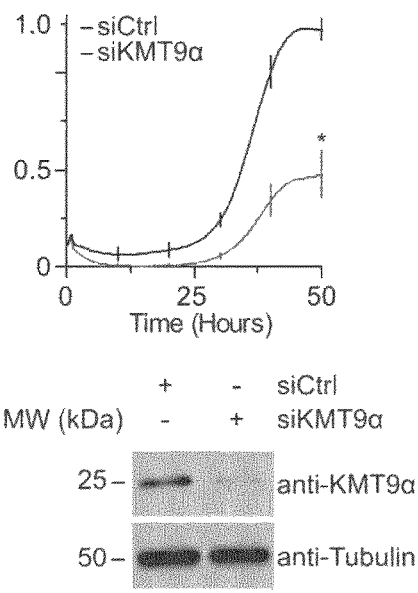
Figure 14
a
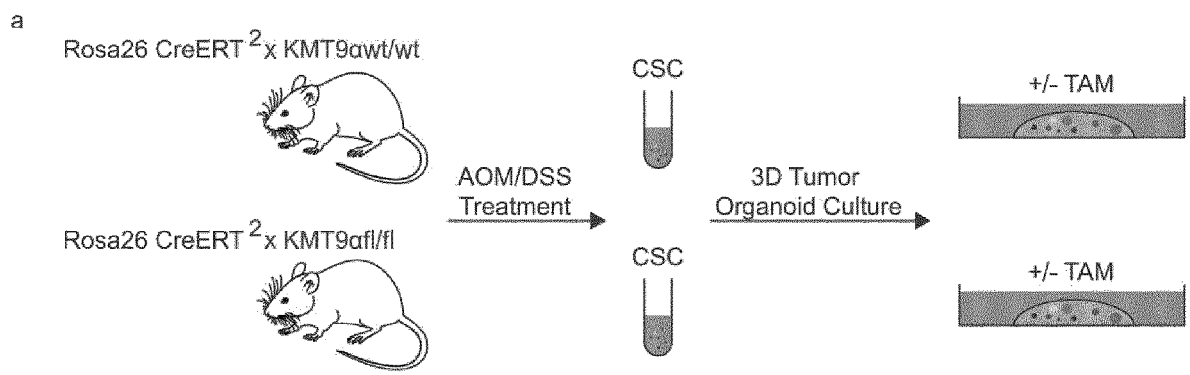

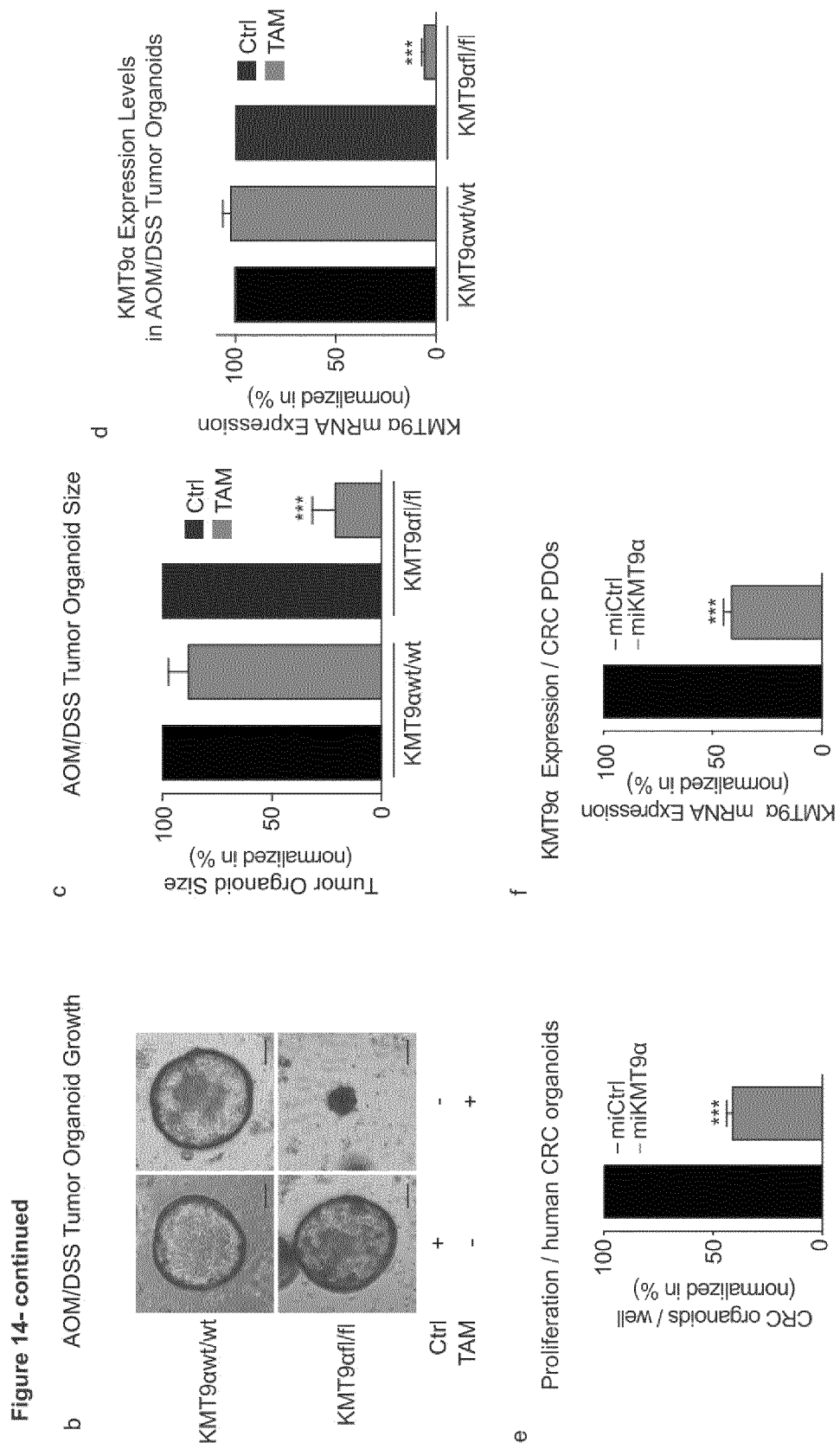

SEQUENCE LISTING

<160> NUMBER OF SEQ ID NOS: 35

<210> SEQ ID NO 1
<211> LENGTH: 64
<212> TYPE: DNA
<213> ORGANISM: Artificial Sequence
<220> FEATURE:
<223> OTHER INFORMATION: miRNA KMT9alpha

<400> SEQUENCE: 1
tgctgatgtg aactttgtta cagcgtgttt tggccactga ctgacacgct gtaaaagttc    60
acat                                                                 64

```
<210> SEQ ID NO 2
<211> LENGTH: 64
<212> TYPE: DNA
<213> ORGANISM: Artificial Sequence
<220> FEATURE:
<223> OTHER INFORMATION: miRNA KMT9alpha

<400> SEQUENCE: 2
cctgatgtga acttttacag cgtgtcagtc agtggccaaa acacgctgta acaaagttca    60
catc                                                                 64

<210> SEQ ID NO 3
<211> LENGTH: 24
<212> TYPE: RNA
<213> ORGANISM: Artificial Sequence
<220> FEATURE:
<223> OTHER INFORMATION: siCtrl

<400> SEQUENCE: 3
aaaguccuag auccacacgc aaau                                           24

<210> SEQ ID NO 4
<211> LENGTH: 25
<212> TYPE: RNA
<213> ORGANISM: Artificial Sequence
<220> FEATURE:
<223> OTHER INFORMATION: siKMT9alpha-3-UTR

<400> SEQUENCE: 4
ggaacuacau uagacuuagu ggaaa                                          25

<210> SEQ ID NO 5
<211> LENGTH: 25
<212> TYPE: RNA
<213> ORGANISM: Artificial Sequence
<220> FEATURE:
<223> OTHER INFORMATION: siKMT9alpha#1

<400> SEQUENCE: 5
acgcuguaac aaaguucaca uucaa                                          25

<210> SEQ ID NO 6
<211> LENGTH: 25
<212> TYPE: RNA
<213> ORGANISM: Artificial Sequence
<220> FEATURE:
<223> OTHER INFORMATION: siKMT9alpha#2

<400> SEQUENCE: 6
cacgcuguaa caaaguucac auuca                                          25

<210> SEQ ID NO 7
<211> LENGTH: 21
<212> TYPE: RNA
<213> ORGANISM: Artificial Sequence
<220> FEATURE:
<223> OTHER INFORMATION: siKMT9beta

<400> SEQUENCE: 7
ccugcugcug gagguggaau u                                              21
```

```
<210> SEQ ID NO 8
<211> LENGTH: 21
<212> TYPE: RNA
<213> ORGANISM: Artificial Sequence
<220> FEATURE:
<223> OTHER INFORMATION: siKMT9beta

<400> SEQUENCE: 8
uuccaccucc agcagcaggu g                                             21

<210> SEQ ID NO 9
<211> LENGTH: 25
<212> TYPE: RNA
<213> ORGANISM: Artificial Sequence
<220> FEATURE:
<223> OTHER INFORMATION: siMETTL21A

<400> SEQUENCE: 9
ccacggaauu uggguugcag aaauu                                         25

<210> SEQ ID NO 10
<211> LENGTH: 25
<212> TYPE: RNA
<213> ORGANISM: Artificial Sequence
<220> FEATURE:
<223> OTHER INFORMATION: siMETTL21B#1

<400> SEQUENCE: 10
ggacagagag cuucuuucag caccu                                         25

<210> SEQ ID NO 11
<211> LENGTH: 25
<212> TYPE: RNA
<213> ORGANISM: Artificial Sequence
<220> FEATURE:
<223> OTHER INFORMATION: siMETTL21B#2

<400> SEQUENCE: 11
ccaucauguc uucccugcaa acuau                                         25

<210> SEQ ID NO 12
<211> LENGTH: 20
<212> TYPE: DNA
<213> ORGANISM: Artificial Sequence
<220> FEATURE:
<223> OTHER INFORMATION: BIRC5-Primer

<400> SEQUENCE: 12
ggaccaccgc atctctacat                                               20

<210> SEQ ID NO 13
<211> LENGTH: 20
<212> TYPE: DNA
<213> ORGANISM: Artificial Sequence
<220> FEATURE:
<223> OTHER INFORMATION: BIRC5-primer

<400> SEQUENCE: 13
gaaacactgg gccaagtctg                                               20
```

<210> SEQ ID NO 14
<211> LENGTH: 20
<212> TYPE: DNA
<213> ORGANISM: Artificial Sequence
<220> FEATURE:
<223> OTHER INFORMATION: CDK1-primer

<400> SEQUENCE: 14
tacaggtcaa gtggtagcca                                          20

<210> SEQ ID NO 15
<211> LENGTH: 21
<212> TYPE: DNA
<213> ORGANISM: Artificial Sequence
<220> FEATURE:
<223> OTHER INFORMATION: CDK1-primer

<400> SEQUENCE: 15
agcacatcct gaagactgac t                                        21

<210> SEQ ID NO 16
<211> LENGTH: 20
<212> TYPE: DNA
<213> ORGANISM: Artificial Sequence
<220> FEATURE:
<223> OTHER INFORMATION: ODF2-primer

<400> SEQUENCE: 16
gatgagaaca cccctgtcca                                          20

<210> SEQ ID NO 17
<211> LENGTH: 20
<212> TYPE: DNA
<213> ORGANISM: Artificial Sequence
<220> FEATURE:
<223> OTHER INFORMATION: ODF2-primer

<400> SEQUENCE: 17
cgggcagatg attttccagg                                          20

<210> SEQ ID NO 18
<211> LENGTH: 21
<212> TYPE: DNA
<213> ORGANISM: Artificial Sequence
<220> FEATURE:
<223> OTHER INFORMATION: OSGIN2-primer

<400> SEQUENCE: 18
tccagttgca gtactttcg a                                         21

<210> SEQ ID NO 19
<211> LENGTH: 20
<212> TYPE: DNA
<213> ORGANISM: Artificial Sequence
<220> FEATURE:
<223> OTHER INFORMATION: OSGIN2-primer

<400> SEQUENCE: 19
tattatgcca agccccacca                                          20

<210> SEQ ID NO 20
<211> LENGTH: 20
<212> TYPE: DNA
<213> ORGANISM: Artificial Sequence
<220> FEATURE:
<223> OTHER INFORMATION: PGHDH-primer

<400> SEQUENCE: 20
ctgccggaag atcttgcaag                                            20

<210> SEQ ID NO 21
<211> LENGTH: 20
<212> TYPE: DNA
<213> ORGANISM: Artificial Sequence
<220> FEATURE:
<223> OTHER INFORMATION: PGHDH-primer

<400> SEQUENCE: 21
tccacattgt ccacacctgt                                            20

<210> SEQ ID NO 22
<211> LENGTH: 20
<212> TYPE: DNA
<213> ORGANISM: Artificial Sequence
<220> FEATURE:
<223> OTHER INFORMATION: RTKN2-primer

<400> SEQUENCE: 22
ttgctagctc acactaccct                                            20

<210> SEQ ID NO 23
<211> LENGTH: 20
<212> TYPE: DNA
<213> ORGANISM: Artificial Sequence
<220> FEATURE:
<223> OTHER INFORMATION: RTKN2-primer

<400> SEQUENCE: 23
gcatcctcag ccatacaagc                                            20

<210> SEQ ID NO 24
<211> LENGTH: 20
<212> TYPE: DNA
<213> ORGANISM: Artificial Sequence
<220> FEATURE:
<223> OTHER INFORMATION: STIL-primer

<400> SEQUENCE: 24
aatgtgcact ttggaaccca                                            20

<210> SEQ ID NO 25
<211> LENGTH: 20
<212> TYPE: DNA
<213> ORGANISM: Artificial Sequence
<220> FEATURE:
<223> OTHER INFORMATION: STIL-primer

<400> SEQUENCE: 25
agcaagtcgg atggtcttct                                            20

<210> SEQ ID NO 26
<211> LENGTH: 20
<212> TYPE: DNA
<213> ORGANISM: Artificial Sequence
<220> FEATURE:

-continued

```
<223> OTHER INFORMATION: VRK1-primer

<400> SEQUENCE: 26
tcagagtcag ttggcagtga                                              20

<210> SEQ ID NO 27
<211> LENGTH: 20
<212> TYPE: DNA
<213> ORGANISM: Artificial Sequence
<220> FEATURE:
<223> OTHER INFORMATION: VRK1-primer

<400> SEQUENCE: 27
ggttttgcag ctcgttggta                                              20

<210> SEQ ID NO 28
<211> LENGTH: 20
<212> TYPE: DNA
<213> ORGANISM: Artificial Sequence
<220> FEATURE:
<223> OTHER INFORMATION: MTA1-primer

<400> SEQUENCE: 28
cgagtcgctc aagtcctacc                                              20

<210> SEQ ID NO 29
<211> LENGTH: 20
<212> TYPE: DNA
<213> ORGANISM: Artificial Sequence
<220> FEATURE:
<223> OTHER INFORMATION: MTA1-primer

<400> SEQUENCE: 29
tggtaccggt ttcctactcg                                              20

<210> SEQ ID NO 30
<211> LENGTH: 25
<212> TYPE: RNA
<213> ORGANISM: Artificial Sequence
<220> FEATURE:
<223> OTHER INFORMATION: siMETTL21A#2

<400> SEQUENCE: 30
gccgaauucg cuaugaacgg gauaa                                        25

<210> SEQ ID NO 31
<211> LENGTH: 214
<212> TYPE: PRT
<213> ORGANISM: Homo sapiens

<400> SEQUENCE: 31

Met Ala Gly Glu Asn Phe Ala Thr Pro Phe His Gly His Val Gly Arg
1               5                   10                  15

Gly Ala Phe Ser Asp Val Tyr Glu Pro Ala Glu Asp Thr Phe Leu Leu
            20                  25                  30

Leu Asp Ala Leu Glu Ala Ala Ala Glu Leu Ala Gly Val Glu Ile
        35                  40                  45

Cys Leu Glu Val Gly Ser Gly Ser Gly Val Val Ser Ala Phe Leu Ala
    50                  55                  60

Ser Met Ile Gly Pro Gln Ala Leu Tyr Met Cys Thr Asp Ile Asn Pro
65                  70                  75                  80

Glu Ala Ala Ala Cys Thr Leu Glu Thr Ala Arg Cys Asn Lys Val His
                85                  90                  95
```

```
Ile Gln Pro Val Ile Thr Asp Leu Val Lys Gly Leu Pro Arg Leu
                100                 105                 110

Thr Glu Lys Val Asp Leu Leu Val Phe Asn Pro Pro Tyr Val Val Thr
            115                 120                 125

Pro Pro Gln Glu Val Gly Ser His Gly Ile Glu Ala Ala Trp Ala Gly
130                 135                 140

Gly Arg Asn Gly Arg Glu Val Met Asp Arg Phe Phe Pro Leu Val Pro
145                 150                 155                 160

Asp Leu Leu Ser Pro Arg Gly Leu Phe Tyr Leu Val Thr Ile Lys Glu
                165                 170                 175

Asn Asn Pro Glu Glu Ile Leu Lys Ile Met Lys Thr Lys Gly Leu Gln
            180                 185                 190

Gly Thr Thr Ala Leu Ser Arg Gln Ala Gly Gln Glu Thr Leu Ser Val
        195                 200                 205

Leu Lys Phe Thr Lys Ser
    210

<210> SEQ ID NO 32
<211> LENGTH: 125
<212> TYPE: PRT
<213> ORGANISM: Homo sapiens

<400> SEQUENCE: 32

Met Lys Leu Leu Thr His Asn Leu Leu Ser Ser His Val Arg Gly Val
1               5                   10                  15

Gly Ser Arg Gly Phe Pro Leu Arg Leu Gln Ala Thr Glu Val Arg Ile
            20                  25                  30

Cys Pro Val Glu Phe Asn Pro Asn Phe Val Ala Arg Met Ile Pro Lys
        35                  40                  45

Val Glu Trp Ser Ala Phe Leu Glu Ala Ala Asp Asn Leu Arg Leu Ile
    50                  55                  60

Gln Val Pro Lys Gly Pro Val Glu Gly Tyr Glu Asn Glu Glu Phe
65                  70                  75                  80

Leu Arg Thr Met His His Leu Leu Glu Val Glu Val Ile Glu Gly
                85                  90                  95

Thr Leu Gln Cys Pro Glu Ser Gly Arg Met Phe Pro Ile Ser Arg Gly
            100                 105                 110

Ile Pro Asn Met Leu Leu Ser Glu Glu Thr Glu Ser
        115                 120                 125

<210> SEQ ID NO 33
<211> LENGTH: 218
<212> TYPE: PRT
<213> ORGANISM: Homo sapiens

<400> SEQUENCE: 33

Met Ala Leu Val Pro Tyr Glu Glu Thr Thr Glu Phe Gly Leu Gln Lys
1               5                   10                  15

Phe His Lys Pro Leu Ala Thr Phe Ser Phe Ala Asn His Thr Ile Gln
            20                  25                  30

Ile Arg Gln Asp Trp Arg His Leu Gly Val Ala Ala Val Val Trp Asp
        35                  40                  45

Ala Ala Ile Val Leu Ser Thr Tyr Leu Glu Met Gly Ala Val Glu Leu
    50                  55                  60

Arg Gly Arg Ser Ala Val Glu Leu Gly Ala Gly Thr Gly Leu Val Gly
65                  70                  75                  80
```

-continued

```
Ile Val Ala Ala Leu Leu Gly Ala His Val Thr Ile Thr Asp Arg Lys
                85                  90                  95

Val Ala Leu Glu Phe Leu Lys Ser Asn Val Gln Ala Asn Leu Pro Pro
            100                 105                 110

His Ile Gln Thr Lys Thr Val Val Lys Glu Leu Thr Trp Gly Gln Asn
        115                 120                 125

Leu Gly Ser Phe Ser Pro Gly Glu Phe Asp Leu Ile Leu Gly Ala Asp
    130                 135                 140

Ile Ile Tyr Leu Glu Glu Thr Phe Thr Asp Leu Leu Gln Thr Leu Glu
145                 150                 155                 160

His Leu Cys Ser Asn His Ser Val Ile Leu Leu Ala Cys Arg Ile Arg
                165                 170                 175

Tyr Glu Arg Asp Asn Asn Phe Leu Ala Met Leu Glu Arg Gln Phe Thr
            180                 185                 190

Val Arg Lys Val His Tyr Asp Pro Glu Lys Asp Val His Ile Tyr Glu
        195                 200                 205

Ala Gln Lys Arg Asn Gln Lys Glu Asp Leu
    210                 215
```

<210> SEQ ID NO 34
<211> LENGTH: 226
<212> TYPE: PRT
<213> ORGANISM: Homo sapiens

<400> SEQUENCE: 34

```
Met Ala Asp Pro Gly Pro Asp Pro Glu Ser Glu Ser Glu Ser Val Phe
1               5                   10                  15

Pro Arg Glu Val Gly Leu Phe Ala Asp Ser Tyr Ser Glu Lys Ser Gln
            20                  25                  30

Phe Cys Phe Cys Gly His Val Leu Thr Ile Thr Gln Asn Phe Gly Ser
        35                  40                  45

Arg Leu Gly Val Ala Ala Arg Val Trp Asp Ala Ala Leu Ser Leu Cys
    50                  55                  60

Asn Tyr Phe Glu Ser Gln Asn Val Asp Phe Arg Gly Lys Lys Val Ile
65                  70                  75                  80

Glu Leu Gly Ala Gly Thr Gly Ile Val Gly Ile Leu Ala Ala Leu Gln
                85                  90                  95

Gly Gly Asp Val Thr Ile Thr Asp Leu Pro Leu Ala Leu Glu Gln Ile
            100                 105                 110

Gln Gly Asn Val Gln Ala Asn Val Pro Ala Gly Gly Gln Ala Gln Val
        115                 120                 125

Arg Ala Leu Ser Trp Gly Ile Asp His His Val Phe Pro Ala Asn Tyr
    130                 135                 140

Asp Leu Val Leu Gly Ala Asp Ile Val Tyr Leu Glu Pro Thr Phe Pro
145                 150                 155                 160

Leu Leu Leu Gly Thr Leu Gln His Leu Cys Arg Pro His Gly Thr Ile
                165                 170                 175

Tyr Leu Ala Ser Lys Met Arg Lys Glu His Gly Thr Glu Ser Phe Phe
            180                 185                 190

Gln His Leu Leu Pro Gln His Phe Gln Leu Glu Leu Ala Gln Arg Asp
        195                 200                 205
```

-continued

Glu Asp Glu Asn Val Asn Ile Tyr Arg Ala Arg His Arg Glu Pro Arg
    210                 215                 220

Pro Ala
225

<210> SEQ ID NO 35
<211> LENGTH: 1537
<212> TYPE: PRT
<213> ORGANISM: Homo sapiens

<400> SEQUENCE: 35

Met Gly Glu Lys Leu Glu Leu Arg Leu Lys Ser Pro Val Gly Ala Glu
1               5                   10                  15

Pro Ala Val Tyr Pro Trp Pro Leu Pro Val Tyr Asp Lys His His Asp
            20                  25                  30

Ala Ala His Glu Ile Ile Glu Thr Ile Arg Trp Val Cys Glu Glu Ile
        35                  40                  45

Pro Asp Leu Lys Leu Ala Met Glu Asn Tyr Val Leu Ile Asp Tyr Asp
    50                  55                  60

Thr Lys Ser Phe Glu Ser Met Gln Arg Leu Cys Asp Lys Tyr Asn Arg
65                  70                  75                  80

Ala Ile Asp Ser Ile His Gln Leu Trp Lys Gly Thr Thr Gln Pro Met
                85                  90                  95

Lys Leu Asn Thr Arg Pro Ser Thr Gly Leu Leu Arg His Ile Leu Gln
            100                 105                 110

Gln Val Tyr Asn His Ser Val Thr Asp Pro Glu Lys Leu Asn Asn Tyr
        115                 120                 125

Glu Pro Phe Ser Pro Glu Val Tyr Gly Glu Thr Ser Phe Asp Leu Val
    130                 135                 140

Ala Gln Met Ile Asp Glu Ile Lys Met Thr Asp Asp Asp Leu Phe Val
145                 150                 155                 160

Asp Leu Gly Ser Gly Val Gly Gln Val Val Leu Gln Val Ala Ala Ala
                165                 170                 175

Thr Asn Cys Lys His His Tyr Gly Val Glu Lys Ala Asp Ile Pro Ala
            180                 185                 190

Lys Tyr Ala Glu Thr Met Asp Arg Glu Phe Arg Lys Trp Met Lys Trp
        195                 200                 205

Tyr Gly Lys Lys His Ala Glu Tyr Thr Leu Glu Arg Gly Asp Phe Leu
    210                 215                 220

Ser Glu Glu Trp Arg Glu Arg Ile Ala Asn Thr Ser Val Ile Phe Val
225                 230                 235                 240

Asn Asn Phe Ala Phe Gly Pro Glu Val Asp His Gln Leu Lys Glu Arg
                245                 250                 255

Phe Ala Asn Met Lys Glu Gly Gly Arg Ile Val Ser Ser Lys Pro Phe
            260                 265                 270

Ala Pro Leu Asn Phe Arg Ile Asn Ser Arg Asn Leu Ser Asp Ile Gly
        275                 280                 285

Thr Ile Met Arg Val Val Glu Leu Ser Pro Leu Lys Gly Ser Val Ser
    290                 295                 300

Trp Thr Gly Lys Pro Val Ser Tyr Tyr Leu His Thr Ile Asp Arg Thr
305                 310                 315                 320

Ile Leu Glu Asn Tyr Phe Ser Ser Leu Lys Asn Pro Lys Leu Arg Glu
                325                 330                 335

```
Glu Gln Glu Ala Ala Arg Arg Gln Gln Arg Glu Ser Lys Ser Asn
            340                 345                 350
Ala Ala Thr Pro Thr Lys Gly Pro Glu Gly Lys Val Ala Gly Pro Ala
            355                 360                 365
Asp Ala Pro Met Asp Ser Gly Ala Glu Glu Lys Ala Gly Ala Ala
        370                 375                 380
Thr Val Lys Lys Pro Ser Pro Ser Lys Ala Arg Lys Lys Lys Leu Asn
385                 390                 395                 400
Lys Lys Gly Arg Lys Met Ala Gly Arg Lys Arg Gly Arg Pro Lys Lys
                405                 410                 415
Met Asn Thr Ala Asn Pro Glu Arg Lys Pro Lys Lys Asn Gln Thr Ala
            420                 425                 430
Leu Asp Ala Leu His Ala Gln Thr Val Ser Gln Thr Ala Ala Ser Ser
        435                 440                 445
Pro Gln Asp Ala Tyr Arg Ser Pro His Ser Pro Phe Tyr Gln Leu Pro
    450                 455                 460
Pro Ser Val Gln Arg His Ser Pro Asn Pro Leu Leu Val Ala Pro Thr
465                 470                 475                 480
Pro Pro Ala Leu Gln Lys Leu Leu Glu Ser Phe Lys Ile Gln Tyr Leu
                485                 490                 495
Gln Phe Leu Ala Tyr Thr Lys Thr Pro Gln Tyr Lys Ala Ser Leu Gln
            500                 505                 510
Glu Leu Leu Gly Gln Glu Lys Glu Lys Asn Ala Gln Leu Leu Gly Ala
        515                 520                 525
Ala Gln Gln Leu Leu Ser His Cys Gln Ala Gln Lys Glu Glu Ile Arg
    530                 535                 540
Arg Leu Phe Gln Gln Lys Leu Asp Glu Leu Gly Val Lys Ala Leu Thr
545                 550                 555                 560
Tyr Asn Asp Leu Ile Gln Ala Gln Lys Glu Ile Ser Ala His Asn Gln
                565                 570                 575
Gln Leu Arg Glu Gln Ser Glu Gln Leu Glu Gln Asp Asn Arg Ala Leu
            580                 585                 590
Arg Gly Gln Ser Leu Gln Leu Leu Lys Ala Arg Cys Glu Glu Leu Gln
        595                 600                 605
Leu Asp Trp Ala Thr Leu Ser Leu Glu Lys Leu Leu Lys Glu Lys Gln
    610                 615                 620
Ala Leu Lys Ser Gln Ile Ser Glu Lys Gln Arg His Cys Leu Glu Leu
625                 630                 635                 640
Gln Ile Ser Ile Val Glu Leu Glu Lys Ser Gln Arg Gln Gln Glu Leu
                645                 650                 655
Leu Gln Leu Lys Ser Cys Val Pro Pro Asp Asp Ala Leu Ser Leu His
            660                 665                 670
Leu Arg Gly Lys Gly Ala Leu Gly Arg Glu Leu Glu Pro Asp Ala Ser
        675                 680                 685
Arg Leu His Leu Glu Leu Asp Cys Thr Lys Phe Ser Leu Pro His Leu
    690                 695                 700
Ser Ser Met Ser Pro Glu Leu Ser Met Asn Gly Gln Ala Ala Gly Tyr
705                 710                 715                 720
Glu Leu Cys Gly Val Leu Ser Arg Pro Ser Lys Gln Asn Thr Pro
                725                 730                 735
Gln Tyr Leu Ala Ser Pro Leu Asp Gln Glu Val Val Pro Cys Thr Pro
            740                 745                 750
```

```
Ser His Val Gly Arg Pro Arg Leu Glu Lys Leu Ser Gly Leu Ala Ala
        755                 760                 765

Pro Asp Tyr Thr Arg Leu Ser Pro Ala Lys Ile Val Leu Arg Arg His
770                 775                 780

Leu Ser Gln Asp His Thr Val Pro Gly Arg Pro Ala Ala Ser Glu Leu
785                 790                 795                 800

His Ser Arg Ala Glu His Thr Lys Glu Asn Gly Leu Pro Tyr Gln Ser
            805                 810                 815

Pro Ser Val Pro Gly Ser Met Lys Leu Ser Pro Gln Asp Pro Arg Pro
                820                 825                 830

Leu Ser Pro Gly Ala Leu Gln Leu Ala Gly Glu Lys Ser Ser Glu Lys
            835                 840                 845

Gly Leu Arg Glu Arg Ala Tyr Gly Ser Ser Gly Glu Leu Ile Thr Ser
850                 855                 860

Leu Pro Ile Ser Ile Pro Leu Ser Thr Val Gln Pro Asn Lys Leu Pro
865                 870                 875                 880

Val Ser Ile Pro Leu Ala Ser Val Val Leu Pro Ser Arg Ala Glu Arg
            885                 890                 895

Ala Arg Ser Thr Pro Ser Pro Val Leu Gln Pro Arg Asp Pro Ser Ser
            900                 905                 910

Thr Leu Glu Lys Gln Ile Gly Ala Asn Ala His Gly Ala Gly Ser Arg
            915                 920                 925

Ser Leu Ala Leu Ala Pro Ala Gly Phe Ser Tyr Ala Gly Ser Val Ala
            930                 935                 940

Ile Ser Gly Ala Leu Ala Gly Ser Pro Ala Ser Leu Thr Pro Gly Ala
945                 950                 955                 960

Glu Pro Ala Thr Leu Asp Glu Ser Ser Ser Gly Ser Leu Phe Ala
                965                 970                 975

Thr Val Gly Ser Arg Ser Ser Thr Pro Gln His Pro Leu Leu Leu Ala
            980                 985                 990

Gln Pro Arg Asn Ser Leu Pro Ala  Ser Pro Ala His Gln Leu Ser Ser
            995                 1000                 1005

Ser Pro Arg Leu Gly Gly Ala  Ala Gln Gly Pro Leu  Pro Glu Ala
    1010                1015                 1020

Ser Lys Gly Asp Leu Pro Ser  Asp Ser Gly Phe Ser  Asp Pro Glu
    1025                1030                 1035

Ser Glu Ala Lys Arg Arg Ile  Val Phe Thr Ile Thr  Thr Gly Ala
    1040                1045                 1050

Gly Ser Ala Lys Gln Ser Pro  Ser Ser Lys His Ser  Pro Leu Thr
    1055                1060                 1065

Ala Ser Ala Arg Gly Asp Cys  Val Pro Ser His Gly  Gln Asp Ser
    1070                1075                 1080

Arg Arg Arg Gly Arg Arg Lys  Arg Ala Ser Ala Gly  Thr Pro Ser
    1085                1090                 1095

Leu Ser Ala Gly Val Ser Pro  Lys Arg Arg Ala Leu  Pro Ser Val
    1100                1105                 1110

Ala Gly Leu Phe Thr Gln Pro  Ser Gly Ser Pro Leu  Asn Leu Asn
    1115                1120                 1125

Ser Met Val Ser Asn Ile Asn  Gln Pro Leu Glu Ile  Thr Ala Ile
    1130                1135                 1140

Ser Ser Pro Glu Thr Ser Leu  Lys Ser Ser Pro Val  Pro Tyr Gln
    1145                1150                 1155
```

```
Asp His Asp Gln Pro Pro Val Leu Lys Lys Glu Arg Pro Leu Ser
    1160            1165             1170

Gln Thr Asn Gly Ala His Tyr Ser Pro Leu Thr Ser Asp Glu Glu
    1175            1180             1185

Pro Gly Ser Glu Asp Glu Pro Ser Ser Ala Arg Ile Glu Arg Lys
    1190            1195             1200

Ile Ala Thr Ile Ser Leu Glu Ser Lys Ser Pro Lys Thr Leu
    1205            1210             1215

Glu Asn Gly Gly Gly Leu Ala Gly Arg Lys Pro Ala Pro Ala Gly
    1220            1225             1230

Glu Pro Val Asn Ser Ser Lys Trp Lys Ser Thr Phe Ser Pro Ile
    1235            1240             1245

Ser Asp Ile Gly Leu Ala Lys Ser Ala Asp Ser Pro Leu Gln Ala
    1250            1255             1260

Ser Ser Ala Leu Ser Gln Asn Ser Leu Phe Thr Phe Arg Pro Ala
    1265            1270             1275

Leu Glu Glu Pro Ser Ala Asp Ala Lys Leu Ala Ala His Pro Arg
    1280            1285             1290

Lys Gly Phe Pro Gly Ser Leu Ser Gly Ala Asp Gly Leu Ser Pro
    1295            1300             1305

Gly Thr Asn Pro Ala Asn Gly Cys Thr Phe Gly Gly Gly Leu Ala
    1310            1315             1320

Ala Asp Leu Ser Leu His Ser Phe Ser Asp Gly Ala Ser Leu Pro
    1325            1330             1335

His Lys Gly Pro Glu Ala Ala Gly Leu Ser Ser Pro Leu Ser Phe
    1340            1345             1350

Pro Ser Gln Arg Gly Lys Glu Gly Ser Asp Ala Asn Pro Phe Leu
    1355            1360             1365

Ser Lys Arg Gln Leu Asp Gly Leu Ala Gly Leu Lys Gly Glu Gly
    1370            1375             1380

Ser Arg Gly Lys Glu Ala Gly Glu Gly Gly Leu Pro Leu Cys Gly
    1385            1390             1395

Pro Thr Asp Lys Thr Pro Leu Leu Ser Gly Lys Ala Ala Lys Ala
    1400            1405             1410

Arg Asp Arg Glu Val Asp Leu Lys Asn Gly His Asn Leu Phe Ile
    1415            1420             1425

Ser Ala Ala Ala Val Pro Pro Gly Ser Leu Leu Ser Gly Pro Gly
    1430            1435             1440

Leu Ala Pro Ala Ala Ser Ser Ala Gly Gly Ala Ala Ser Ser Ala
    1445            1450             1455

Gln Thr His Arg Ser Phe Leu Gly Pro Phe Pro Pro Gly Pro Gln
    1460            1465             1470

Phe Ala Leu Gly Pro Met Ser Leu Gln Ala Asn Leu Gly Ser Val
    1475            1480             1485

Ala Gly Ser Ser Val Leu Gln Ser Leu Phe Ser Ser Val Pro Ala
    1490            1495             1500

Ala Ala Gly Leu Val His Val Ser Ser Ala Ala Thr Arg Leu Thr
    1505            1510             1515

Asn Ser His Ala Met Gly Ser Phe Ser Gly Val Ala Gly Gly Thr
    1520            1525             1530

Val Gly Gly Asn
    1535
```

INHIBITION OF HISTONE METHYL TRANSFERASES TO TREAT CANCER

FIELD OF THE INVENTION

The present invention relates to an inhibitor selected from the group consisting of a selective KMT9-inhibitor, a selective METTL21A-inhibitor and a selective METTL21B-inhibitor for use in the treatment of cancer. KMT9, METTL21A and METTL21B are shown herein to be histone methyltransferases, which are implicated in pathways essential for the cell. Inhibition of either of these novel methyl transferases has a pronounced negative effect on the proliferation of cancer cells.

BACKGROUND OF THE INVENTION

Posttranslational modifications of histones such as methylation regulate chromatin structure and gene expression, and dysregulation of these mostly reversible modifications has been shown to have a central role in cancer onset and cancer progression[1,3].

Histone methyl transferases (HMT) possess high selectivity as regards the targeted histone lysine residue. Further, the pattern of methylation is specific for each HMT. There are two families of HMTs, namely the SET domain-containing HMTs (with the four subfamilies SET1 [a specific member here is EZH2], SET2, SUV39 and RIZ) and other HMTs, wherein DOT1L is thus far the only HMT that does not contain a SET domain. Further details in this respect as well as information on the effect of HMT-inhibition and specific inhibitors be found in the review by Morera et al. Targeting histone methyltransferases and demethylases in clinical trials for cancer therapy. *Clinical Epigenetics*, 8:57 (2016), doi: 10.1186/s13148-016-0223-4, 2016.

EZH2 and DOT1L have in particular been studied over the last years when it comes to their role in cancer. EZH2 is the catalytic component of the polycomb repressive complex 2 (PRC2), which performs three successive methyl transfer reactions arriving at H3K27me3. DOT1L is capable of catalyzing mono-, di-, and trimethylation of H3K79. While H3K79 is an activating mark when it comes to gene transcription, H3K27me3 is associated with gene silencing.

The inhibition of DOT1L is in particular implicated in the treatment of leukemias presenting a chromosomal translocation of the mixed-lineage leukemia (MLL) gene (chromosome 11q23), such as e.g. acute myeloid leukemias (AML), acute lymphoblastic leukemias (ALL) and the biphenotypic (mixed lineage) leukemias (MLL). Selective inhibitors have been and are being developed against DOT1L with EPZ004777 and EPZ-5676 being the most prominent inhibitors.

When it comes to EZH2, increased silencing of tumor suppressor genes has been reported in cancer cells upon EZH2 overexpression. Therefore, inhibition of EZH2 should restore expression of tumor suppressor genes and quite a number of inhibitors have been developed, some of which undergo clinical testing (such as e.g. tazemetostat tested in patients with advanced solid tumors or with relapsed or refractory B cell lymphomas; or GSK2816126 tested in patients with relapsed or refractory diffuse large B cell and transformed follicular lymphoma).

There is of course an ongoing need for novel targets and corresponding inhibitors that can be used to treat cancer, wherein it is highly desirable that these novel inhibitors are as selective as possible when it comes to their respective targets in order not to interfere with other than the intended signaling pathways in the cells.

OBJECTS AND SUMMARY OF THE INVENTION

The inventors of the present invention have surprisingly found novel targets, namely novel histone methyltransferases. The inventors further found that the inhibition of these novel histone methyltransferases has a pronounced negative effect on the proliferation of cancer cells. In other words, inhibitors of the histone methyltransferases described herein can be used for the treatment of cancer.

In the first aspect, the present invention is directed to an inhibitor selected from the group consisting of a selective KMT9-inhibitor, a selective METTL21A-inhibitor and a selective METTL21B-inhibitor, for use in the treatment of cancer. It is emphasized that said inhibitor is not a non-selective protein methyltransferase inhibitor. Such a non-selective protein methyltransferase inhibitor can e.g. be selected from the group consisting of sinefungin, 3-deazaneplanocin A (also referred to as "DZNep" or "C-c3Ado") and S-adenosyl-L-homocysteine (SAH).

In an embodiment thereof, said cancer is selected from the group consisting of prostate cancer, breast cancer, ovarian cancer, colon cancer, colorectal cancer, glioblastoma, lung cancer, neuroblastoma, osteosarcoma, liposarcoma and leukemia. It is noted that the prostate cancer may be hormone-dependent prostate cancer or castration-resistant prostate cancer, and that the castration-resistant prostate cancer may further be resistant to enzalutamide. It is further noted that the lung cancer may be non-small cell lung cancer or small cell lung cancer. Prostate cancer, and in particular castration-resistant prostate cancer, is particularly preferred to be treated by an inhibitor of the present invention.

In another embodiment thereof, said cancer is selected from the group consisting of breast cancer, ovarian cancer, colon cancer, glioblastoma, lung cancer, neuroblastoma, osteosarcoma, liposarcoma, colorectal cancer, rectal adenocarcinoma, non-small cell lung carcinoma, small cell lung carcinoma, large cell lung carcinoma, lung adenocarcinoma, mesothelioma, ovarian carcinoma, endometrium adenocarcinoma, erythroleukemia, medulloblastoma, astrocytoma, Ewing sarcoma, myelodysplastic syndrome (MDS), diffuse large B-cell lymphoma, leukemia, myelogenic leukemia, medulloblastoma, myeloid leukemia, acute monocytic leukemia, gallbladder carcinoma, cecum adenocarcinoma, gastric adenocarcinoma, stomach adenocarcinoma, renal cell carcinoma, bladder carcinoma, melanoma, cervical squamous cell carcinoma, pancreatic carcinoma, chondrosarcoma, duodenal adenocarcinoma, rhabdomyosarcoma, hepatocellular carcinoma and uterine adenocarcinoma.

In embodiments A of the first aspect, said inhibitor for use in treating cancer is a selective KMT9-inhibitor, wherein said selective KMT9-inhibitor is preferably selected from the group consisting of a small molecule selective for KMT9-inhibition, a small chemical fragment selective for KMT9-inhibition, an antibody directed to KMT9alpha and/or KMT9beta or an antigen-binding fragment thereof, a siRNA directed to the KMT9alpha mRNA and/or the KMT9beta mRNA or a polynucleotide encoding said siRNA, and a gRNA directed to the KMT9alpha gene and/or KMT9beta gene or a polynucleotide encoding said gRNA. Said KMT9-inhibitor is not a non-selective protein methyltransferase inhibitor.

In embodiment A1, said selective KMT9-inhibitor is a small molecule selective for KMT9-inhibition. In embodiment A2, said selective KMT9-inhibitor is a small chemical fragment selective for KMT9-inhibition. "Selective" as used in this respect can mean that the %-inhibition is higher for KMT9 compared to another HMT, preferably compared to DOT1L.

In embodiment A3, said selective KMT9-inhibitor is an antibody directed to KMT9alpha and/or KMT9beta or an antigen-binding fragment thereof, preferably an antibody directed to KMT9alpha or an antigen-binding fragment thereof.

In embodiment A4, said selective KMT9-inhibitor is a siRNA directed to the KMT9alpha mRNA and/or KMT9beta mRNA or a polynucleotide encoding said siRNA, preferably a siRNA directed to the KMT9alpha mRNA or a polynucleotide encoding said siRNA. This system is used in order to reduce, preferably eliminate, KMT9alpha and/or KMT9beta, preferably KMT9alpha.

In embodiment A5, said selective KMT9-inhibitor is a gRNA directed to the KMT9alpha gene and/or KMT9beta gene or a polynucleotide encoding said gRNA, preferably a gRNA directed to the KMT9alpha gene or a polynucleotide encoding said gRNA. Preferably, said gRNA is used in combination with Cas9 or a polynucleotide encoding Cas9. This system is used in order to reduce, preferably eliminate, KMT9alpha and/or KMT9beta gene expression or to reduce, preferably eliminate, KMT9 histone methyltransferase activity.

In embodiment A6, said cancer is selected from the group consisting of prostate cancer, breast cancer, ovarian cancer, colon cancer, colorectal cancer, glioblastoma, lung cancer, neuroblastoma, osteosarcoma, liposarcoma and leukemia. It is noted that the prostate cancer may be hormone-dependent prostate cancer or castration-resistant prostate cancer, and that the castration-resistant prostate cancer may further be resistant to enzalutamide. It is further noted that the lung cancer may be non-small cell lung cancer. Prostate cancer, and in particular castration-resistant prostate cancer, is particularly preferred to be treated by a selective KMT9-inhibitor of the present invention.

In embodiments B of the first aspect, said inhibitor for use in treating cancer is a selective METTL21A-inhibitor, wherein said selective METTL21A-inhibitor is preferably selected from the group consisting of a small molecule selective for METTL21A-inhibition, a small chemical fragment selective for METTL21A-inhibition, an antibody directed to METTL21A or an antigen-binding fragment thereof, a siRNA directed to the METTL21A mRNA or a polynucleotide encoding said siRNA, and a gRNA directed to the METTL21A gene or a polynucleotide encoding said gRNA. Said METTL21A-inhibitor is not a non-selective protein methyltransferase inhibitor.

In embodiment B1, said selective METTL21A-inhibitor is a small molecule selective for METTL21A-inhibition. In embodiment B2, said selective METTL21A-inhibitor is a small chemical fragment selective for METTL21A-inhibition. "Selective" as used in this respect can mean that the %-inhibition is higher for METTL21A compared to another HMT, preferably compared to DOT1L.

In embodiment B3, said selective METTL21A-inhibitor is an antibody directed to METTL21A or an antigen-binding fragment thereof.

In embodiment B4, said selective METTL21A-inhibitor is a siRNA directed to the METTL21A mRNA or a polynucleotide encoding said siRNA. This system is used in order to reduce, preferably eliminate, METTL21A.

In embodiment B5, said selective METTL21A-inhibitor is a gRNA directed to the METTL21A gene or a polynucleotide encoding said gRNA. Preferably, said gRNA is used in combination with Cas9 or a polynucleotide encoding Cas9. This system is used in order to reduce, preferably eliminate, METTL21A gene expression or to reduce, preferably eliminate, METTL21A histone methyltransferase activity.

In embodiment B6, said cancer is selected from the group consisting of prostate cancer, breast cancer, glioblastoma, lung cancer, neuroblastoma and leukemia. It is noted that the prostate cancer may be hormone-dependent prostate cancer or castration-resistant prostate cancer, and that the castration-resistant prostate cancer may further be resistant to enzalutamide. It is further noted that the lung cancer may be small cell lung cancer. Prostate cancer, and in particular castration-resistant prostate cancer, is particularly preferred to be treated by a selective METTL21A-inhibitor of the present invention.

In embodiments C of the first aspect, said inhibitor for use in treating cancer is a selective METTL21B-inhibitor, wherein said selective METTL21B-inhibitor is preferably selected from the group consisting of a small molecule selective for METTL21B-inhibition, a small chemical fragment selective for METTL21B-inhibition, an antibody directed to METTL21B or an antigen-binding fragment thereof, a siRNA directed to the METTL21B mRNA or a polynucleotide encoding said siRNA, and a gRNA directed to the METTL21B gene or a polynucleotide encoding said gRNA. Said METTL21B-inhibitor is not a non-selective protein methyltransferase inhibitor.

In embodiment C1, said selective METTL21B-inhibitor is a small molecule selective for METTL21B-inhibition. In embodiment C2, said selective METTL21B-inhibitor is a small chemical fragment selective for METTL21B-inhibition. "Selective" as used in this respect can mean that the %-inhibition is higher for METTL21B compared to another HMT, preferably compared to DOT1L.

In embodiment C3, said selective METTL21B-inhibitor is an antibody directed to METTL21B or an antigen-binding fragment thereof.

In embodiment C4, said selective METTL21B-inhibitor is a siRNA directed to the METTL21B mRNA or a polynucleotide encoding said siRNA. This system is used in order to reduce, preferably eliminate, METTL21B.

In embodiment C5, said selective METTL21B-inhibitor is a gRNA directed to the METTL21B gene or a polynucleotide encoding said gRNA. Preferably, said gRNA is used in combination with Cas9 or a polynucleotide encoding Cas9. This system is used in order to reduce, preferably eliminate, METTL21B gene expression or to reduce, preferably eliminate, METTL21B histone methyltransferase activity.

In embodiment C6, said cancer is selected from the group consisting of prostate cancer, breast cancer, osteosarcoma, liposarcoma and leukemia. It is noted that the lung cancer may be non-small cell lung cancer.

DESCRIPTION OF THE FIGURES

FIG. 1 C21orf127/TRMT112 methylates histone H4 at K12. (A to C) Methylation assays. (A) Histone H4, H3, H2A, H2B, and H1 were incubated with SAM[$^3$H] in the absence or presence of recombinant C21orf127/TRMT112. (B) Wild-type or mutant histone H4 were incubated with SAM[3H] in the presence of recombinant C21orf127/TRMT112. Proteins were stained by Ponceau red. Histone H4 methylation was revealed by autoradiography. (C) Histone H4 was incubated with C21orf127/TRMT112, SAM [$^3$H], and the SAM competitive inhibitor sinefungin as indicated. Proteins were stained by Ponceau red. Histone H4 methylation was revealed by autoradiography. (D) Ribbon representation of C21orf127 (grey) TRMT112 (cyan) in complex with H4 aa11-15 K12me1 and SAH. The H4 aa11-15K12me1 peptide (yellow) and SAH (magenta) are represented as stick models.

Figure 2:
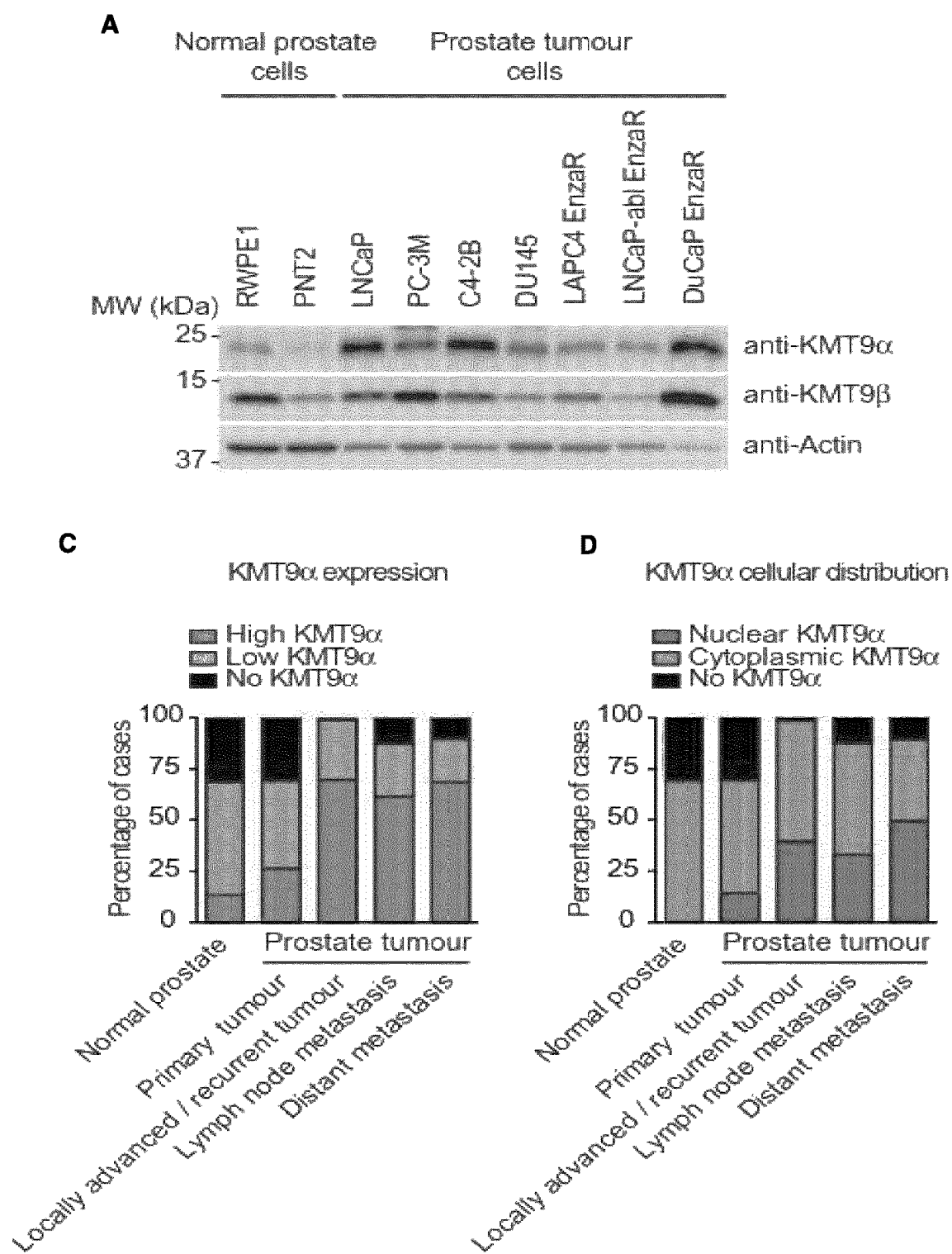

FIG. 2. KMT9 methylates H4K12 in vivo. (A) Expression of KMT9α, and KMT9β in human immortalized normal prostate cells, androgen-dependent, castration-resistant, or enzalutamide-resistant (EnzaR) prostate tumour cells was analysed by Western blotting with the indicated antibodies. (B) Representative immunohistochemical staining of KMT9α, and H4K12me1 in human normal prostate and prostate tumour. Scale bar, 100 μm. (C, D) Bar graphs displaying percentage of human normal prostate samples (n=25), primary prostate tumours (n=305), locally advanced/recurrent prostate tumours (n=81), lymph node metastases (n=31), and distant metastases (n=104) with no, low, high (C), or nuclear, cytoplasmic, or no KMT9α (D) immunohistochemical staining. (E) Levels of H4K12me1 in PC-3M cells treated with siCtrl or siKMT9α were analysed by Western blotting using the indicated antibodies and by LC-MS/MS. Proteins from lysates of PC-3M cells treated with siCtrl or siKMT9α were separated by SDS-PAGE and visualised by Coomassie blue staining. Subsequently, histone H4 was isolated, propionylated, and digested with trypsin. The resulting H4 aa4-17 peptides were then selected for targeted MS/MS analysis. Incorporation of a methyl group at K12 of H4 aa4-17 is shown for fragments y6, y7, and y9 (y6+_Me, y7+_Me, y9+_Me) demonstrating H4K12 monomethylation. m/z=mass-to-charge ratio; z=charge state calculation based on the observed isotope distribution. The fraction of H4 aa4-17 peptides monomethylated at K12 in PC-3M cells treated with siCtrl or siKMT9α was calculated by averaging the selected reaction monitoring (SRM) quantifications for all three transitions (n=5). Data represent means+s.d.; ***$p<0.001$ by two-tailed Student's test.

FIG. 3. KMT9α controls prostate cancer cell proliferation. (A) Cell cycle phase distribution assessed by propidium iodide (PI) staining and flow cytometry. Bar graphs representing percentage of cells per cell cycle phase in PC-3M cells treated with siCtrl or siKMT9α. Data represent means+s.e.m.; *$p<0.05$ by two-tailed Student's test; n=3. (B) Apoptosis assay. Apoptotic PC-3M cells treated with siCtrl or siKMT9α were identified by flow cytometry using AnnexinV and PI staining. Data represent means+s.e.m.; *$p<0.05$ by two-tailed Student's test; n=3. (C-F) Proliferation of PC-3M (C), LNCaP (D), LAPC4 (E), and LAPC4 EnzaR (F) cells transfected with siCtrl or siKMT9α as indicated. Western blot analyses were performed with the indicated antibodies to verify knockdown of KMT9α, and decreased H4K12me1 levels (C-F). Data represent means±s.d.; *$p<0.001$ by two-tailed Student's test; n=4. (G) Proliferation of LNCaP cells transfected with siCtrl or siRNA that targets the three-prime untranslated region of the endogenously transcribed KMT9α mRNA (siKMT9α-3'UTR) and infected with lentivirus driving expression of either LacZ, KMT9α, KMT9α(N122A), or KMT9α (Y125A) as indicated. n.s.: not significant. Data represent means±s.d (left panel) or means+s.d (right panel); *$p<0.001$ by two-tailed Student's test; n=4. (H-K) Proliferation of C4-2B (H), LNCaP-abl (I), LNCaP-abl EnzaR (J), and DuCaP EnzaR (K) cells transfected with siCtrl or siKMT9α as indicated. Western blot analyses were performed with the indicated antibodies to verify knockdown of KMT9α, and decreased H4K12me1 levels (H-K). Data represent means±s.d.; ***$p<0.001$ by two-tailed Student's test; n=4. (L) Proliferation of MCF10A cells that do not express KMT9α, is not affected by treatment with siKMT9α. To verify absence of KMT9α, Western blot analyses were performed using the indicated antibodies. Data represent means±s.d. n=4.

Figure 4:
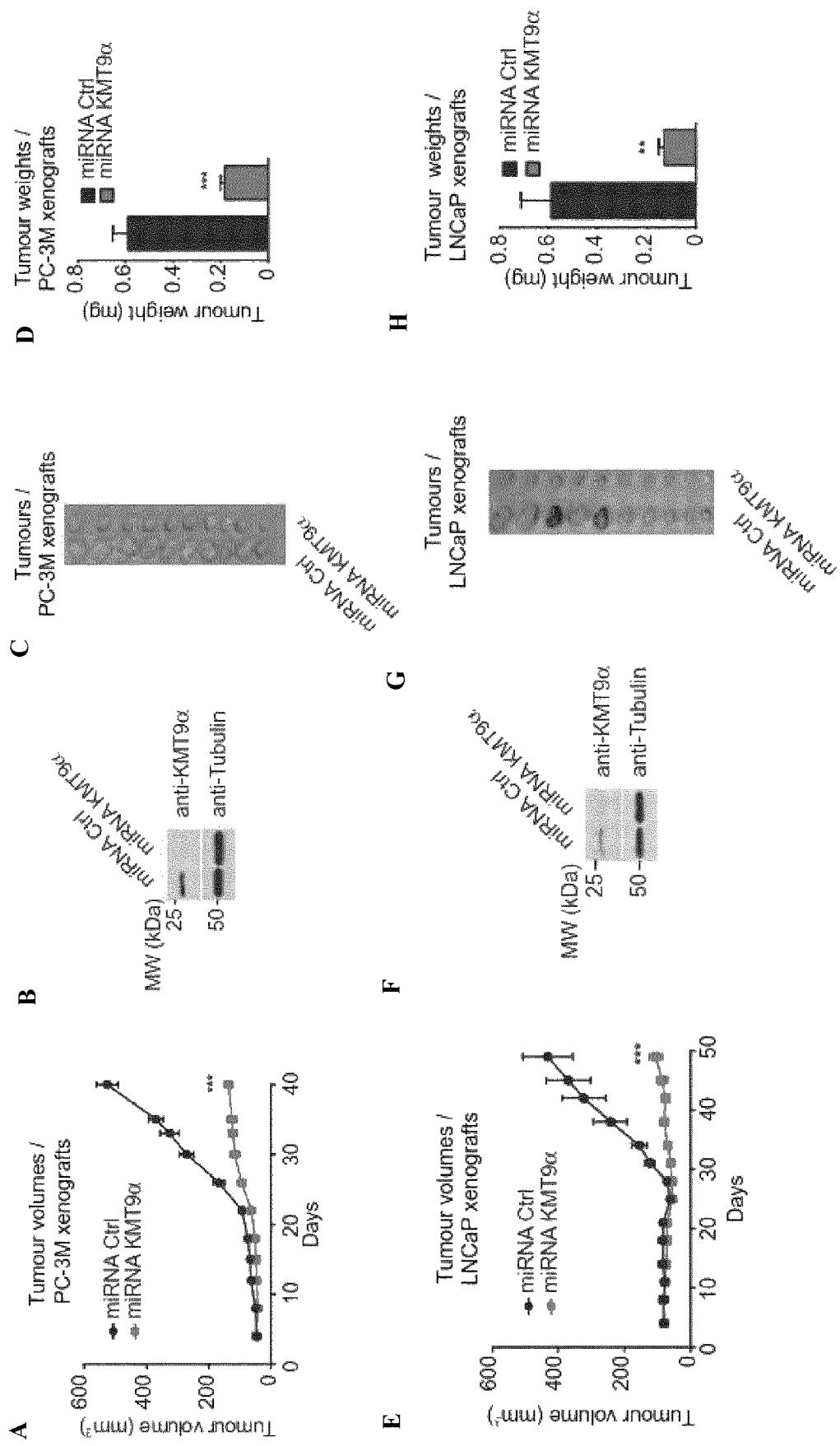

FIG. 4. KMT9α, controls growth of prostate tumour xenografts. (A) PC-3M cells were infected with lentiviruses driving expression of either miRNA (miRNA Ctrl) or a miRNA against KMT9α (miRNA KMT9α). The size of PC-3M xenograft tumours was measured over time. (B) Western blot analysis performed with the indicated antibodies to verify knockdown of KMT9α, in PC-3M cells. (C) Representation of PC-3M xenograft tumours isolated from individual animals at day 40. (D) Tumour weight of PC-3M xenografts at day 40. Data represent means±s.e.m (A) and mean+s.e.m (D), *$p<0.001$ by two-tailed Student's test. (n=10 mice). (E-H) Characterisation of LNCaP xenograft tumours. (E) LNCaP cells were infected with lentiviruses driving expression of either miRNA Ctrl or a miRNA against KMT9α. Growth of LNCaP xenograft tumours was measured over time. (F) Western blot analysis using the indicated antibodies verified depletion of KMT9α in LNCaP cells. (G) Representation of LNCaP xenograft tumours isolated from individual animals at day 50. (H) Tumour weight of LNCaP xenografts at day 50. Data represent means±s.e.m (E) and mean+s.e.m (H), $p<0.01$, *$p<0.001$ by two-tailed Student's test. (n=10 mice). (I-L) Characterisation of LAPC4 EnzaR xenograft tumours. (I) LAPC4 EnzaR cells were infected with lentivirus driving expression of either miRNA Ctrl or a miRNA against KMT9α. Growth of LAPC4 EnzaR xenograft tumours was measured over time. (J) Western blot analysis using the indicated antibodies verified depletion of KMT9α in LAPC4 EnzaR cells. (K) Representation of LAPC4 EnzaR xenograft tumours isolated from individual animals at day 48. (L) Tumour weight of LAPC4 EnzaR xenografts at day 48. Data represent means±s.e.m (I) and mean+s.e.m (L), $p<0.01$, ***$p<0.001$, by two-tailed Student's test. (n=7 mice).

FIG. 5. N6AMT1 (KMT9α) controls proliferation of breast cancer cells, ovarian carcinoma cells, colon carcinoma cells and glioblastoma cells. (A-D) Cell proliferation assays. Breast cancer cells as indicated (SK-BR3, MCF-7, MDA-MB-231, or T47-D) (A); Ovarian carcinoma cells (OVCAR-3) (B); colon carcinoma cells (SW480) (C); and glioblastoma cells (U-251MG or T98G) (D); were transfected with siRNA Ctrl or siRNA against N6AMT1 as indicated. Data represent means s.e.m.

Figure 6:
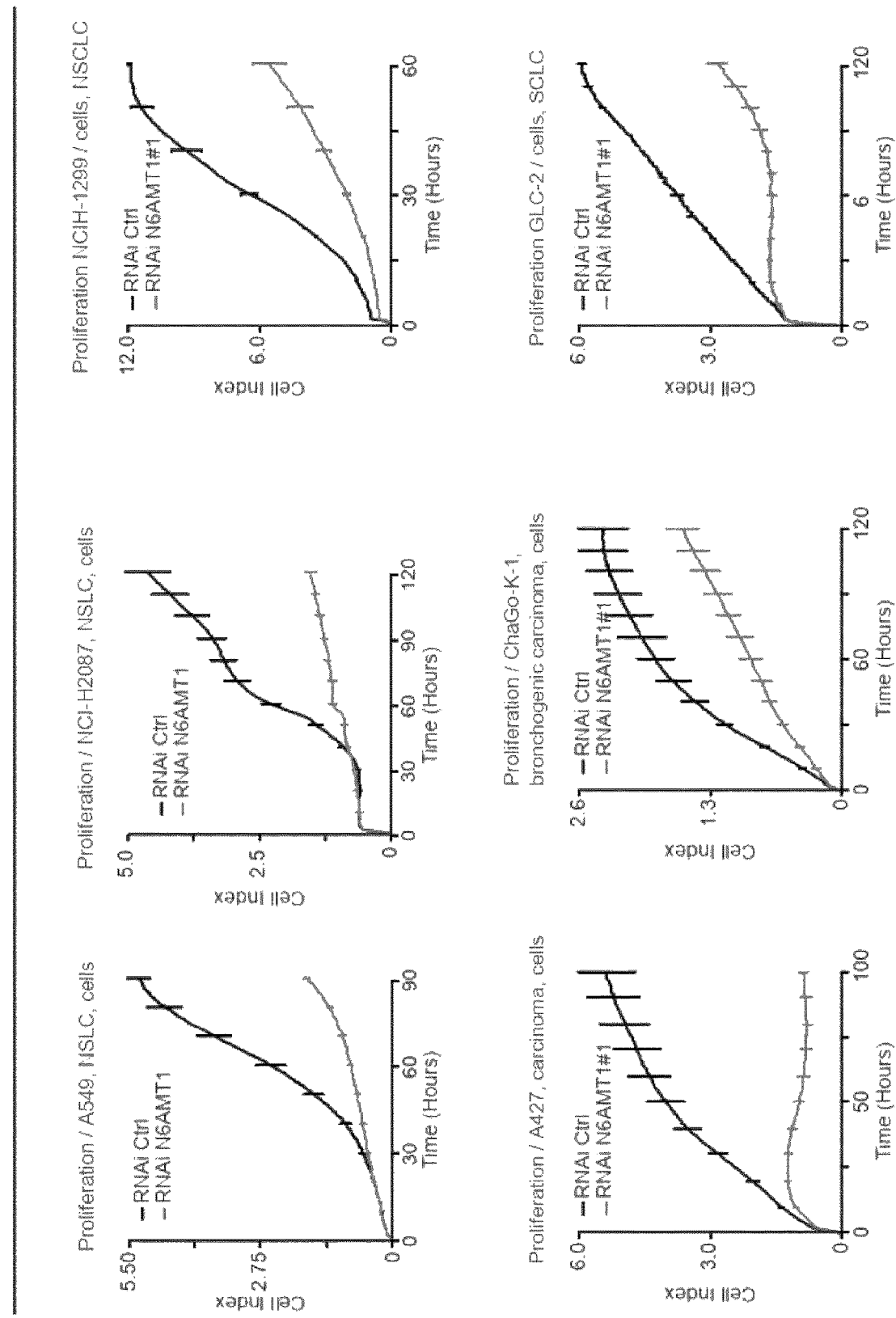
Figure 6:
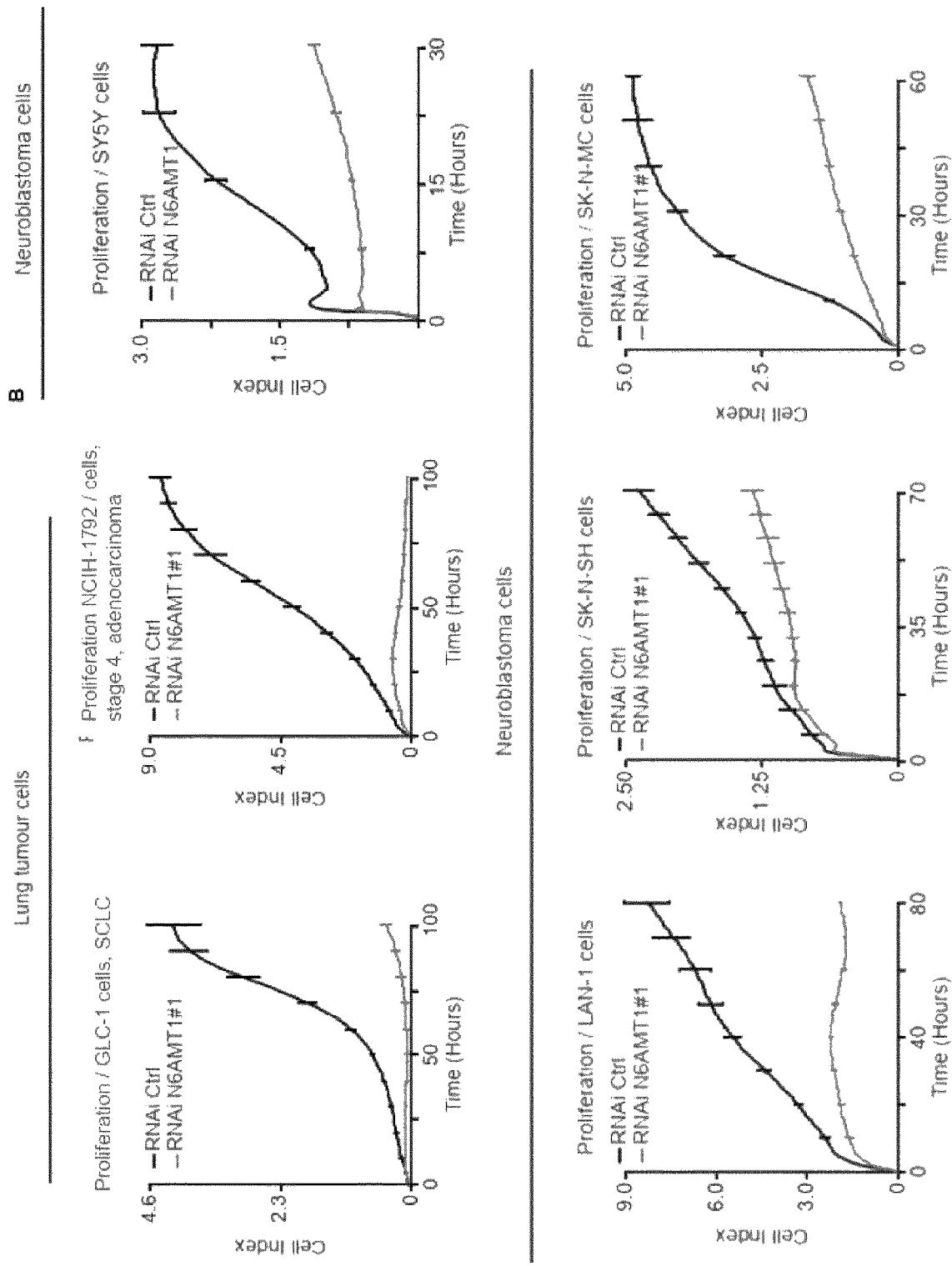

FIG. 6. N6AMT1 (KMT9α) controls proliferation of lung cancer cells and neuroblastoma cells. (A, B) Cell proliferation assays. Lung tumour cells (A549, NCI-H2087, NCIH-1299, A427, ChaGO-K-1, GLC-2, GLC-1, or NCIH-1792) (A) and neuroblastoma cells (SYSY, LAN-1, SK-N-SH, or SK-N-MC) (B) were transfected with siRNA Ctrl or siRNA against N6AMT1 as indicated. Data represent means s.e.m.

Figure 7:
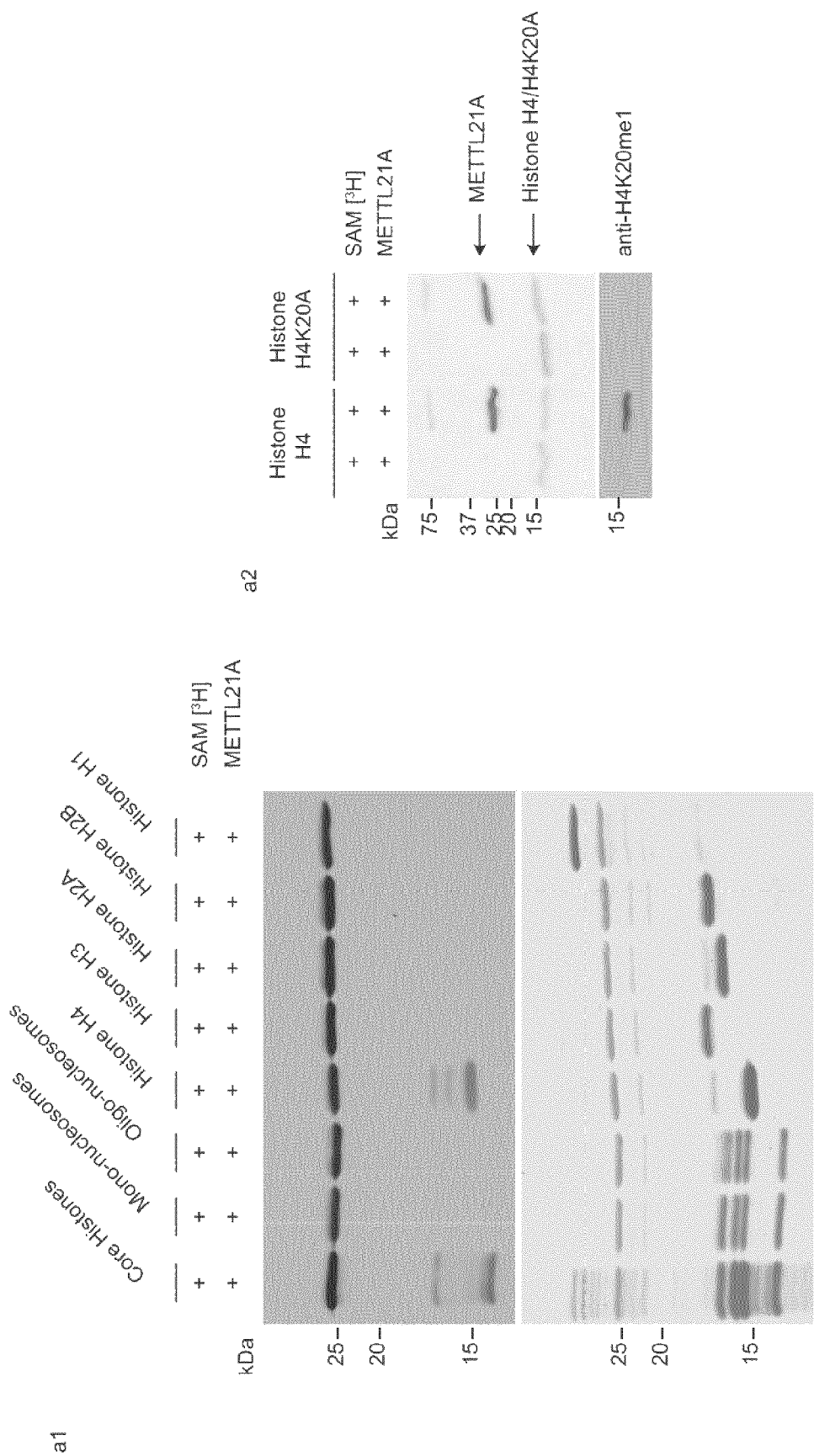

FIG. 7. METTL21A is a novel histone methyltransferase that controls proliferation of tumour cells. METTL21A methylates histones, namely histone H4 at K20 (a1 and a2) and controls proliferation of tumour cells (b-f). Lung tumour cells (A549, NCIH-292 or GLC2) (b), prostate tumour cells (DU145 or PC-3M-luc2) (c), neuroblastoma cells (Sy5y or SK-N-MC) (d), glioblastoma cells (LN229 or A172) (e), and breast tumour cells (MDA-MB-231) (f) were transfected with siRNA Ctrl or siRNA against METTL21A as indicated. Data represent means s.e.m.

Figure 8:
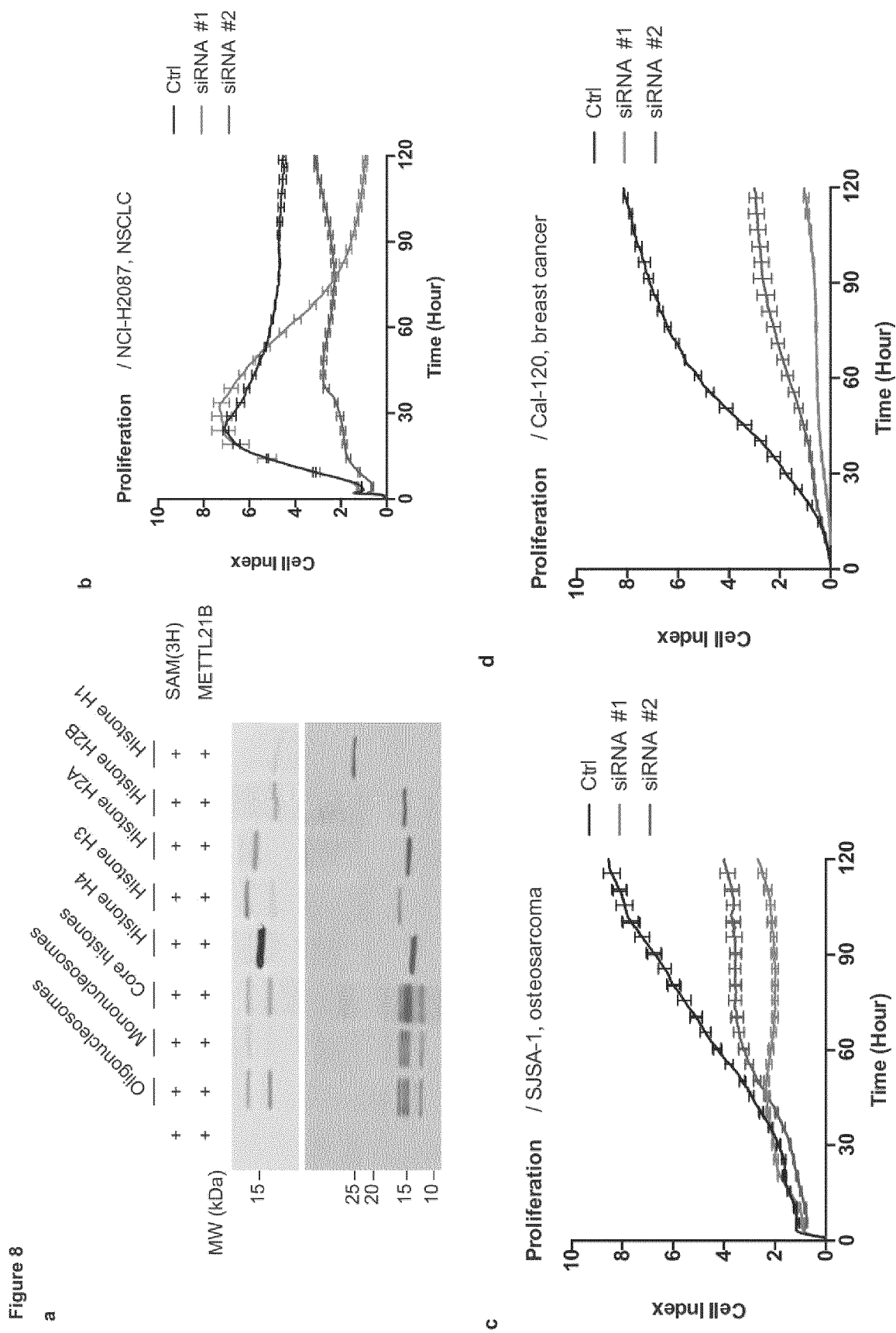

FIG. 8. METTTL21B is a novel histone methyltransferase that controls proliferation and migration of tumour cells. METTL21B methylates histones (a) and controls proliferation (b-g) and migration (h-j) of tumour cells. Proliferation:

lung tumour cells (NCI-H2087) (b), osteosarcoma (SJSA-1) (c), breast cancer (Cal-120, Hs578T or JIMT-1) (d, f, g), and liposarcoma cells (T778) (e) were transfected with siRNA Ctrl or siRNA against METTL21B as indicated. Data represent means±s.e.m. Migration: breast tumour cells (JIMT-1, Cal-120) (i, j) and osteosarcoma (SJSA-1) (h) were transfected with siRNA Ctrl or siRNA against METTL21B as indicated. Data represent means±s.e.m. (k) RNAi mediated knockdown of METTL21B was verified by Western blot using the indicated antibodies.

Figure 9:
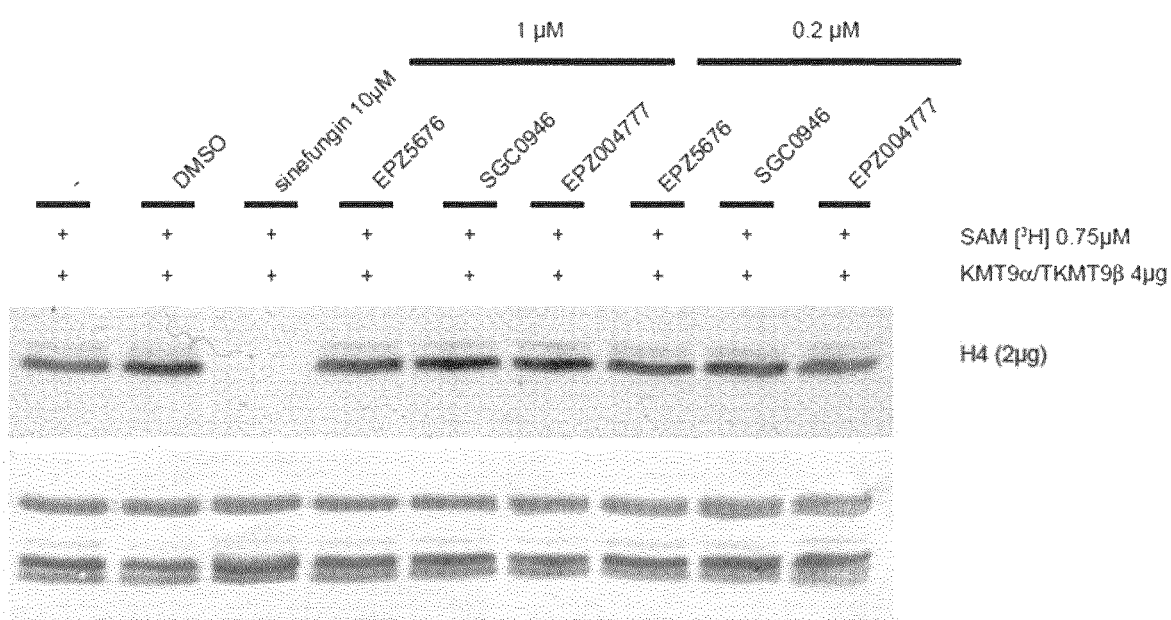

FIG. 9. The DOT1L inhibitors EPZ2676, SGC0946 and EPZ004777 do not inhibit the HMT activity of KMT9. Histone H4 (2 µg) was incubated with SAM[3H] in the presence of recombinant KMT9 (KMT9α and KMT9β) and the three afore-mentioned inhibitors as indicated. Sinefungin was used as positive control and histone H4 methylation was revealed by autoradiography. The bottom row shows Ponceau staining of the gel.

FIG. 10. METTL21A controls proliferation and H4K20me1 levels in DU145 and A549 cells (A, B). Cellular distribution of METTL21A was assessed by Western blot analysis (WCE: Whole Cell Extract, CE: Cytosolic Extract; NE: Nuclear Extract). Western blots were decorated with the indicated antibodies. Data represent means s.e.m.

FIG. 11. Expression levels of KMT9α (a) and KMT9β (b) in 286 tissue samples from CRC patients and 41 samples from human healthy colon or rectum as control. Expression levels are given in transcripts per million (TPM). The raw RNA-seq data was provided by Chandrashekar et al. (2017) UALCAN: A portal for facilitating tumor subgroup gene expression and survival analyses. Neoplasia 19, 649-658. Western blots of whole cell lysates from CRC cell lines were decorated with the indicated antibodies (c). KMT9α is localized in the nucleus and cytosol in human CRC cells (d) and in human CRC tissue samples (e). Localization of KMT9α, Tubulin (cytoplasmic marker protein) and Lamin A (nuclear marker protein) was analyzed by Western blotting using the indicated antibodies. Representative immunohistochemical staining of KMT9α in human colorectal cancer. Scale bar, 50 µm. Nuclei were stained by hematoxylin (e).

Figure 12:
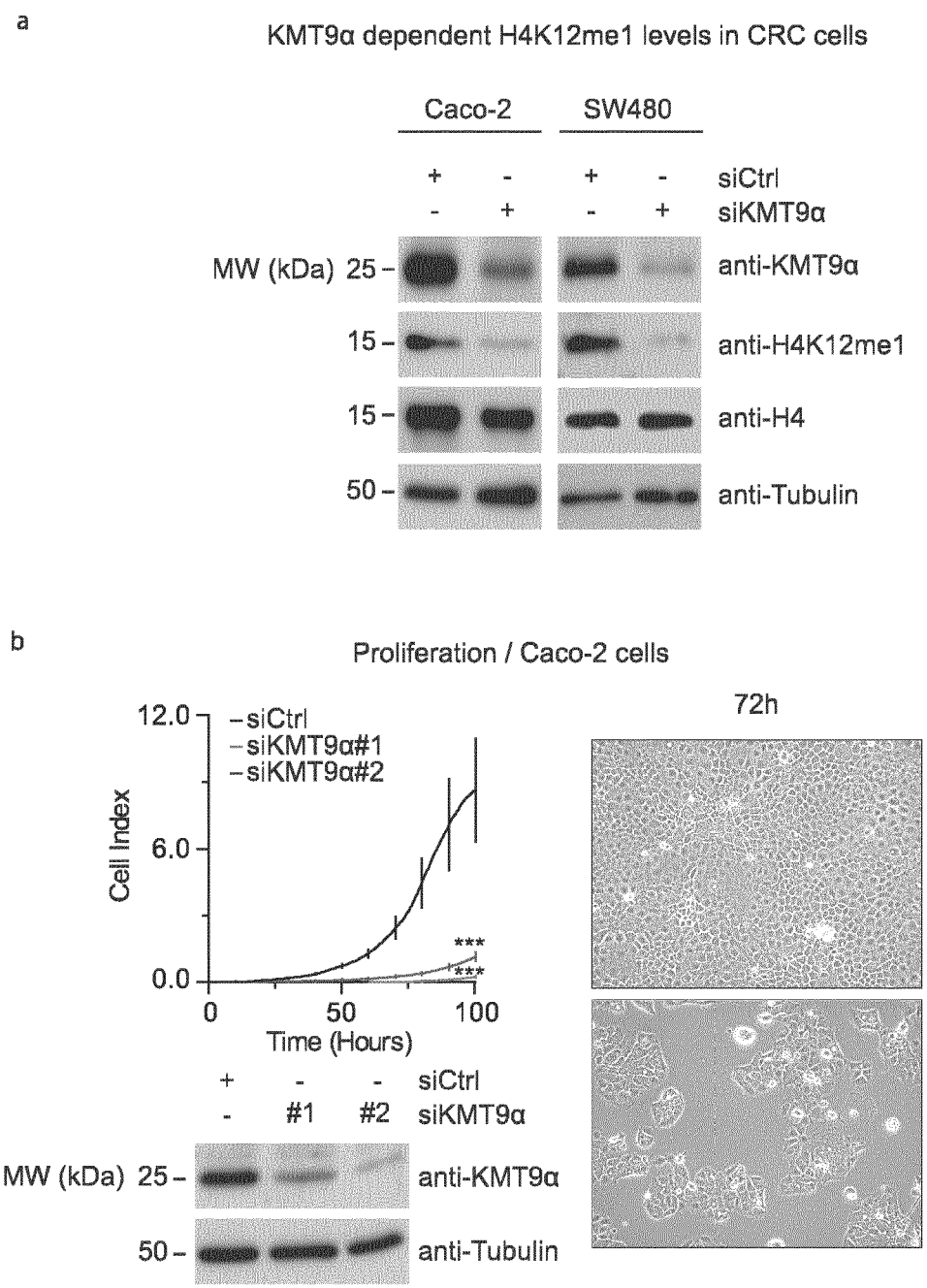

FIG. 12. KMT9α methylates H4K12 in CRC cell lines. Western blots were decorated with the indicated antibodies. Samples obtained from SW480 and Caco-2 cells transfected with siRNA control (Ctrl) or siRNA against KMT9α (a). KMT9α controls proliferation of CRC cells. Proliferation of Caco-2 (b) and SW480 (c) human CRC cells transfected with siRNA control (Ctrl) or siRNA against KMT9α was analyzed in real-time (xCelligence). Western blots were decorated with the indicated antibodies. Representative images of Caco-2 (b) and SW480 (c) are shown.

Figure 13:
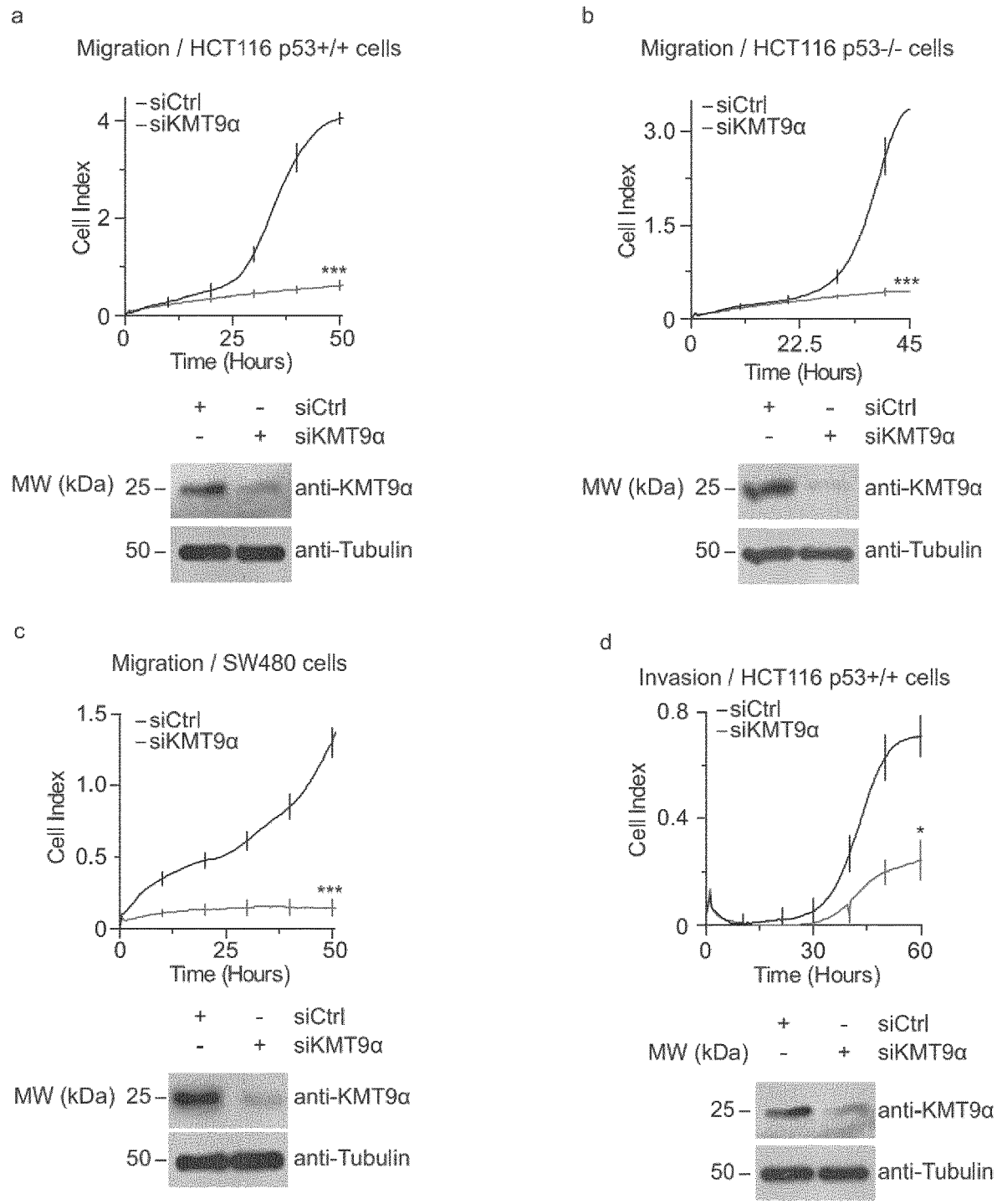

FIG. 13. KMT9α controls migration of CRC cells. Migration of HCT116 p53+/+ (a), HCT116 p53−/− (b) and SW480 (c) human CRC cells transfected with siRNA control (Ctrl) or siRNA against KMT9α was analyzed in real-time (xCelligence). Western blots were decorated with the indicated antibodies. KMT9α controls invasion of CRC cells (d, e). Invasion of HCT116 p53+/+ (d), HCT116 p53−/− (e) human CRC cells transfected with siRNA control (Ctrl) or siRNA against KMT9α was analyzed in real-time (xCelligence). Western blots were decorated with the indicated antibodies.

FIG. 14. KMT9α controls growth of AOM/DSS colorectal tumor organoids. Outline of the experimental design (a). Representative light images display KMT9α dependent growth of tumor organoid (b). Quantification of tumor organoid size (c). Tamoxifen-induced loss of KMT9α expression in tumor organoid was verified by qRT-PCR (d). KMT9α controls proliferation of human CRC organoids (e and f). Quantification of patient-derived human CRC organoid growth upon lentiviral transduction of control miRNA (miCtrl) or miRNA against KMT9α (miKMT9α) (e). Verification of KMT9α-knockdown by qRT-PCR (f).

Figure 15:
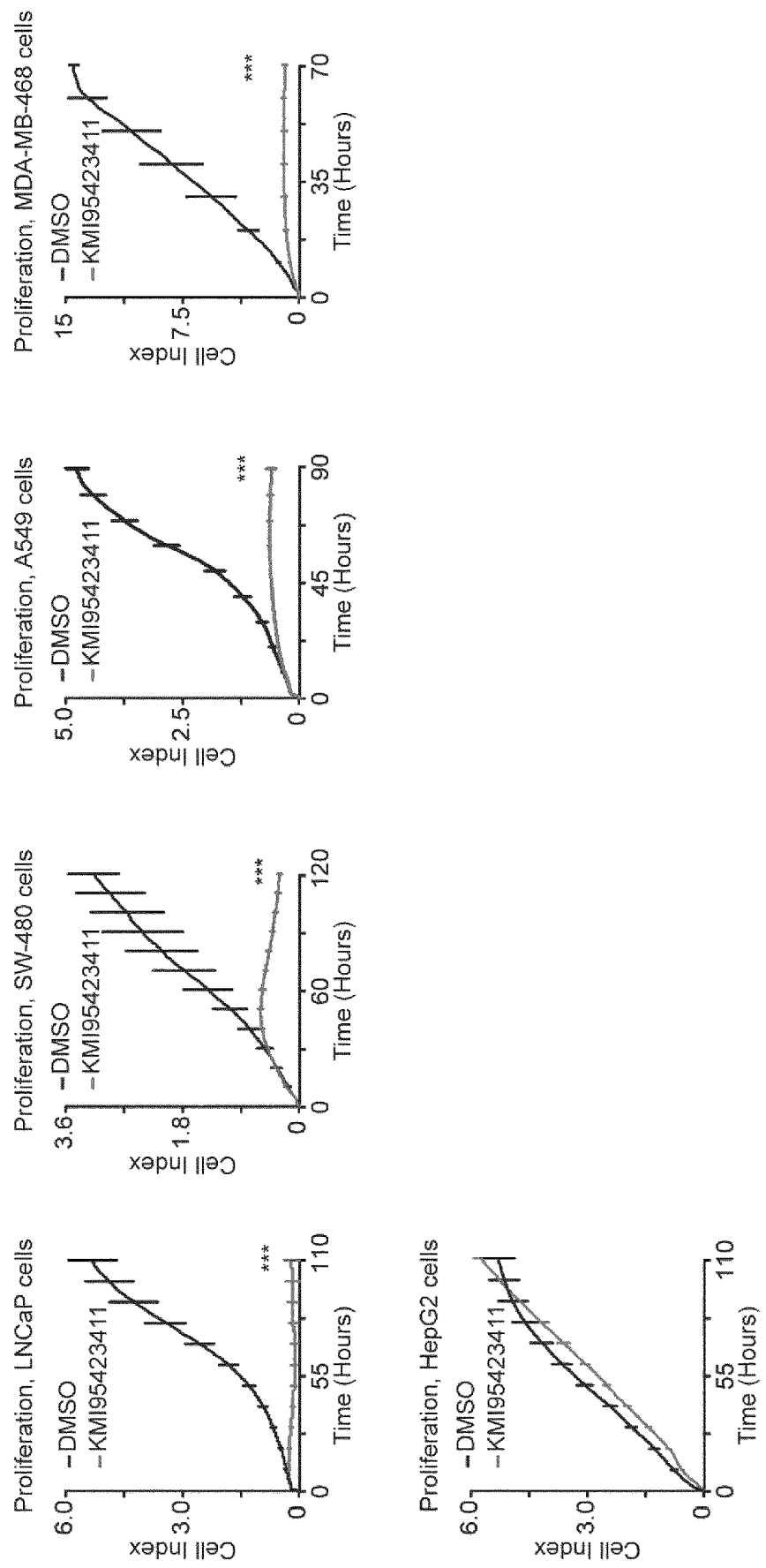

FIG. 15. A small molecule inhibitor of KMT9 blocks proliferation of LNCaP prostate tumour cells, SW-480 colorectal cancer cells, MDA-MB-468 breast cancer cells, and A549 lung tumour cells, while it does not affect proliferation of the KMT9 non-responsive HepG2 cells (compound "KMI95423411" is also referred to as compound 75b in the present application).

DETAILED DESCRIPTION OF THE INVENTION

Before the present invention is described in more detail in the example section, the underlying findings are described and definitions are introduced.

1. UNDERLYING FINDINGS AND DEFINITIONS

The present invention is based on the finding that there exist further, thus far unknown histone lysine methyltransferases (HMTs) in the protein family of seven-β-strand proteins. Up to now, only a single member of this protein family has been shown to possess HMT-activity, namely DOT1L. The inventors were able to characterize three novel HMTs, namely KMT9 formed by the assembly of KMT9alpha and KMT9beta, METTL21-A and METTL21-B. Moreover, the inventors found that inhibition of the afore-mentioned three HMTs can be used to treat cancer.

The Novel HMT KMT9 (KMT9alpha KMT9beta Heterodimer)

The data gained for KMT9 show that this enzyme selectively methylates histone H4 at lysine 12 (K12) in the form of a mono-methylation. The inventors found that KMT9 is expressed in normal prostate cells as well as in prostate cancer cells and various other cancer cells including breast cancer, ovarian cancer, colon cancer, colorectal cancer, glioblastoma, lung cancer, neuroblastoma, osteosarcoma and liposarcoma cells. KMT9 regulates gene expression of a variety of genes, wherein most of these genes are involved in the cell cycle. Using selective knock-down experiments, the inventors found that cell cycle progression is severely affected. The effect of KMT9 inhibition on the proliferation of cells was then investigated in various cancer cells with the result that proliferation of various cancer cells was severely affected upon inhibition of KMT9. This was confirmed in xenograft models using different prostate tumors in mice and in organoid culture of colorectal cancer.

The inventors were able to establish a direct link from the enzymatic activity of KMT9, namely the HMT-activity, to cell proliferation, i.e. active KMT9 results in cell proliferation. If (i) the heterodimer of KMT9alpha/KMT9beta is not formed at all in the cells (tested e.g. via an RNAi knock-down specific for KMT9alpha), (ii) KMT9alpha/KMT9beta is only present in the cells in the form of an enzymatically inactive form (tested via specific knock-down of KMT9alpha and complementation with a mutant KMT9alpha form (N122A) or tested in an in vitro assay with a recombination mutant protein (N122A) of KMT9alpha), or (iii) KMT9 is inhibited via a compound (tested with KMT9-inhibitors as well as the compound sinefungin), KMT9 is unable to exhibit its positive effect on cell proliferation. As shown by the inventors, the proliferation of various cancer cells can be blocked by inhibiting the expression of KMT9alpha or KMT9beta or the enzymatic activity of KMT9.

Therefore, the present application for the first time provides the proof-of-concept that KMT9 inhibition can be used to treat cancer.

The above finding opens up a completely new field for drugs that can be used to treat cancer, namely drugs that selectively inhibit KMT9.

As for each drug acting via inhibition of an enzyme, it is of course the goal to inhibit the respective enzyme, here KMT9, very selectively, in the meaning that a different enzyme—be it related (such as DOT1L) or unrelated—is substantially not affected by the inhibition. A main reason is that any off-target effects shall be substantially excluded.

The terms "selective", "selectively" and "selectivity" are used herein for the inhibition in the meaning that the respective inhibitor is more selective for KMT9 compared to a different enzyme, particularly a different HMT, most particularly to DOT1L as the closest HMT-member of this protein family.

For this reason, the present application is only directed to KMT9 inhibitors that selectively inhibit KMT9, wherein the selectivity is at least a selectivity that is higher when compared to DOT1L inhibition. In other words, the KMT9 inhibitor of the present invention is more selective for KMT9 compared to DOT1L as the closest characterized member of this protein family.

It is obvious that the selectivity depends on the type of inhibitor that is used to inhibit KMT9.

If an inhibitor from an RNA interference system (in particular a siRNA) or an inhibitor from the CRISPR-Cas system (using inter alia in particular a gRNA) is used, this inhibitor is selective already as a result from its design, namely in that such an inhibitor is sequence-specific for the sequence of KMT9alpha and/or KMT9beta (on RNA and DNA level, respectively). The data of the present application nicely show this for siRNA directed to KMT9alpha and to KMT9beta.

The same applies to an antibody directed to KMT9alpha and/or KMT9beta since the antibody is raised and designed such that it binds selectively to KMT9 composed of KMT9alpha/KMT9beta or KMT9alpha or KMT9beta. The CHIP-seq data of the present application nicely shows the specificity of the antibody used therein e.g. for KMT9alpha.

When it comes to compounds specific for KMT9, the present application provides data that a small molecule is capable of inhibiting KMT9 and is moreover selective for KMT9 (see compound 72b described in the example section). Moreover, the present application provides data that a small molecule inhibiting KMT9 (see compound 75b described in the example section), which is added to cancer cells grown in cell culture, is capable of blocking the proliferation of these cancer cells. Accordingly, the present application provides support for "a small molecule selective for KMT9-inhibition" that can be used to treat cancer. It is noted that e.g. sinefungin does not correspond to a specific inhibitor according to the present invention since it is classified as non-selective protein methyl transferase inhibitor [see in particular Table 3 of Copeland, R. et al., Protein methyltransferases as a target class for drug discovery. Nature 8, 724-732 (2009)]. The same applies to S-adenosyl-L-homocysteine (referred to herein also as "SAH"), see also the afore-mentioned table. Another non-selective inhibitor is 3-Deazaneplanocin A. Such inhibitors generally inhibit a class of enzymes by their mode of inhibition but are not regarded as selective inhibitors according to the present invention. The data using sinefungin as provided herein have been gained to further illustrate that inhibition of KMT9 by a compound is generally possible and will result in a cell proliferation stop of cancer cells, i.e. it is proof-of-concept data. That compounds are generally capable of being selective between close homologs, in the present case between KMT9 and DOT1L, can be derived from the data shown herein for compound 72b, which is a strong inhibitor of KMT9 but of no other methyltransferase of a plurality of methyltransferases including DOT1L. Furthermore, it can already be derived from the unsuccessful inhibition of KMT9 by three compounds that successfully inhibit DOT1L, namely EPZ5676, SGC0946 and EPZ004777 (see example 7 and FIG. 9). In order to identify compounds that fulfill the selectivity-requirement as outlined above, such compounds can easily be tested for their selectivity towards KMT9 by testing their inhibitory potential against KMT9 compared to DOT1L. A typical assay in this respect is carried out as follows:

(1) Four µg of purified recombinant KMT9 (provided in the form of the heterodimer, e.g. as His-KMT9alpha/KMT9beta) are incubated with 2 µg of histones H4 in methylation buffer (10 mM Tris-HCl pH 7.6, 50 mM KCl, 10 mM Mg(OAc)2, 1 mM DTT) (a) in the absence of the inhibitor and (b) in the presence of the inhibitor at 1 µM (b1) and 0.2 µM (b2), and incubated for 20 minutes at room temperature. Subsequently, 1.5 µl of radioactively labelled [3H]SAM are added, and the reaction is incubated for 60 min at 30° C. The reaction mixture is then analysed by autoradiography and Ponceau red staining, and the %-inhibition is determined by compared the concentration-dependent inhibition observed at (b1) and (b2) to the positive control without any inhibition [(a) above].

(2) In parallel, four µg of purified recombinant DOT1L are incubated with 2 µg of histones H3 in methylation buffer (10 mM Tris-HCl pH 7.6, 50 mM KCl, 10 mM Mg(OAc)2, 1 mM DTT) (a) in the absence of the inhibitor and (b) in the presence of the same inhibitor at 1 µM (b1) and 0.2 µM (b2), and incubated for 20 minutes at room temperature. Subsequently, 1.5 µl of radioactively labelled [3H]SAM are added, and the reaction is incubated for 60 min at 30° C. The reaction mixture is then analysed by autoradiography and Ponceau red staining, and the %-inhibition is determined by compared the concentration-dependent inhibition observed at (b1) and (b2) to the positive control without any inhibition [(a) above].

(3) Finally, the %-inhibition is compared between the KMT9-assay and the DOT1L-assay, wherein the inhibitor is more selective for KMT9-inhibition if the %-inhibition is higher for KMT9 than for DOT1L.

When it comes to inhibitors of KMT9 on a general level, the present application for the first time provides proof-of-concept evidence that, by inhibiting KMT9, cancer can be treated, and this concept is reflected in some of the claims. When it comes to inhibitory small molecules, the respective supportive data is provided herein by using two exemplary compounds acting as KMT9 inhibitors—such small molecules may of course be the subject of patent applications, and claims directed to such small molecules would only be dependent on the present application when it comes to the use of such compounds for the treatment of cancer.

The novel HMTs METTL21A and METTL21B

What has been outlined above for KMT9 is also applicable for the other two newly identified HMTs METTL21A and METTL21B. The present application for the first time provides the proof-of-concept data that METTL21A or METTL21B inhibition can be used to treat cancer.

The above findings open up a completely new field for drugs that can be used to treat cancer, namely drugs that selectively inhibit either METTL21A or METTL21B.

As for each drug acting via inhibition of an enzyme, it is of course the goal to inhibit the respective enzyme, here METTL21A or METLL21B, very selectively, in the meaning that a different enzyme—be it related (such as DOT1L) or unrelated—is substantially not affected by the inhibition. The reason is that any off-target effects shall be substantially excluded.

Thus, the terms "selectively" and "selectivity" are used herein for the inhibition in the meaning that the respective inhibitor is more selective for METTL21A compared to a different enzyme, particularly a different HMT, most particularly to DOT1L as the closest HMT-member of this protein family. The same applies for METTL21B: The terms "selectively" and "selectivity" are used herein for the inhibition in the meaning that the respective inhibitor is more selective for METTL21B compared to a different enzyme, particularly a different HMT, most particularly to DOT1L as the closest HMT-member of this protein family.

Corresponding assays may be carried out as follows:

(1) Four µg of purified recombinant His-METTL21A or His-METTL21B are incubated with 2 µg of histones H4 (for His-METTL21A) or H3 (for His-METTL21B) in methylation buffer (10 mM Tris-HCl pH 7.6, 50 mM KCl, 10 mM Mg(OAc)2, 1 mM DTT) (a) in the absence of the inhibitor and (b) in the presence of the inhibitor at 1 µM (b1) and 0.2 µM (b2), and incubated for 20 minutes at room temperature. Subsequently, 1.5 µl of radioactively labelled [3H]SAM are added, and the reaction is incubated for 5 h (METTL21A) or 18 h (METTL21B) at 30° C. The reaction mixture is then analysed by autoradiography and Ponceau red staining, and the %-inhibition is determined by compared the concentration-dependent inhibition observed at (b1) and (b2) to the positive control without any inhibition [(a) above].

(2) In parallel, four µg of purified recombinant DOT1L are incubated with 2 µg of histones H3 in methylation buffer (10 mM Tris-HCl pH 7.6, 50 mM KCl, 10 mM Mg(OAc)2, 1 mM DTT) (a) in the absence of the same inhibitor and (b) in the presence of the same inhibitor at 1 µM (b1) and 0.2 µM (b2), and incubated for 20 minutes at room temperature. Subsequently, 1.5 µl of radioactively labelled [3H]SAM are added, and the reaction is incubated for 60 min at 30° C. The reaction mixture is then analysed by autoradiography and Ponceau (3) red staining, and the %-inhibition is determined by compared the concentration-dependent inhibition observed at (b1) and (b2) to the positive control without any inhibition [(a) above].

(4) Finally, the %-inhibition is compared between the METTL21A- or METTL21B-assay, respectively, and DOT1L-assay, wherein the inhibitor is more selective for METTL21A-inhibition or METTL21B-inhibition, respectively, if the %-inhibition is higher for METTL21A or METTL21B than for DOT1L.

For this reason, the present application is only directed to METTL21A inhibitors that selectively inhibit METTL21A, wherein the selectivity is at least a selectivity that is higher when compared to DOT1L inhibition. In other words, the METTL21A inhibitor of the present invention is more selective for METTL21A compared to DOT1L as the closest characterized member of this protein family. Further, the present application is only directed to METTL21B inhibitors that selectively inhibit METTL21B, wherein the selectivity is at least a selectivity that is higher when compared to DOT1L inhibition. In other words, the METTL21B inhibitor of the present invention is more selective for METTL21B compared to DOT1L as the closest characterized member of this protein family.

In view of the above, the term "inhibitor" as used herein always refers to an inhibitor that is selective for the respective HMT, i.e. either selective for KMT9, METTL21A or METTL21B.

As used in the specification and the claims, the singular forms of "a" and "an" also include the corresponding plurals unless the context clearly dictates otherwise.

The term "about" in the context of the present invention denotes an interval of accuracy that a person skilled in the art will understand to still ensure the technical effect of the feature in question. The term typically indicates a deviation from the indicated numerical value of 10% and preferably ±5%.

It needs to be understood that the term "comprising" is not limiting. For the purposes of the present invention, the term "consisting of" is considered to be a preferred embodiment of the term "comprising". If hereinafter a group is defined to comprise at least a certain number of embodiments, this is also meant to encompass a group which preferably consists of these embodiments only.

The term "KMT9alpha" as used herein refers to the protein "N-6 adenine-specific DNA methyltransferase 1" [*Homo sapiens* (human)], with the underlying Gene ID: 29104 (updated on 10 Sep. 2018, database: https://www.ncbi.nlm.nih.gov/gene). "N6AMT1" or "KMT9alpha" is the corresponding gene. Other names for KMT9alpha are C21orf127, Hemk2, Mtq2, N6amt1, PrmC or PRED28. The sequence of the KMT9alpha protein (isoform 1 [*Homo sapiens*]) is depicted in SEQ ID NO: 31. The term "KMT9beta" as used herein refers to the protein "tRNA methyltransferase subunit11-2" [*Homo sapiens* (human)] with the underlying Gene ID: 51504 (updated on 5 Aug. 2018, database: https://www.ncbi.nlm.nih.gov/gene). "TRMT112" or "KMT9beta" is the corresponding gene. The sequence of the KMT9beta protein (isoform 2 [*Homo sapiens*]) is depicted in SEQ ID NO: 32. The term "KMT9" means the heterodimer composed of KMT9 alpha and KMT9beta.

The term "METTL21A" as used herein refers to the protein "methyltransferase like 21A" [*Homo sapiens* (human)] with the underlying Gene ID: 151194 (updated on 5 Aug. 2018, database: https://www.ncbi.nlm.nih.gov/gene). "METTL21A" is the corresponding gene. The sequence of the METTL21A protein (isoform 1 [*Homo sapiens*]) is depicted in SEQ ID NO: 33.

The term "METTL21B" as used herein refers to the protein "EEF1A lysine methyltransferase 3" [*Homo sapiens* (human)] with the underlying Gene ID: 25895 (updated on 5 Aug. 2018, database: https://www.ncbi.nlm.nih.gov/gene). "METTL21B" is the corresponding gene. The sequence of the METTL21B protein (isoform a [*Homo sapiens*]) is depicted in SEQ ID NO: 34.

The term "DOT1L" as used herein refers to the protein "DOT1 like histone lysine methyltransferase" [*Homo sapiens* (human)] with the underlying Gene ID: 84444 (updated on 15 Sep. 2018, database: https://www.ncbi.nlm.nih.gov/gene). The sequence of the DOT1L protein [*Homo sapiens*] is depicted in SEQ ID NO: 35.

In general, the indication of "me" after the amino acid "K" (i.e. lysine) indicates that the corresponding lysine residue is methylated. The number, e.g. "2" indicates that there are two methyl-groups present at the corresponding lysine, e.g. "K27me2". Another example is "K27me3", where three methyl-groups are present at lysine 27.

The term "small molecule" as used herein refers to a small organic compound having a low molecular weight. A small molecule may be a synthetic compound not known to occur in nature or a naturally-occurring compound isolated from or known to occur in natural sources, such as e.g. cells, plants, fungi, animals and the like. A small molecule in the context of the present invention preferably has a molecular weight of less than 5000 Dalton, more preferably of less than 4000 Dalton, more preferably less than 3000 Dalton, more preferably less than 2000 Dalton or even more preferably less than 1000 Dalton. In a particularly preferred embodiment a small molecule in the context of the present invention has a molecular weight of less than 800 Dalton. In another preferred embodiment, a small molecule in the context of the present invention has a molecular weight of 50 to 3000 Dalton, preferably of 100 to 2000 Dalton, more preferably of 100 to 1500 Dalton and even more preferably of 100 to 1000 Dalton. Most preferably, a small molecule in the context of the present invention has a molecular weight of 100 to 800 Dalton.

It is further preferred that a small molecule in the context of the present invention meets the "Rule of Five" as set out below and is thus orally active (i.e. has a good oral bioavailability). These rules are as follows: (i) the small molecule has no more than five hydrogen bond donors (e.g. nitrogen or oxygen atoms with one or more hydrogen atoms); (ii) the small molecule has not more than ten hydrogen bond acceptors (e.g. nitrogen or oxygen atoms); (iii) the small molecule has a molecular mass of less than 500 Dalton; (iv) the small molecule has an octanol-water partition coefficient log P not greater than 5.

The term "small chemical fragment" is typically used in the field of drug discovery and relates to the starting pool of molecules during the process of drug discovery ("fragment-based lead discovery"), wherein a small chemical fragment that has been identified as promising binding partner may undergo structural modifications to increase the binding affinity and/or specificity.

As can be derived inter alia from the example section, the inventors found that KMT9alpha (in example 1 referred to as "C21orf127") forms a heterodimer with KMT9beta (in example 1 referred to as "TRMT112") when acting as HMT. The formation of this heterodimer has previously been described for KMT9, namely when it comes to its enzymatic activity as methylase of translation termination factor eRF1 (see Figaro et al., 2008, reference[14]). The inventors found that the interaction between KMT9alpha and KMT9beta is crucial for HMT-activity.

A "small molecule" or a "small chemical fragment" as defined above may be used to inhibit the HMT-activity of the heterodimer, e.g. by specifically inhibiting the substrate binding site of KMT9. However, a "small molecule" or a "small chemical fragment" as defined above may also be used as KMT9 inhibitor if it selectively inhibits the interaction between KMT9alpha and KMT9beta and/or disrupts the interaction between KMT9alpha and KMT9beta.

The term "inhibiting the interaction" as used herein means that preferably no interaction at all (at least not to a detectable level) between two proteins takes place any more. However, when a given interaction between two proteins (set to 100%) is greatly reduced, e.g. to a level of about 70%, about 60%, about 50%, about 40%, about 30%, preferably about 20%, more preferably about 10% or most preferably about 5% or less, such a reduced interaction is still encompassed by the term "inhibiting the interaction". In terms of the medical use of compound inhibiting an interaction, a complete inhibition of an interaction may not be required to achieve a sufficient therapeutic effect. Thus, it needs to be understood that the term "inhibiting" as used herein also refers to a reduction of an interaction, which is sufficient to achieve the desired effect.

The term "selectively inhibiting the interaction" between protein A and protein B as used herein means that the inhibition abolishes or reduces only the interaction between protein A and protein B, in the present case between KMT9alpha and KMT9beta, without e.g. affecting further interactions of KMT9alpha with other proteins and/or of KMT9beta with other proteins. This may also be referred to as "inhibiting only" a given interaction. The effect of such a "specific inhibition" is that only the desired downstream effect is affected (in the present case abolished or reduced), whereas other downstream effects mediated via different interactions still take place.

The term "antibody" as used herein preferably relates to a monoclonal or polyclonal antibody. However, the antibody may also be selected from antibody variants or fragments such as e.g. single chain antibodies, diabodies, minibodies, single chain Fv fragments (sc(Fv)), sc(Fv)$_2$ antibodies, Fab fragments, F(ab')$_2$ fragments, or tandem bodies. Antibodies may be produced according to any suitable method known to the person skilled in the art. Polyclonal antibodies may e.g. be produced by immunization of animals with the antigen of choice, whereas monoclonal antibodies of defined specificity may e.g. be produced using the hybridoma technology developed by Kohler and Milstein. It is noted that an antibody as used herein may also be functionally linked, e.g. comprise a further therapeutically active moiety or a detectable label. The term "binding fragment thereof" relates to a fragment of an antibody, wherein such a fragment is still capable of binding the antigen. Preferably, such a fragment thus still comprises the CDR-regions of the underlying antibody.

The term "siRNA" as used herein relates to an RNA molecule suitable for reducing or inhibiting the expression of the target, in the present invention either KMT9alpha and/or KMT9beta, METTL21A or METTL21B, which may be a single stranded or double stranded RNA molecule that is capable of hybridizing to either KMT9alpha and/or KMT9beta mRNA (indicated herein as "siRNA directed to KMT9alpha and/or KMT9beta mRNA") or METTL21A mRNA (indicated herein as "siRNA directed to METTL21A mRNA") or METTL21B mRNA (indicated herein as "siRNA directed to METTL21B mRNA"), thereby inducing RNA interference that results in reduction or inhibition of the expression of the target, in the present invention either KMT9alpha and/or KMT9beta, METTL21A or METTL21B. The review by Chakraborty, C. et al., Therapeutic miRNA and siRNA: Moving from Bench to Clinic as next generation medicine. *Mol Ther Nucleic Acids* 8, 123-143 (2017) gives an overview over the system RNA interference, of therapeutic applications of siRNAs and an outlook of these applications in the future.

The siRNA may be of any sequence that allows the siRNA molecule to induce RNA interference resulting in reduction or inhibition of the expression of the target, in the present invention either KMT9alpha and/or KMT9beta, METTL21A or METTL21B. Preferably, the siRNA molecule has a length of between 10 and 100, between 12 and 80, between 14 and 60, between 16 and 50, between 17 and 40, more preferably between 18 and 30 nucleotides and most preferably between 18 and 26 nucleotides.

Suitable siRNA sequences can be obtained by routine tests, e.g. by experiments along the lines as carried out in the examples of the present application using pLenti6-vectors encoding for the respective siRNAs. For KMT9alpha, exemplary sequences are the sequences with the SEQ ID Nos. 1 and 2 (DNA sequences comprised in pLenti6-vectors) and SEQ ID No. 4, 5 and 6 (siRNA). For KMT9beta, exemplary sequences are the sequences with the SEQ ID No. 7 and 8 (siRNA). For METTL21A, an exemplary sequence is the sequence with the SEQ ID No. 9 (siRNA), whereas exemplary sequences for METTL21B are the sequences with the SEQ ID No. 10 and 11 (siRNA).

The term "gRNA" as used herein refers to a (so-called "guide") RNA molecule suitable for reducing or inhibiting the expression of the target, or for reducing or inhibiting the histone methyltransferase enzymatic activity of the target, in the present invention either KMT9alpha and/or KMT9beta, METTL21A or METTL21B, which may be a single stranded RNA molecule that is capable of hybridizing to either KMT9alpha and/or KMT9beta as the target sequence (indicated herein as "gRNA directed to the KMT9alpha KMT9beta gene") or METTL21A as the target sequence (indicated herein as "gRNA directed to the METTL21A gene") or METTL21B as the target sequence (indicated herein as "gRNA directed to the METTL21B gene"), thereby directing sequence-specific binding of a CRISPR complex (including Cas9) to the target sequence. The review by Waddington S, et al. A broad overview and review of CRISPR-Cas technology and stem cells. *Curr Stem Cell Rep*, 2, 9-20 (2016), doi: 10.1007/s40778-016-0037-5, gives an overview over the CRIPR-Cas technology (before the background of stem cells), of therapeutic applications of this technology and an outlook of these applications in the future.

The gRNA may be of any sequence that allows the gRNA molecule to direct sequence-specific binding of a CRISPR complex (comprising in particular Cas9) to the target sequence resulting in reduction or inhibition of the expression of the target, or in reducing or inhibiting the histone methyltransferase enzymatic activity of the target, in the present invention either KMT9alpha and/or KMT9beta, METTL21A or METTL21B. Preferably, the hybridizing sequence in the gRNA molecule has a length of between 5 and 100, between 5 and 80, between 7 and 60, between 8 and 50, between 9 and 40, more preferably between 10 and 35 nucleotides and most preferably between 10 and 30 nucleotides.

The term "Cas9" as used herein relates to a DNA endonuclease associated with the CRISPR system that is guided by the gRNA or a functional fragment or mutant thereof. Cas9 from any source, i.e. with a natural sequence or an engineered sequence, or derived from any species (such as e.g. from *Streptococcus pyrogenes, Streptococcus aureus* or *Streptococcus* thermophiles) may be used as long as the endonuclease is capable in combination with the gRNA to selectively carry out the desired DNA modification.

As used herein the term "hybridize" or "hybridizes" refers to the hybridization of a first to a second polynucleotide. To determine if two polynucleotides hybridize to each other, the skilled person will preferably conduct hybridization experiments in vitro under moderate or stringent hybridization conditions. Hybridization assays and conditions are known to those skilled in the art and can be found, for example, in Current Protocols in Molecular Biology, John Wiley & Sons, N. Y., 6.3.1-6.3.6, 1991. Stringent conditions may e.g. be conditions in which hybridization takes place in 6× sodium chloride/sodium citrate (SSC) at 45° C., followed by a wash in 0.2×SSC, 0.1% SDS at 65° C.

A "polynucleotide" according to the present invention is a double stranded DNA molecule. The polynucleotide may be inserted into an expression vector. The expression vector may e.g. be a prokaryotic or eukaryotic expression vector such as e.g. a plasmid, a minichromosome, a cosmid, a bacterial phage, a retroviral vector or any other vector known to the skilled person. The expression vector will be capable of providing an expression of the encoded protein or of the encoded RNA, respectively. An expression vector may comprise several polynucleotides encoding a protein and/or an RNA, such as e.g. an expression vector comprising a polynucleotide encoding a gRNA as defined above and a polynucleotide encoding Cas9 as defined above.

2. PHARMACEUTICAL COMPOSITION OF THE COMPOUND OF THE PRESENT INVENTION

The term "for use in treating cancer" is used herein in the meaning of a second medical indication. The inhibitor used for the treatment is the "pharmaceutically active agent" and may be present in a pharmaceutical composition when used to treat cancer.

"Pharmaceutically active agent" as used herein means that a compound is potent of modulating a response in a human or animal being in vivo. The term "pharmaceutically acceptable excipient" as used herein refers to excipients commonly comprised in pharmaceutical compositions, which are known to the skilled person. Such excipients are exemplary listed below. In view of the definition "pharmaceutically active agent" as given above, a pharmaceutically acceptable excipient can be defined as being pharmaceutically inactive.

A pharmaceutical composition according to the present invention may be formulated for oral, buccal, nasal, rectal, topical, transdermal or parenteral application. Oral application can be preferred. Parenteral application can also be preferred and includes intravenous, intramuscular or subcutaneous administration. A pharmaceutical composition of the present invention may also be designated as formulation or dosage form.

In general, a pharmaceutical composition according to the present invention can comprise various pharmaceutically acceptable excipients which will be selected depending on which functionality is to be achieved for the composition. A "pharmaceutically acceptable excipient" in the meaning of the present invention can be any substance used for the preparation of pharmaceutical dosage forms, including coating materials, film-forming materials, fillers, disintegrating agents, release-modifying materials, carrier materials, diluents, binding agents and other adjuvants. Typical pharmaceutically acceptable excipients include substances like sucrose, mannitol, sorbitol, starch and starch derivatives, lactose, and lubricating agents such as magnesium stearate, disintegrants and buffering agents.

The term "carrier" denotes pharmaceutically acceptable organic or inorganic carrier substances with which the active ingredient is combined to facilitate the application. Suitable pharmaceutically acceptable carriers include, for instance, water, salt solutions, alcohols, oils, preferably vegetable oils, polyethylene glycols, gelatin, lactose, amylose, magnesium stearate, surfactants, perfume oil, fatty acid monoglycerides and diglycerides, petroethral fatty acid esters, hydroxymethyl-cellulose, polyvinylpyrrolidone and the like. The pharmaceutical compositions can be sterilized and if desired, mixed with auxiliary agents, like lubricants, preservatives, stabilizers, wetting agents, emulsifiers, salts for influencing osmotic pressure, buffers, colorings, flavoring and/or aromatic substances and the like which do not deleteriously react with the active compound.

When it comes to RNA or a polynucleotide encoding said RNA used as inhibitor (such as e.g. a siRNA or gRNA or polynucleotides encoding the same), said RNA or polynucleotide encoding the same may be present with a pharmaceutically acceptable excipient selected from the group consisting of a solvent, aqueous solvent, non-aqueous solvent, dispersion media, diluent, dispersion, suspension aid, surface active agent, isotonic agent, thickening or emulsifying agent, preservative, lipid (such as e.g. DLin-DMA, DLin-K-DMA, DLin-KC2-DMA, 98N12-5, C12-200, DLin-MC3-DMA, reLNP, PLGA, PEG, PEG-DMA and PEGylated lipids and mixtures thereof), lipidoids liposome, lipid nanoparticle, core-shell nanoparticles, polymer, lipoplex, peptide, protein, cell and hyaluronidase. An injection route may be preferred for administration, such as e.g. intravenous, intraarterial, intraperitoneal, intradermal, subcutaneous and intramuscular injection.

If liquid dosage forms are considered for the present invention, these can include pharmaceutically acceptable emulsions, solutions, suspensions and syrups containing inert diluents commonly used in the art such as water. These dosage forms may contain e.g. microcrystalline cellulose for imparting bulk, alginic acid or sodium alginate as a suspending agent, methylcellulose as a viscosity enhancer and sweeteners/flavouring agents.

For parenteral application, particularly suitable vehicles consist of solutions, preferably oily or aqueous solutions, as well as suspensions, emulsions, or implants. Pharmaceutical formulations for parenteral administration are particularly preferred and include aqueous solutions in water-soluble form. Additionally, suspensions may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran.

Particularly preferred dosage forms are injectable preparations of a pharmaceutical composition of the present invention. Thus, sterile injectable aqueous or oleaginous suspensions can for example be formulated according to the known art using suitable dispersing agents, wetting agents and/or suspending agents. A sterile injectable preparation can also be a sterile injectable solution or suspension in a non-toxic parenterally acceptable diluent or solvent. Among the acceptable vehicles and solvents that can be used are water and isotonic sodium chloride solution. Sterile oils are also conventionally used as solvent or suspending medium.

Suppositories for rectal administration of a pharmaceutical composition of the present invention can be prepared by e.g. mixing the compound with a suitable non-irritating excipient such as cocoa butter, synthetic triglycerides and polyethylene glycols which are solid at room temperature but liquid at rectal temperature such that they will melt in the rectum and release the active agent from said suppositories.

For administration by inhalation, the pharmaceutical composition comprising a compound according to the present invention may be conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Oral dosage forms may be liquid or solid and include e.g. tablets, troches, pills, capsules, powders, effervescent formulations, dragees and granules. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. The oral dosage forms may be formulated to ensure an immediate release of the active agent or a sustained release of the active agent.

As regards human patients, a small molecule or a small chemical fragment selective for the respective HMT may be administered to a patient in an amount of about 0.001 mg to about 1000 mg per day, preferably of about 0.01 mg to about 10 mg per day, more preferably of about 0.1 mg to about 5 mg per day.

A pharmaceutical composition of the present invention may comprise the inhibitor of the present invention as the only pharmaceutically active agent. Alternatively, said pharmaceutical composition may comprise at least one further independent pharmaceutically active agent in addition to said inhibitor. As outlined above, the pharmaceutical composition according to the present invention are used in the treatment of cancer and more preferably in the specific cancer types as outlined above, such that at least one further independent pharmaceutically active agent directed to the treatment of cancer and such cancer types (such as e.g. a chemotherapeutic agent) may be additionally present.

3. PREFERRED EMBODIMENTS

In the following, further preferred embodiments of the present invention are listed.

A1. An inhibitor selected from the group consisting of a KMT9-inhibitor, a METTL21A-inhibitor and a METTL21B-inhibitor, for use in the treatment of cancer, wherein said inhibitor is not a non-selective protein methyltransferase inhibitor or wherein said inhibitor is a selective inhibitor selected from the group consisting of a selective KMT9-inhibitor, a selective METTL21A-inhibitor and a selective METTL21B-inhibitor.

A2. An inhibitor for use according to A1, wherein said cancer is selected from the group consisting of prostate cancer, breast cancer, ovarian cancer, colon cancer, colorectal cancer, glioblastoma, lung cancer, neuroblastoma, osteosarcoma, liposarcoma and leukemia.

A3. An inhibitor for use according to A2, wherein said prostate cancer is hormone-dependent prostate cancer or castration-resistant prostate cancer.

A4. An inhibitor for use according to A3, wherein said castration-resistant prostate cancer is resistant to enzalutamide.

A5. An inhibitor for use according to A2, wherein said lung cancer is non-small cell lung cancer or small cell lung cancer.

A6. An inhibitor for use according to any one of A1 to A5, wherein said inhibitor is a KMT9-inhibitor, preferably selected from the group consisting of a small molecule selective for KMT9-inhibition, a small chemical fragment selective for KMT9-inhibition, an antibody directed to KMT9alpha and/or KMT9beta or an antigen-binding fragment thereof, a siRNA directed to the KMT9alpha mRNA and/or the KMT9beta mRNA or a polynucleotide encoding said siRNA, and a gRNA directed to the KMT9alpha gene and/or KMT9beta gene or a polynucleotide encoding said gRNA.

A7. An inhibitor for use according to any one of A1 to A6, wherein said KMT9-inhibitor is a small molecule selective for KMT9-inhibition.

A8. An inhibitor for use according to any one of A1 to A6, wherein said KMT9-inhibitor is a small chemical fragment selective for KMT9-inhibition.

A9. An inhibitor for use according to any one of A1 to A6, wherein said KMT9-inhibitor is an antibody directed to KMT9alpha and/or KMT9beta or an antigen-binding fragment thereof, preferably an antibody directed to KMT9alpha or an antigen-binding fragment thereof.

A10. An inhibitor for use according to any one of A1 to A6, wherein said KMT9-inhibitor is a siRNA directed to the KMT9alpha mRNA and/or the KMT9beta mRNA or a polynucleotide encoding said siRNA, preferably a siRNA directed to the KMT9alpha mRNA or a polynucleotide encoding said siRNA.

A11. An inhibitor for use according to any one of A1 to A6, wherein said KMT9-inhibitor is a gRNA directed to the KMT9alpha gene and/or KMT9beta gene or a polynucleotide encoding said gRNA, preferably a gRNA directed to the KMT9alpha gene or a polynucleotide encoding said gRNA.

A12. An inhibitor for use according to A11, wherein said gRNA or polynucleotide encoding said gRNA is used in combination with Cas9 or a polynucleotide encoding Cas9.

A13. An inhibitor for use according to any one of A1 to A5, wherein said inhibitor is a METTL21A-inhibitor, preferably selected from the group consisting of a small molecule selective for METTL21A-inhibition, a small chemical fragment selective for METTL21A-inhibition, an antibody directed to METTL21A or an antigen-binding fragment thereof, a siRNA directed to the METTL21A mRNA or a polynucleotide encoding said siRNA, and a gRNA directed to the METTL21A gene or a polynucleotide encoding said gRNA.

A14. An inhibitor for use according to any one of A1 to A5 and A13, wherein said METTL21A-inhibitor is a small molecule selective for METTL21A-inhibition.

A15. An inhibitor for use according to any one of A1 to A5 and A13, wherein said METTL21A-inhibitor is a small chemical fragment selective for METTL21A-inhibition.

A16. An inhibitor for use according to any one of A1 to A5 and A13, wherein said METTL21A-inhibitor is an antibody directed to METTL21A or an antigen-binding fragment thereof.

A17. An inhibitor for use according to any one of A1 to A5 and A13, wherein said METTL21A-inhibitor is a siRNA directed to the METTL21A mRNA or a polynucleotide encoding said siRNA.

A18. An inhibitor for use according to any one of A1 to A5 and A13, wherein said METTL21A-inhibitor is a gRNA directed to the METTL21A gene or a polynucleotide encoding said gRNA.

A19. An inhibitor for use according to A18, wherein said gRNA or polynucleotide encoding said gRNA is used in combination with Cas9 or a polynucleotide encoding Cas9.

A20. An inhibitor for use according to any one of A1 to A5, wherein said inhibitor is a METTL21B-inhibitor, preferably selected from the group consisting of a small molecule selective for METTL21B-inhibition, a small chemical fragment selective for METTL21B-inhibition, an antibody directed to METTL21B or an antigen-binding fragment thereof, a siRNA directed to the METTL21B mRNA or a polynucleotide encoding said siRNA, and a gRNA directed to the METTL21B gene or a polynucleotide encoding said gRNA.

A21. An inhibitor for use according to any one of A1 to A5 and A20, wherein said METTL21B-inhibitor is a small molecule selective for METTL21B-inhibition.

A22. An inhibitor for use according to any one of A1 to A5 and A20, wherein said METTL21B-inhibitor is a small chemical fragment selective for METTL21B-inhibition.

A23. An inhibitor for use according to any one of A1 to A5 and A20, wherein said METTL21B-inhibitor is an antibody directed to METTL21B or an antigen-binding fragment thereof.

A24. An inhibitor for use according to any one of A1 to A5 and A20, wherein said METTL21B-inhibitor is a siRNA directed to the METTL21B mRNA or a polynucleotide encoding said siRNA.

A25. An inhibitor for use according to any one of A1 to A5 and A20, wherein said METTL21B-inhibitor is a gRNA directed to the METTL21B gene or a polynucleotide encoding said gRNA.

A26. An inhibitor for use according to A25, wherein said gRNA or polynucleotide encoding said gRNA is used in combination with Cas9 or a polynucleotide encoding Cas9.

B1. A KMT9-inhibitor for use in the treatment of cancer, wherein said KMT9-inhibitor is not a non-selective protein methyltransferase inhibitor or wherein said inhibitor is a selective KMT9-inhibitor.

B2. An inhibitor for use according to B1, wherein said cancer is selected from the group consisting of prostate cancer, breast cancer, ovarian cancer, colon cancer, colorectal cancer, glioblastoma, lung cancer, neuroblastoma and leukemia.

B3. An inhibitor for use according to B2, wherein said prostate cancer is hormone-dependent prostate cancer or castration-resistant prostate cancer.

B4. An inhibitor for use according to B3, wherein said castration-resistant prostate cancer is resistant to enzalutamide.

B5. An inhibitor for use according to B2, wherein said lung cancer is non-small cell lung cancer.

B6. An inhibitor for use according to any one of B1 to B5, wherein said inhibitor is selected from the group consisting of a small molecule selective for KMT9-inhibition, a small chemical fragment selective for KMT9-inhibition, an antibody directed to KMT9alpha and/or KMT9beta or an antigen-binding fragment thereof, a siRNA directed to the KMT9alpha mRNA and/or the KMT9beta mRNA or a polynucleotide encoding said siRNA, and a gRNA directed to the KMT9alpha gene and/or KMT9beta gene or a polynucleotide encoding said gRNA.

B7. An inhibitor for use according to any one of B1 to B6, wherein said KMT9-inhibitor is a small molecule selective for KMT9-inhibition.

B8. An inhibitor for use according to any one of B1 to B6, wherein said KMT9-inhibitor is a small chemical fragment selective for KMT9-inhibition.

B9. An inhibitor for use according to any one of B1 to B6, wherein said KMT9-inhibitor is an antibody directed to KMT9alpha and/or KMT9beta or an antigen-binding fragment thereof.

B10. An inhibitor for use according to any one of B1 to B6, wherein said KMT9-inhibitor is a siRNA directed to the KMT9alpha mRNA and/or the KMT9beta mRNA or a polynucleotide encoding said siRNA.

B11. An inhibitor for use according to any one of B1 to B6, wherein said KMT9-inhibitor is a gRNA directed to the KMT9alpha gene and/or KMT9beta gene or a polynucleotide encoding said gRNA.

B12. An inhibitor for use according to B11, wherein said gRNA or polynucleotide encoding said gRNA is used in combination with Cas9 or a polynucleotide encoding Cas9.

C1. A METTL21A-inhibitor for use in the treatment of cancer, wherein said METTL21A-inhibitor is not a non-selective protein methyltransferase inhibitor or wherein said inhibitor is a selective METTL21A-inhibitor.

C2. An inhibitor for use according to C1, wherein said cancer is selected from the group consisting of prostate cancer, breast cancer, glioblastoma, lung cancer, neuroblastoma and leukemia.

C3. An inhibitor for use according to C2, wherein said prostate cancer is hormone-dependent prostate cancer or castration-resistant prostate cancer.

C4. An inhibitor for use according to C3, wherein said castration-resistant prostate cancer is resistant to enzalutamide.

C5. An inhibitor for use according to C2, wherein said lung cancer is small cell lung cancer.

C6. An inhibitor for use according to any one of C1 to C5, wherein said inhibitor is selected from the group consisting of a small molecule selective for METTL21A-inhibition, a small chemical fragment selective for METTL21A-inhibition, an antibody directed to METTL21A or an antigen-binding fragment thereof, a siRNA directed to the METTL21A mRNA or a polynucleotide encoding said siRNA, and a gRNA directed to the METTL21A gene or a polynucleotide encoding said gRNA.

C7. An inhibitor for use according to any one of C1 to C6, wherein said METTL21A-inhibitor is a small molecule selective for METTL21A-inhibition.

C8. An inhibitor for use according to any one of C1 to C6, wherein said METTL21A-inhibitor is a small chemical fragment selective for METTL21A-inhibition.

C9. An inhibitor for use according to any one of C1 to C6, wherein said METTL21A-inhibitor is an antibody directed to METTL21A or an antigen-binding fragment thereof.

C10. An inhibitor for use according to any one of C1 to C6, wherein said METTL21A-inhibitor is a siRNA directed to the METTL21A mRNA or a polynucleotide encoding said siRNA.

C11. An inhibitor for use according to any one of C1 to C6, wherein said METTL21A-inhibitor is a gRNA directed to the METTL21A gene or a polynucleotide encoding said gRNA.

C12. An inhibitor for use according to C11, wherein said gRNA or polynucleotide encoding said gRNA is used in combination with Cas9 or a polynucleotide encoding Cas9.

D1. A METTL21B-inhibitor for use in the treatment of cancer, wherein said METTL21B-inhibitor is not a non-selective protein methyltransferase inhibitor or wherein said inhibitor is a selective METTL21B-inhibitor.

D2. An inhibitor for use according to D1, wherein said cancer is selected from the group consisting of prostate cancer, breast cancer, lung cancer, osteosarcoma, liposarcoma and leukemia.

D3. An inhibitor for use according to D2, wherein said lung cancer is non-small cell lung cancer.

D4. An inhibitor for use according to any one of D1 to D3, wherein said inhibitor is selected from the group consisting of a small molecule selective for METTL21B-inhibition, a small chemical fragment selective for METTL21B-inhibition, an antibody directed to METTL21B or an antigen-binding fragment thereof, a siRNA directed to the METTL21B mRNA or a polynucleotide encoding said siRNA, and a gRNA directed to the METTL21B gene or a polynucleotide encoding said gRNA.

D5. An inhibitor for use according to any one of D1 to D4, wherein said METTL21B-inhibitor is a small molecule selective for METTL21B-inhibition.

D6. An inhibitor for use according to any one of D1 to D4, wherein said METTL21B-inhibitor is a small chemical fragment selective for METTL21B-inhibition.

D7. An inhibitor for use according to any one of D1 to D4, wherein said METTL21B-inhibitor is an antibody directed to METTL21B or an antigen-binding fragment thereof.

D8. An inhibitor for use according to any one of D1 to D4, wherein said METTL21B-inhibitor is a siRNA directed to the METTL21B mRNA or a polynucleotide encoding said siRNA.

D9. An inhibitor for use according to any one of D1 to D4, wherein said METTL21B-inhibitor is a gRNA directed to the METTL21B gene or a polynucleotide encoding said gRNA.

D10. An inhibitor for use according to D9, wherein said gRNA or polynucleotide encoding said gRNA is used in combination with Cas9 or a polynucleotide encoding Cas9.

4. EXAMPLES

4.1. Example 1

When starting from the known histone methyltransferase (HMT) DOT1L[2,4], the only identified HMT of the seven-β-strand family, a cluster analysis from multiple amino acid sequence alignments of putative methyltransferase domains indicated that C21orf127[6-11] (also named Hemk2, Mtq2, N6amt1, N6AMT1, PrmC or PRED28) might also be a HMT, since it shares a similarity with DOT1L.

To elucidate whether C21orf127 is indeed a histone methyltransferase, core histones were incubated with recombinant purified C21orf127 in the presence of the methyl donor S-adenosyl-methionine (SAM) [$^3$H]. This methyltransferase assay was performed with TRMT112, given that C21orf127 has been shown to associate with TRMT112[14,15]. The C21orf127/TRM112 heterodimer strongly methylated histone H4 (H4) of core histones (data not shown).

To confirm methylation of H4, recombinantly expressed purified histone H4, H3, H2A, H2B, and H1 were incubated with C21orf127/TRMT112 in the presence of SAM [$^3$H]. Solely H4 was methylated by C21orf127/TRMT112 (FIG. 1A). To map the residue targeted by C21orf127/TRMT112, H4 was methylated in vitro. Methylated H4 peptide was then proteolytically cleaved by Arg-C, and the resulting H4 peptides were analysed by liquid chromatography-tandem mass spectrometry (LC-MS/MS). To distinguish enzymatic from non-enzymatic methylation, translational errors, and spurious methylation of recombinant H4 in the bacterial expression host, in vitro methylation reactions were performed using either [$^{12}CH_3$]-SAM (SAM) or [$^{13}CD_3$]-SAM (hSAM). The MS analysis pinned down the substrate to lysine (K) 12 of H4, which was exclusively monomethylated (data not shown). Consistent with the MS analysis, wild-type H4 protein, but not mutant H4 where K12 was changed to an alanine (A) residue (H4K12A), was methylated demonstrating that C21orf127/TRMT112 exclusively targets H4 at K12 (FIG. 1B). To further corroborate these findings, H4 or core histones were incubated with C21orf127/TRMT112 in the presence of SAM. Western blot analyses performed with an anti-H4K12me1-specific antibody (i.e. specific for the monomethylation) confirmed monomethylation of H4K12 (data not shown).

The methyltransferase activity of C21orf127/TRMT112 could be blocked by the presence of sinefungin. The latter is a potent general antagonist of methyltransferases by competing with SAM (sinefungin may be referred to as general competitive inhibitor of SAM-dependent methyltransferases, see also[16]; FIG. 1C).

To investigate the molecular basis for H4K12 recognition, the crystal structure of C21orf127/TRMT112 in complex with S-adenosyl-homocysteine (SAH) and H4K12me1 peptide at a resolution of 1.9 Å was solved (data not shown). The catalytic domain of C21orf127 adopts the canonical class I fold of SAM-dependent methyltransferases consisting of a seven-membered β-sheet and five α-helices (data not shown). The TRMT112 fold comprises three α-helices and three antiparallel β-strands (see FIG. 1D). As observed for the *E. cuniculi* parasite homologs Mtq2/Trmt11218[18], C21orf127 binds TRMT112 mainly through conserved hydrophobic-hydrophobic interactions. In both complexes a conserved loop at the heterodimer interface is involved in the formation of the SAM-binding pocket. In C21orf127, the side chain of aspartate (D)103 forms hydrogen bonds with the adenine moiety of SAH (data not shown). These findings suggest that interaction with D103 and C21orf127/TRMT112 heterodimerisation is obligatory for SAM binding. To corroborate this idea, SAM binding was assayed either to monomeric C21orf127 or TRMT112, or to C21orf127/TRMT112 or the mutant C21orf127(D103)/TRMT112 heterodimers by isothermal titration calorimetry (ITC). While high affinity binding of SAM to C21orf127/TRMT112 (Kd=2.5 μM) was observed, no SAM binding was observed to C21orf127 or TRMT112 alone or C21orf127(D103)/TRMT112 (data not shown). Accordingly, only the C21orf127/TRMT112 heterodimer displayed HMT activity (data not shown).

It was found that the histone H4 substrate located at an acidic patch on the surface of C21orf127 with well-defined electron density for amino acid residues 11 to 15 of the H4 peptide (data not shown). In the crystal, K12me1 of the H4 peptide is positioned in the lysine channel close to the SAM binding pocket (data not shown). The substrate binding pocket is formed by amino acid residues tyrosine (Y)23, glutamic acid (E)24, aspartic acid (D)28, asparagine (N)122, proline (P)123, Y125, tryptophan (W)144, and E204 of C21orf127 (data not shown). The methylated ε-ammonium group of H4K12 forms hydrogen bonds with the backbone carbonyl of P123 and the side chains of D28 and N122 in the NPPY motif, which has been proposed to mediate the methyl transfer in members of seven-β-strand family. In addition, the δ2-amino group of N122 forms a hydrogen bond with the α-carbonyl group of SAH (data not shown). Accordingly, mutation of N122 to alanine (N122A) abrogated SAM binding and HMT activity (data not shown). The N122A mutation did not alter heterodimer formation since C21orf127/TRMT112 and C21orf127(N122A)/TRMT112 heterodimers showed comparable elution profiles in gel filtration chromatography (data not shown).

Next, it was determined how C21orf127/TRMT112 can act on substrates as diverse as H4K12 (lysine methylation) and ETF1 (glutamine methylation[20]). It was hypothesized that distinct substrate binding modes exist suggesting that C21orf127 point mutants can be identified that discriminate between histone H4 and ETF1 methylation. Indeed, mutation of tyrosine 125 to alanine (Y125A) in the consensus motif NPPY of C21orf127 resulted in methylation of H4K12, but not ETF1 by the mutant C21orf127(Y125A)/TRMT112 complex (data not shown). Of note, the side chain of Y125 does not contact the H4K12 substrate peptide and the Y125A mutation did not affect SAM binding (data not shown). Whereas the mutant C21orf127(Y125A)/TRMT112 complex discriminated between H4K12 and ETF1, the SAM binding-defective C21orf127(N122A)/TRMT112 complex neither methylated histone H4 nor ETF1 (data not shown).

The example shows that the C21orf127/TRMT112 complex is a novel HMT that monomethylates histone H4 on Lysine 12 (K12). The enzymatic activity of C21orf127/TRMT112 can be inhibited by compounds, such as e.g. a general SAM-competitive inhibitor. On the basis of the above results, reference to heterodimeric C21orf127/TRMT112 is made herein alternatively as lysine methyltransferase 9 (KMT9) assembled by KMT9α (C21orf127 or N6AMT1) and KMT9β (TRMT112).

4.2. Example 2

The expression of KMT9 in human normal and tumour prostate cells was profiled. Database analyses indicated that RNA levels of KMT9α, and KMT9B are increased in prostate tumour compared to normal prostate cells (data not shown). Accordingly, Western blot analyses showed expression of KMT9α and KMT9β in human normal immortalized prostate epithelial cells such as RWPE1 and PNT2 and increased protein levels in prostate tumour cells such as androgen-dependent LNCaP or androgen-independent PC-3M, C4-2B, and DU145 (FIG. 2A). KMT9 expression was also detected in prostate tumour cells that are resistant to enzalutamide (EnzaR), a non-steroidal anti-androgen, which is used as standard treatment for metastatic, castration-resistant prostate cancer (FIG. 2A and [21]). In accordance with Western blot data, increased KMT9α and KMT9β mRNA levels in human prostate tumour compared to adjacent normal prostate tissue was revealed by protein database analyses (data not shown). Furthermore, immunohistochemical analyses showed that KMT9α and the histone mark H4K12me1 are present in patient-derived human normal prostate as well as in prostate tumour tissue including primary and locally advanced/recurrent tumours, lymph node metastases, and distant bone or lung metastases (FIG. 2B). Analysis of the immunohistochemical stainings demonstrated that the percentage of tumours expressing high levels of KMT9α (FIG. 2C) and displaying nuclear presence (FIG. 2D) increased with disease progression.

To correlate KMT9 protein levels with the presence of H4K12me1, PC-3M cells were treated with control siRNA (siCtrl) or siRNA directed against KMT9α (siKMT9α) and analysed H4K12me1 levels by Western blotting (FIG. 2E). The data showed that H4K12me1 levels decreased upon KMT9α knockdown. To further corroborate writing of the H4K12me1 mark by KMT9 in vivo, histone H4 from PC-3M cells treated with siCtrl or siKMT9α was isolated. Following H4 extraction and tryptic digestion, H4 aa4-17 peptides were analysed by LC-MS/MS (FIG. 2E). The data confirmed the occurrence of H4K12me1 in vivo and reduction of this chromatin mark upon depletion of KMT9α (FIG. 2E). Of note, MS analyses showed that in PC-3M cells the level of H4K12me1 represent 0.04% of total histone H4 (FIG. 2E). Depending on the cell line, the percentage of H4K12me1 varied from 0.04% to 0.12% of total histone H4 (data not shown). These values are comparable to the abundance of other modifications such as H3K4me1 or H3K27ac ranging from 0.04% to 0.1% and 0.05% to 0.1% of total histone H3, respectively (see [22 and 23]) Finally, using gene editing, human embryonic kidney (HEK) 293 cells with genetic loss of KMT9α (HEK 293 KMT9α−/−) were generated. Proficient control and KMT9α-deficient HEK 293 cells were isotopically labelled using light ($[^{12}CH_3]$-methionine) and heavy methionine ($[^{13}CD_3]$-methionine)[24]. Subsequently, H4 was isolated from these cells and trypsin-digested. The targeted analysis of the resulting H4 aa4-17 peptides by MS/MS showed presence of H4K12me1 in proficient control and complete loss of the chromatin mark in the KMT9α-deficient HEK 293 cells (data not shown). In summary, the above data demonstrate occurrence of the H4K12me1 chromatin mark in vivo and regulation of H4K12me1 levels by KMT9.

To unravel the KMT9 cistrome, the genomic localisation of KMT9 (composed of KMT9α and KMT9β) in PC-3M cells was analysed by ChIP-seq using antibodies directed against KMT9α and KMT9β (data not shown). Analysis of the ChIP-seq data revealed 8,060 locations occupied by both, KMT9α and KMT9β, and a strong enrichment of KMT9α/β co-locations at gene promoters (4,729 genes) (data not shown). Furthermore, a global decrease in KMT9α and KMT9β reads in cells treated with siRNA against KMT9α and KMT9β compared to siCtrl-treated cells was observed, which demonstrated specificity of the KMT9α and KMT9β antibodies (data not shown). The enrichment of KMT9α/β co-locations at gene promoters suggested an involvement of KMT9 in transcriptional regulation. Consequently, global transcriptome analyses (RNA-seq) were performed in PC-3M cells treated with siCtrl or siKMT9α and 6,326 differentially expressed genes upon KMT9α knockdown were identified (data not shown). To exclude potential siKMT9α off-target effects, MCF10A human breast epithelial cells that do not express KMT9α were treated with siKMT9α and RNA-seq was performed. This analysis uncovered only 73 differentially expressed genes demonstrating that siKMT9α displays only very little off-target effects (data not shown). Intersection of the 6,326 differentially expressed and the 4,729 genes with KMT9 promoter occupancy unravelled 1,455 differentially expressed, direct KMT9 target genes (data not shown). To decipher biological functions of these 1,455 target genes, gene enrichment analyses were performed. The enrichment analysis for biological processes uncovered genes involved in cell cycle regulation among the top-ranking categories (data not shown). Accordingly, KMT9α depletion in PC-3M cells significantly reduced expression of genes involved in cell cycle regulation (data not shown). Reduced expression levels of genes including baculoviral IAP repeat containing 5 (BIRC5), cyclin dependent kinase 1 (CDK1), outer dense fiber of sperm tails 2 (ODF2), oxidative stress induced growth inhibitor family member 2 (OSGIN2), phosphoglycerate dehydrogenase (PHGDH), rhotekin 2 (RTKN2), centriolar assembly protein (STIL), and vaccinia related kinase 1 (VRK1) were verified by qRT-PCR analysis upon treatment of cells with siKMT9α (data not shown). Taken together, the data uncovered that cell cycle genes are direct KMT9-regulated target genes.

To investigate whether altered expression of direct KMT9 target genes correlated with H4K12me1 levels at gene promoters ChIP-seq for this chromatin mark were performed (data not shown). In total, 2,120 KMT9α/KMT9β/H4K12me1 co-locations were observed that are enriched at gene promoters (data not shown). Importantly, a dramatic decrease in H4K12me1 reads was detected upon KMT9α depletion (data not shown). Furthermore, H4K12me1 peaks co-localized with KMT9α, and KMT9β peaks at the promoter region of differentially expressed direct KMT9 target genes (data not shown). Next, it was investigated whether a decrease in H4K12me1 levels, which correlates with reduced expression of KMT9 target genes, also involves changes in the levels of known repressive histones marks. In ChIP-seq analyses, increased levels of the repressive H4K20me3 mark at H4K12me1 peaks were detected upon KMT9α knockdown. (data not shown). Together, the data show co-localisation of KMT9α, KMT9β, and H4K12me1 at gene promoters and the control of H4K12me1 levels as well as transcriptional regulation by KMT9.

The example shows (i) that KMT9 is expressed in normal as well as prostate tumour cells (also derived from patients), (ii) that KMT9 is the enzyme responsible for the H4K12me1 modification in vivo, (iii) that KMT9 colocalises with H4K12me1 on the genome in vivo and (iv) that cell cycle genes are direct KMT9-regulated target genes.

4.3. Example 3

Since KMT9 regulates expression of cell cycle genes, it was analysed by flow cytometry whether RNAi-mediated knockdown of KMT9α in PC-3M cells resulted in changes of the cell cycle phase distribution. As shown in FIG. 3A, more cells were arrested in G0-G1 and less cells were present in S phase upon KMT9α depletion indicating decreased cell proliferation. In addition, an increase in apoptotic PC-3M cells upon siKMT9α treatment was observed (FIG. 3B). To corroborate these observations, siRNA-mediated knockdown of KMT9α in PC-3M cells was performed and proliferation was monitored in real-time (FIG. 3C). Knockdown efficiency of KMT9α was verified by Western blot analysis (FIG. 3C). In accordance with the flow cytometry observations, loss of KMT9α severely interfered with proliferation of PC-3M cells (FIG. 3C). Similarly, KMT9α depletion strongly reduced proliferation of androgen-dependent (LNCaP and LAPC4) and androgen-independent, castration-resistant (C4-2B, and LNCaP-abl) human prostate tumour cell lines (FIG. 3D, 3E, 3H, 3I). Furthermore, as shown in FIGS. 3F, 3J and 3K, proliferation of enzalutamide-resistant LAPC4 EnzaR, LNCaP-abl EnzaR, and DuCaP EnzaR cells was also severely impaired. Importantly, inhibition of proliferation upon siRNA-mediated knockdown of KMT9α was accompanied by a decrease in H4K12me1 levels (FIGS. 3C-3F and 3H to 3K). In contrast, proliferation of non-tumourigenic epithelial MCF10A cells that do not express KMT9α was not altered by treatment with siKMT9α suggesting that reduced proliferation of prostate tumour cells is not due to off-target effects of the siRNAs (FIG. 3L). Knockout or knockdown of KMT9α did not affect proliferation of non-cancer cell lines such as HEK 293 or C2C12 (data not shown).

Next, it was investigated whether impaired cell proliferation upon KMT9α depletion could be rescued by ectopic wild-type KMT9α. For this purpose, LNCaP cells were infected with lentivirus driving expression of either lacZ control (LacZ) or KMT9α (KMT9α) and these cells were treated with siCtrl or siRNA that targets the three-prime untranslated region of the endogenously transcribed KMT9α mRNA (siKMT9α-3'UTR). Proliferation of LNCaP-LacZ control cells was strongly impaired upon knockdown of endogenous KMT9α, whereas proliferation of LNCaP/siKMT9α-3'-UTR cells ectopically expressing KMT9α was not significantly affected (FIG. 3G). In contrast, the enzymatically inactive mutant KMT9α(N122A) failed to rescue the proliferation defect caused by siKMT9α-3'-UTR (FIG. 3G, right panel). These results demonstrate that the enzymatic activity of KMT9α is necessary and sufficient to maintain LNCaP cell proliferation. In addition to KMT9α(N122A), which neither methylates H4 nor ETF1, we tested the mutant KMT9α(Y125A), which methylates H4 but not ETF1. Similar to wild-type KMT9α, ectopic expression of the KMT9α(Y125A) mutant rescued the growth defect caused by depletion of endogenous KMT9α (FIG. 3G, right panel). These data demonstrate that the control of proliferation by KMT9α is dependent on its enzymatic activity.

Since KMT9 was reported to methylate ETF1, it was investigated whether ETF1 methylation plays a role in the regulation of PC-3M and LNCaP cell proliferation. Therefore, ETF1 was immunoprecipitated from lysates of PC-3M and LNCaP cells that were treated with siCtrl or siKMT9α and performed Western blot analyses using an antibody that specifically detects methylated ETF120. However, under the chosen experimental conditions, no significant ETF1 methylation by endogenous KMT9α/KMT9β and no changes of ETF1 levels nor of ETF1 methylation upon KMT9α knockdown were detected (data not shown). These observations suggest that reduced proliferation of PC-3M and LNCaP cells upon KMT9α knockdown does not involve ETF1 methylation. In addition it was investigated whether impaired cell proliferation upon KMT9α depletion could be rescued by ectopic expression of wild-type ETF1. For this purpose, LNCaP cells were infected with lentivirus driving expression of either LacZ (LNCaP-LacZ) or ETF1 (LNCaP-ETF1) and these cells were treated with siCtrl or siKMT9α. Similarly to LNCaP-LacZ, proliferation of LNCaP-ETF1 cells was strongly impaired upon knockdown of endogenous KMT9α showing that ETF1 failed to rescue the proliferation defect caused by siKMT9α (data not shown). These data demonstrate that the control of proliferation by KMT9α is dependent on its enzymatic activity but is independent of ETF1 methylation.

The example shows that KMT9 controls proliferation of prostate tumour cells.

4.4. Example 4

It was investigated whether KMT9α loss might affect tumour growth in mice. Therefore, PC-3M and LNCaP cells were infected with lentivirus driving expression of either miRNA control (miRNA Ctrl) or miRNA against KMT9α (miRNA KMT9α) and implanted subcutaneously in the flank of immunocompromised mice. Importantly, upon knockdown of KMT9α, growth and final weight of the prostate tumour cell-derived xenografts were strongly reduced compared to control (FIGS. 4A to 4D and 4E to 4H). To investigate whether knockdown of KMT9α also blocks growth of enzalutamide-resistant tumours, LAPC4 EnzaR miCtrl and miKMT9α cells were implanted subcutaneously in the flank of immunocompromised, castrated mice. As anticipated, it was also observed that growth and final weight of KMT9α-depleted LAPC4 EnzaR cell-derived xenografts were strongly reduced compared to control (FIG. 4I to 4L).

N6AMT1 knockdown was carried out in various cancer cells lines, namely cell lines of breast cancer, ovarian carcinoma, colon cancer, glioblastoma, lung cancer and neuroblastoma and it was observed for all tested cell lines that the knockdown of N6AMT1 results in a proliferation block of these cancer cells lines (see FIGS. 5 and 6, also for details of the tested cell lines). Since various cell lines of each of these different cancer types exist, several of such cell lines have in some instances been tested for a specific cancer type, as can be derived from FIGS. 5 and 6. It is generally noted that a negative result in a single cell line of a specific cancer type does not necessarily mean that the proliferation of this specific cancer type cannot be blocked by a knockdown of N6AMT1—such an effect might be very specific for this particular cell line.

The example shows that KMT9α (referred to as N6AMT1 in FIGS. 5 and 6) controls proliferation and xenograft tumour growth of prostate tumour cells as well proliferation of various other cancer cells.

4.5. Example 5

When starting from the known histone methyltransferase (HMT) DOT1L, a cluster analysis from multiple amino acid sequence alignments of the putative methyltransferase domain indicated that METTL21A might also be a HMT, since it shares similarity with DOT1L.

To elucidate whether METTL21A is indeed a histone methyltransferase, recombinantly expressed purified core histones, mono-nucleosomes, oligo-nucleosomes, histone H4, H3, H2A, H2B, and H1 were incubated with METTL21A in the presence of SAM [3H]. Core histones and histone H4 was methylated by METTL21A (FIG. 7a1). METTL21A mono-methylates H4K20 (FIG. 7a2). Wild-type H4 protein, but not mutant H4 where K20 was changed to an alanine (A) residue (H4K20A), was methylated by METTL21A (FIG. 7a2).

Based on the data gained for KMT9α (see Examples 1 to 4 above), it was postulated that inhibition of METTL21A might also have effects on tumour cell proliferation.

To verify this hypothesis, RNAi-mediated knockdown of METTL21A in the (i) lung tumor cell lines A549, NCIH-292 and GLC2 (SCLC); (ii) prostate tumour cell lines PC-3M and DU145; (iii) neuroblastoma cell lines SY5Y and SK-N-MC; (iv) glioblastoma cell lines LN229 and A172; and (v) breast tumor cell line MDA-MB-231 was performed, followed by proliferation assays. Knockdown of METTL21A severely interfered with proliferation of all tested tumour cells (FIG. 7b to f and FIG. 10). In agreement with the in vitro data, METTL21A depletion severely reduces H4K20me1 levels, which correlate with impaired cell proliferation as monitored by Western blotting and proliferation in real-time (FIG. 10). Of note, RNA or protein levels of KMT5A are not altered by METTL21A RNAi during cell cycle progression thus, excluding an involvement of this known H4K20me writer. In addition, the Western blot analyses uncovered, that METTL21A is localized both in the cytoplasm and the nucleus of human tumour cells (FIG. 10).

The example shows that METTL21A is a HMT and methylates histone H4 at K20. The example further shows that METTL21A controls proliferation of various cancer cells.

4.6. Example 6

When starting from the known histone methyltransferase (HMT) DOT1L, a cluster analysis from multiple amino acid sequence alignments of the putative methyltransferase domain indicated that METTL21B might also be a HMT, since it shares similarity with DOT1L.

To elucidate whether METTL21B is indeed a histone methyltransferase, recombinantly expressed purified oligo-nucleosomes, mono-nucleosomes, core histones, histone H4, H3, H2A, H2B, and H1 were incubated with METTL21B in the presence of SAM [3H]. All histones were methylated by METTL21B (FIG. 8a).

Based on the data gained for KMT9α (see Examples 1 to 4 above), it was postulated that inhibition of METTL21B might also have effects on tumour cells, in particular on proliferation and migration of tumor cells. To verify this hypothesis, RNAi-mediated knockdown of METTL21B in the (i) lung tumor cell line NCIH-H2087 (NSCLC); (ii) osteosarcoma tumour cell line SJSA-1; (iii) breast cancer cell lines Cal-120, Hs578T, JIMT-1; and (iv) liposarcoma cell line T778 was performed, followed by proliferation assays (FIG. 8b to g). In addition, migration assays were performed upon RNAi-mediated knockdown of METTL21B in the following cell lines: SJSA-1, JIMT-1 and Cal-120 (FIG. 8h to j). Knockdown of METTL21B severely interfered with proliferation and migration of all tested tumour cells.

The example shows that METTL21B is a HMT and methylates histones. The example further shows that METTL21B controls proliferation and migration of various cancer cells.

4.7. Example 7

It was tested in this example whether the known DOT1L-inhibitors EPZ5676, SGC0946 and EPZ004777 (which are commercially available) are capable of inhibiting KMT9. To this aim, histone H4 was incubated with SAM[3H] in the presence of recombinant KMT9 (provided in the form of the heterodimer of KMT9α and KMT9β) and the three aforementioned inhibitors. Sinefungin was used as positive control and histone H4 methylation was revealed by autoradiography.

As can be derived from FIG. 9, contrary to sinefungin, the three DOT1L-inhibitors do not block the HMT-activity of KMT9.

This example shows that the specificity of inhibitors against different histone methyl transferases, here DOT1L and KMT9, differs.

4.8. Example 8

To get further insight in the function of KMT9 in colorectal cancer (CRC), a bioinformatics approach to analyze transcriptome (RNA-seq) data from 327 CRC patients was used. The data uncovered that the expression levels of KMT9α (FIG. 11a) and its obligatory binding partner KMT9β (FIG. 11b) are significantly increased in CRC in comparison to healthy large intestine tissue independent of the tumor stage. Additionally, the protein levels of KMT9α and KMT9β in multiple CRC cell lines were analyzed. KMT9α and KMT9β display ubiquitous expression in the cell lines tested with the exception of KMT9β, which is not present in RKO cells.

Next, the subcellular localization of KMT9α in multiple CRC cell lines and in CRC patients was analyzed. The data uncover that KMT9α is localized both in the cytoplasm and the nucleus of human CRC cells (FIG. 11d) and in tissue samples of human CRC patients (FIG. 11e).

To verify the H4K12me writer function of KMT9 in CRC cells, KMT9α was depleted in human CRC cells such as SW480 and Caco-2 by RNAi. As shown in FIG. 12 a, KMT9α depletion reduced H4K12me levels in CRC cells. To address the question whether loss of KMT9 might correlate with impaired proliferation of CRC cells, siRNA-mediated knockdown of KMT9α was performed in multiple CRC cells and proliferation was monitored in real-time. Of note, depletion of KMT9α severely interferes with proliferation of multiple CRC cell lines as exemplarily displayed in (FIGS. 12b and c).

To investigate the role of KMT9 in the control of migration, migration assays in KMT9α-proficient and KMT9-depleted cells were performed in real-time. As demonstrated in FIG. 13a to c, siRNA-mediated depletion of KMT9α resulted in robustly reduced migration of CRC cells. Hand in hand with these data, KMT9α also impairs invasion of CRC cells (FIGS. 13d and e).

In order to understand the impact of KMT9 loss in CRC, mouse colorectal 3D tumor-organoids were established. To generate 3D tumor-organoids advantage was taken of the $Rosa26^{Cre/ERT2} \times KMT9\alpha^{fl/fl}$ mouse cohort and the two-step AOM/DSS tumor model was applied. AOM/DSS treatment is a powerful, widely-used and reproducible procedure to induce CRC in mice. The model utilizes chemical induction of DNA damage followed by repeated cycles of colitis. AOM (Methyl-methylimino-oxidoazanium) is a pro-carcinogen, which is metabolized by the cytochrome p450 system in the liver and excreted into the bile. Subsequent uptake by colonic epithelium induces mutagenesis in colonic epithelial cells. DSS is a heparin-like polysaccharide, which when dissolved in the drinking water inflicts additional colonic epithelial damage. Combining AOM and DSS provides a two-step tumor model of CRC. Colorectal cancer growth was manifested in $Rosa26^{Cre/ERT2} \times KMT9\alpha^{fl/fl}$ mice by AOM/DSS treatment and isolated cancer initiating/cancer stem cells (CSC) from the tumor tissue. To account for tumor heterogeneity, cancer initiating/cancer stem cells were isolated from five AOM/DSS treated $Rosa26^{Cre/ERT2} \times KMT9\alpha^{fl/fl}$ mice and five AOM/DSS treated $Rosa26^{Cre/ERT2} \times KMT9\alpha^{wt/wt}$ control mice. Accordingly, five different mouse-derived tumor organoid cultures were generated from each genotype. Next, growth upon tamoxifen-induced loss of KMT9α was analyzed in these tumor organoids. The data shown in FIG. 14a to d provide strong evidence that loss of KMT9α severely impairs growth of AOM/DSS colon tumor organoids.

Due to the profound intratumoral heterogeneity of solid CRCs, patient-derived organoids (PDOs) have recently emerged as robust preclinical models with a high degree of similarity to the original patient tumors (van de Wetering et al. (2015) Prospective derivation of a living organoid biobank of colorectal cancer patients. Cell 161, 933-945). Thus, to further validate the role of KMT9α in CRC patient-derived CRC organoids were established and expression of KMT9α was decreased by transduction of a lentivirus expressing KMT9α miRNA. In accordance with the results obtained in 2D cell culture (FIGS. 12b and c) and mouse tumor organoids (FIG. 14a to d) the data depicted in FIGS. 14e and f provide strong evidence that loss of KMT9α also impairs tumor growth in human CRC organoids.

In summary, this example shows that the writing of the chromatin mark H4K12me by KMT9 is linked with KMT9 dependent proliferation, migration and invasion of CRC.

4.9. Example 9: Synthesis of KMT9-Inhibiting Compounds 72b and 75b

Synthesis of Compound 72b (1R,2S,3R,5R)-3-(4-chloro-7H-pyrrolo[2,3-d]pyrimidin-7-yl)-5-(hydroxymethyl)cyclopentane-1,2-diol (64). To a solution of (1R,2S,3R,5R)-3-amino-5-(hydroxymethyl)cyclopentane-1,2-diol hydrochloride (5.0 g, 27 mmol, 1 eq.) in Abs. grade EtOH (234 mL) was added 4,6-dichloropyrimidin-5-acetaldehyde (5.15 g, 27 mmol, 1 eq.) and Et$_3$N (12.5 mL, 53.9 mmol, 2 eq.). The reaction mixture was refluxed (90° C.) for 16 h. Volatiles were then evaporated in vacuo and the corresponding residue was purified by silica gel flash column chromatography (CH$_2$Cl$_2$/MeOH 99:1-90:10) to afford compound 64 as a yellow solid (7.39 g, 26 mmol, 97%). C$_{12}$H$_{14}$N$_3$O$_3$Cl (283.71 g/mol). $^1$H-NMR (400 MHz; DMSO-d$_6$): δ 8.61 (s, 1H, H2), 7.91 (d, $^3$J=3.6 Hz, 1H, H8), 6.68 (d, $^3$J=3.6 Hz, 1H, H7), 5.04 (dt, $^3$J=10.2 Hz and $^3$J=8.9 Hz, 1H, H1'), 4.89-4.75 (m, 3H, 3×OH), 4.23 (dd, $^3$J=8.9 Hz and $^3$J=5.2 Hz, 1H, H2'), 3.83 (dd, $^3$J=5.2 Hz and $^3$J=2.8 Hz, 1H, H3'), 3.52-3.43 (m, 2H, H5'), 2.22 (dt, $^3$J=12.8 Hz $^3$J=8.9 Hz, 1H, H6'$_A$), 2.09-2.02 (m, 1H, H4'), 1.61 (ddd, $^3$J=12.8 Hz, $^3$J=10.2 Hz and $^3$J=7.6 Hz, 1H, H6'$_B$); APCI-MS(+): m/z 284.0 [M+H]$^+$.

((3aR,4R,6R,6aS)-6-(4-chloro-7H-pyrrolo[2,3-d]pyrimidin-7-yl)-2,2-dimethyltetrahydro-4H-cyclopenta[d][1,3]dioxol-4-yl)methanol (65). To a solution of 64 (7.39 g, 25.8 mmol, 1 eq.) in acetone (685 mL) was added CH(OEt)$_3$ (21.6 mL, 128.9 mmol, 5 eq.) followed by pTsOH (24.7 g, 128.9 mmol, 5 eq.) and the mixture was stirred at rt for 16. After quenching with 5% NaHCO$_3$, most of acetone was evaporated and the remaining aqueous solution was extracted 3 times with CH$_2$Cl$_2$. The combined organic layer were dried over Na$_2$SO$_4$, filtered and evaporated to afford the crude product subjected to flash column chromatography (CH$_2$Cl$_2$/MeOH 99.6:0.4-97.5:2.5). The pure compound 65 was obtained as a beige foam (4.81 g, 14.8 mmol, 58%). C$_{15}$H$_{18}$N$_3$O$_3$Cl (323.78 g/mol). $^1$H-NMR (400 MHz; DMSO-d$_6$): δ 8.65 (s, 1H, H2), 7.96 (d, $^3$J=3.8 Hz, 1H, H8), 6.72 (d, $^3$J=3.8 Hz, 1H, H7), 5.12-5.06 (m, 1H, H1'), 4.91 (t, $^3$J=7.0 Hz, 1H, H2'), 4.81 (t, $^3$J=5.4 Hz, 1H, OH-5'), 4.55 (dd, $^3$J=7.0 Hz and $^3$J=4.4 Hz, 1H, H3'), 3.52 (td, $^3$J=5.2 Hz and $^4$J=0.8 Hz, 2H, H5'), 2.28-2.21 (m, 2H, H4', H6'$_A$), 2.13-2.08 (m, 1H, H6'$_B$), 1.48 (s, 3H, CH$_3$), 1.22 (s, 3H, CH$_3$); APCI-MS(+): m/z 324.1 [M+H]$^+$.

((3aR,4R,6R,6aS)-2,2-dimethyl-6-(4-(methylamino)-7H-pyrrolo[2,3-d]pyrimidin-7-yl)tetrahydro-4H-cyclopenta[d][1,3]dioxol-4-yl)methanol (66). To a solution of 65 (4.81 g, 14.7 mmol) in n-BuOH (37 mL), in a α-waves reactor, was added 37 mL of a 33% CH$_3$NH$_2$ solution in EtOH. The reaction mixture was stirred under α-waves irradiation at 120° C. (100 W, 6-7 bar) for 15 min. After completion of the reaction, the volatiles were evacuated and the crude product was used without further purification (4.46 g, 14.0 mmol, 95%). C$_{16}$H$_{22}$N$_4$O$_3$ (318.38 g/mol). $^1$H-NMR (400 MHz; DMSO-d$_6$): δ 8.14 (s, 1H, H2), 7.66 (bs, 1H, NH), 7.32 (d, $^3$J=3.6 Hz, 1H, H8), 6.60 (d, $^3$J=3.6 Hz, 1H, H7), 4.97-4.89 (m, 1H, H1'), 4.86 (t, $^3$J=6.6 Hz, 1H, H2'), 4.81-4.79 (m, 1H, OH-5), 4.51 (dd, $^3$J=6.8 Hz and $^3$J=4.4 Hz, 1H, H3'), 3.49 (s, 2H, H5'), 2.95 (d, $^3$J=4.4 Hz, 3H, N—CH$_3$), 2.20-2.14 (m, 2H, H4', H6'A), 2.09-1.97 (m, 1H, H6'$_B$), 1.46 (s, 3H, CH$_3$), 1.21 (s, 3H, CH$_3$); APCI-MS(+): m/z 319.4 [M+H]$^+$.

7-((3aS,4R,6R,6aR)-6-(azidomethyl)-2,2-dimethyltetrahydro-4H-cyclopenta[d][1,3]dioxol-4-yl)-N-methyl-7H-pyrrolo[2,3-d]pyrimidin-4-amine (67). To a suspension of 66 (4.5 g, 13.9 mmol, 1 eq.) in dry dioxane (55 mL) at 0° C. were added DPPA (12.0 mL, 55.5 mmol, 4 eq.) and DBU (12.6 mL, 83.3 mmol, 6 eq.). The mixture was stirred at rt for 16 h. NaN$_3$ (4.6 g, 69.4 mmol, 5 eq.) and 15-crown-5 (2.9 mL, 13.9 mmol, 1 eq.) were added and the mixture was heated at 110° C. for 6 h. The organic phase was evaporated, water was added and the aqueous phase was extracted three times with AcOEt. The combined organic phase were dried over Na$_2$SO$_4$, filtered and evaporated. The residue was purified on silica gel column eluting with CH$_2$Cl$_2$/MeOH (99.5:05-96.5:3.5) to afford 67 (1.3 g, 3.9 mmol, 28%) as a yellow foam. C$_{16}$H$_{21}$N$_7$O$_2$ (343.39 g/mol). $^1$H-NMR (400 MHz, DMSO-d$_6$): δ 8.14 (s, 1H, H2), 7.47 (d, $^3$J=4.6 Hz, 1H, NH), 7.29 (d, $^3$J=3.6 Hz, 1H, H8), 6.56 (d, $^3$J=3.6 Hz, 1H, H7), 4.95 (dt, $^3$J=12.4 Hz and $^3$J=6.4 Hz, 1H, H1'), 4.89 (t, $^3$J=6.4 Hz, 1H, H2'), 4.51 (dd, $^3$J=7.2 Hz and $^3$J=5.2 Hz, 1H, H3'), 3.57-3.44 (m, 2H, H5'), 2.95 (d, $^3$J=4.6 Hz, 3H, N—CH$_3$), 2.35-2.20 (m, 2H, H4', H6'A), 2.12-1.97 (m, 1H, H6'$_B$), 1.47 (s, 3H, CH$_3$), 1.22 (s, 3H, CH$_3$); APCI-MS(+): m/z 344.4 [M+H]$^+$.

tert-butyl (7-((3aS,4R,6R,6aR)-6-(azidomethyl)-2,2-dimethyltetrahydro-4H-cyclopenta[d][1,3]dioxol-4-yl)-7H-pyrrolo[2,3-d]pyrimidin-4-yl)(methyl)carbamate (68). To a solution of 67 (566 mg, 1.63 mmol, 1 eq.) in dry THF (7.1 mL) with traces of DMF at 0° C. was added 60% suspended in oil NaH (163 mg, 4.08 mmol, 2.5 eq.). After 45 min stirring at rt, the solution was cooled down to 0° C. and Boc$_2$O (380 μL, 1.63 mmol, 1 eq.) was added. The mixture was stirred at rt for an extra 1.5 h. The mixture was cooled again to 0° C. and same amount of 60% suspended in oil NaH and Boc$_2$O were added sequentially. After 3 h at rt, full conversion was observed according to TLC. Cold brine was added and the aqueous phase was extracted three times with AcOEt. The combined organic phase were dried over Na$_2$SO$_4$, filtered and evaporated. The residue was purified on silica gel column eluting with CH$_2$Cl$_2$/MeOH (99.5:0.5-97.5:2.5) to afford 68 (537 mg, 1.21 mmol, 74%) as a orange oil. C$_{21}$H$_{29}$N$_7$O$_4$ (443.51 g/mol). $^1$H-NMR (400 MHz, DMSO-d$_6$): δ 8.62 (s, 1H, H2), 7.72 (d, $^3$J=3.6 Hz, 1H, H8), 6.45 (d, $^3$J=3.6 Hz, 1H, H7), 5.12 (dt, $^3$J=12.4 Hz and $^3$J=6.2 Hz, 1H, H1'), 4.92 (dd, $^3$J=7.2 Hz and $^3$J=6.2 Hz, 1H, H2'), 4.53 (dd, $^3$J=7.2 Hz and $^3$J=5.2 Hz, 1H, H3'), 3.60-3.46 (m, 2H, H5'), 3.35 (s, 3H, N—CH$_3$), 2.39-2.27 (m, 2H, H4', H6'$_A$), 2.17-2.05 (m, 1H, H6'$_B$), 1.49 (s, 3H, CH$_3$), 1.44 (s, 9H, CH$_3$ tBu), 1.23 (s, 3H, CH$_3$); APCI-MS(+): m/z 388.5 [M-tBu+2H]$^+$, 444.6 [M+H]$^+$.

tert-butyl (7-((3aS,4R,6R,6aR)-6-(aminomethyl)-2,2-dimethyltetrahydro-4H-cyclopenta[d][1,3]dioxol-4-yl)-7H-pyrrolo[2,3-d]pyrimidin-4-yl)(methyl)carbamate (69). To a solution of 68 (1.38 g, 3.08 mmol, 1 eq.) in AcOEt/MeOH (1:1, 10 mL) was added Pd/C (103 mg, 10% w/w). The suspension was put under H$_2$ and stirred at rt for 6 h, then filtered on Celite® pad and evaporated to afford the desired product (1.19 g, 2.84 mmol, 92%) as a dark grey oil. C$_{21}$H$_{31}$N$_5$O$_4$ (417.51 g/mol). $^1$H-NMR (400 MHz, DMSO-d$_6$): δ8.62 (s, 1H, H2), 7.75 (d, $^3$J=3.6 Hz, 1H, H8), 6.43 (d, $^3$J=3.6 Hz, 1H, H7), 5.08 (dt, $^3$J=12.4 Hz and $^3$J=6.2 Hz, 1H, H1'), 4.88 (t, $^3$J=6.8 Hz, 1H, H2'), 4.50 (dd, $^3$J=6.8 Hz and $^3$J=4.8 Hz, 1H, H3'), 3.34 (s, 3H, N—CH$_3$), 2.77-2.69 (m, 1H, H5'$_A$), 2.68-2.59 (m, 1H, H5'$_B$), 2.26 (dt, $^3$J=12.4 Hz and $^3$J=6.2 Hz, 1H, H6'$_A$), 2.18-2.07 (m, 1H, H4'), 2.06-1.95 (m, 1H, H6'$_B$), 1.47 (s, 3H, CH$_3$), 1.44 (s, 9H, CH$_3$ tBu), 1.22 (s, 3H, CH$_3$); APCI-MS(+): m/z 318.5 [M-Boc+2H]$^+$, 362.5 [M-tBu+H]$^+$, 418.7 [M+H]$^+$.

tert-butyl (S)-4-(((((3aR,4R,6R,6aS)-6-(4-((tert-butoxycarbonyl)(methyl)amino)-7H-purin[2,3-d]-2,2-dimethyltetrahydrofuro-4H-cyclopenta[d][1,3]dioxol-4-yl)methyl)amino)-2-((tert-butoxycarbonyl)amino)butanoate (70). To a stirred solution of 69 (400 mg, 0.96 mmol, 1.1 eq.) and 5

(240 mg, 0.87 mmol, 1 eq.) in dry DCE (7.5 mL) was added AcOH (55 µL, 0.96 mmol, 1.1 eq.). The solution was stirred for 3 h at rt, then NaBH(OAc)$_3$ (484 mg, 2.26 mmol, 2.6 eq.) was added and the mixture was stirred for 4 h at rt. After completion, the reaction was quenched by the addition of a 5% aq. NaHCO$_3$ solution and the phases were separated. The aqueous phase was then extracted 3 times with CH$_2$Cl$_2$ and the combined organic phases once with brine. Drying over Na$_2$SO$_4$, filtration and evaporation afforded the crude product that was subjected to silica gel column chromatography eluting with CH$_2$Cl$_2$/MeOH (99.4:0.6-95:5) to afford the secondary amine 70 (180.1 mg, 0.27 mmol, 31%) as a beige foam. C$_{34}$H$_{54}$N$_6$O$_8$ (674.84 g/mol). $^1$H-NMR (400 MHz; DMSO-d$_6$): δ 8.61 (s, 1H, H2), 7.74 (d, J=3.8 Hz, 1H, H8), 7.34 (d, J=7.2 Hz, 1H, NH Carbamate), 6.44 (d, J=3.8 Hz, 1H, H7), 5.08 (dt, J=12.4 Hz and J=6.2 Hz, 1H, H1'), 4.90 (t, J=6.6 Hz, 1H, H2'), 4.48-4.45 (m, 1H, H3'), 3.95-3.86 (m, 1H, Hα), 2.76-2.65 (m, 1H, H5'$_A$), 2.64-2.58 (m, 1H, Hγ$_A$), 2.56-2.50 (m, 2H, H5'$_B$, Hγ$_B$), 2.33-2.29 (m, 1H, H6'$_A$), 2.25-2.19 (m, 1H, H4'), 2.07-1.98 (m, 1H, H6'$_B$), 1.77-1.72 (m, 1H, Hβ$_A$), 1.71-1.64 (m, 1H, Hβ$_B$), 1.47 (s, 3H, CH$_3$), 1.44 (s, 9H, CH$_3$ tBu), 1.38 (s, 9H, CH$_3$ tBu), 1.28 (s, 9H, CH$_3$ tBu), 1.22 (s, 3H, CH$_3$).

General Procedure for the 2$^{nd}$ reductive amination (71) and the final deprotection (72). To a stirred solution of 70 (1.1 eq.) and an aldehyde 7 (1 eq.) in dry DCE (0.12 M based on 70) was added AcOH (1.1 eq.). The solution was stirred for 4 h at rt, then NaBH(OAc)$_3$ (2.6 eq.) was added and the mixture was stirred for 4 h at rt and 12 h at 70° C. After completion, the reaction was quenched by the addition of a 5% aq. NaHCO$_3$ solution and the phases were separated. The aqueous phase was then extracted 3 times with CH$_2$Cl$_2$ and the combined organic phases once with brine. Drying over Na$_2$SO$_4$, filtration and evaporation afforded the crude product that was subjected to silica gel column chromatography eluting with CH$_2$Cl$_2$/MeOH (mostly 99.5:0.5-94:6) to afford the tertiary amines 71 as yellow oils.

Tertiary amines 71 (or secondary amines 70) were dissolved (0.02 M) in freshly prepared TFA/H$_2$O (4:1) solution and stirred at rt for 6-16 h, then evaporated to give the desired products 72 as foams (2 or 3 TFA salt).

(S)-2-amino-4-((((1R,2R,3S,4R)-2,3-dihydroxy-4-(4-(methylamino)-7H-pyrrolo[2,3-d]pyrimidin-7-yl)cyclopentyl)methyl)amino)butanoic acid (72a)

Deprotection (72a): yield: 24.5 mg, 0.04 mmol, 100% (2 TFA salt). C$_{17}$H$_{26}$N$_6$O$_4$ (378.43 g/mol). $^1$H-NMR (400 MHz; DMSO-d$_6$): δ 9.52 (bs, 1H, NH), 8.68 (bs, 2H, NH$_2$$^+$), 8.48 (bs, 3H, NH$_3$$^+$), 8.36 (s, 1H, H2), 7.61 (s, 1H, H8), 6.90 (s, 1H, H7), 4.97-4.91 (m, 1H, H1'), 4.17 (t, J=6.6 Hz, 1H, H2'), 4.04 (s, 1H, Hα), 3.88 (t, J=5.2 Hz, 1H, H3'), 3.28-3.17 (m, 1H, H5'$_A$), 3.17-2.99 (m, 6H, H5'$_B$, Hγ, CH$_3$), 2.37-2.29 (m, 1H, H6'$_A$), 2.27-2.17 (m, 2H, H4', Hβ$_A$), 2.10-2.06 (m, 1H, Hβ$_B$), 1.64-1.56 (m, 1H, H6'$_B$); HRMS (ESI): calcd. for C$_{17}$H$_{27}$N$_6$O$_4$ [M+H]$^+$: 379.2088, found: 379.2092.

tert-butyl (S)-4-((((3aR,4R,6R,6aS)-6-(4-((tert-butoxycarbonyl)methyl)amino)-7H-pyrrolo[2,3-d]pyrimidin-7-yl)-2,2-dimethyltetrahydro-4H-cyclopenta[d][1,3]dioxol-4-yl)methyl)(3-((tert-butoxycarbonyl)(phenethyl)amino)propyl)amino)-2-((tert-butoxycarbonyl)amino)butanoate (71b) & (S)-2-amino-4-((((1R,2R,3S,4R)-2,3-dihydroxy-4-(4-(methylamino)-7H-pyrrolo[2,3-d]pyrimidin-7-yl)cyclopentyl)methyl)(3-(phenethylamino)propyl)amino)butanoic acid (72b)

Reductive amination (71b): yield: 101.5 mg, 0.108 mmol, 54%. C$_{50}$H$_{77}$N$_7$O$_{10}$ (936.21 g/mol). HIRMS (ESI): calcd. for C$_{50}$H$_{78}$N$_7$O$_{10}$ [M+H]$^+$: 936.5805, found: 936.5796.

Deprotection (72b): yield: 64 mg, 0.097 mmol, 100% (1 TFA salt). C$_{28}$H$_{41}$N$_7$O$_4$ (539.68 g/mol). $^1$H-NMR (400 MHz; DMSO-d$_6$): δ 9.44 (bs, 1H, CH$_3$—NH), 8.91 (bs, 2H, NH$_2$$^{(+)}$), 8.35 (s, 1H, H2), 7.58 (s, 1H, H8), 7.39-7.32 (m, 2H, m-H), 7.29-7.25 (m, 3H, o-H, p-H), 6.91 (s, 1H, H7), 5.00-4.89 (m, 1H, H1'), 4.15 (t, J=6.4 Hz, 1H, 12'), 4.02 (t, J=6.4 Hz, 1H, Hα), 3.87 (t, J=5.8 Hz, 1H, H3'), 3.37-3.18 (m, 9H, H5', Hγ, H1'', CH$_2$—N), 3.14-2.99 (m, 5H, H3'', CH$_3$), 2.97-2.86 (m, 2H, CH$_2$- Ph), 2.40-2.35 (m, 2H, H4', H6'$_A$), 2.28-2.21 (m, 1H, Hβ$_A$), 2.18-2.09 (m, 1H, Hβ$_B$), 2.09-1.96 (m, 2H, H2''), 1.68-1.61 (m, 1H, H6'$_B$); HRMS (ESI): calcd. for C$_{28}$H$_{42}$N$_7$O$_4$ [M+H]$^+$: 540.3293, found: 540.3293.

Synthesis of Compound 75b tert-butyl (3-(((((3aR,4R,6R,6aR))-6-(6-((tert-butoxycarbonyl)amino)-9H-cpurin-9-yl)-2,2-dimethyltetrahydrofuro[3,4-d][1,3]dioxol-4-yl)methyl)amino)propyl)(phenethyl)carbamate (73a) To a stirred solution of 4 (500 mg, 1.22 mmol, 1.1 eq.) and 7d (310 mg, 1.11 mmol, 1 eq.) in dry DCE (9 mL) was added AcOH (70 µL, 1.22 mmol, 1.1 eq.). The solution was stirred for 3 h at rt, then NaBH(OAc)$_3$ (616 mg, 2.88 mmol, 2.6 eq.) was added and the mixture was stirred for 3 h at rt. After completion, the reaction was quenched by the addition of a 5% aq. NaHCO$_3$ solution and the phases were separated. The aqueous phase was then extracted 3 times with CH$_2$Cl$_2$ and the combined organic phases once with brine. Drying over Na$_2$SO$_4$, filtration and evaporation afforded the crude product that was subjected to silica gel column chromatography eluting with CH$_2$Cl/MeOH (99.5:0.5-95.5:4.5) to afford the target compound (183 mg, 0.27 mmol, 25%). C$_{34}$H$_{49}$N$_7$O$_7$ (667.81 g/mol).

methyl (S)-4-((3-((tert-butoxycarbonyl)(phenethyl)amino)propyl)(((3aR,4R,6R,6aS)-6-(6-((tert-butoxycarbonyl)amino)-9H-purin-9-yl)-2,2-dimethyltetrahydrofuro[3,4-d][1,3]dioxol-4-yl)methyl)amino)-(2-((tert-butoxycarbonyl)amino)butanoate (74a) Compound 73a (181 mg, 0.27 mmol, 1.1 eq.) and 60 (57 mg, 0.24 mmol, 1 eq.) in dry DCE (2 mL) was added AcOH (16 µL, 0.27 mmol, 1.1 eq.). The solution was stirred for 3 h at rt, then NaBH(OAc)$_3$ (136 mg, 0.63 mmol, 2.6 eq.) was added and the mixture was stirred for 4 h at rt and 12 h at 70° C. After completion, the reaction was quenched by the addition of a 5% aq. NaHCO$_3$ solution and the phases were separated. The aqueous phase was then extracted 3 times with CH$_2$Cl$_2$ and the combined organic phases once with brine. Drying over Na$_2$SO$_4$, filtration and evaporation afforded the crude product that was subjected to silica gel column chromatography eluting with CH$_2$Cl$_2$/MeOH (99.5:0.5-95.5:4.5) to afford the target compound (31 mg, 0.035 mmol, 14%). C$_{44}$H$_{66}$N$_8$O$_{11}$ (883.06 g/mol). HRMS (ESI): calcd. for C$_{44}$H$_{67}$N$_8$O$_{11}$[M+H]$^+$: 883.4924, found: 883.4911.

methyl (S)-2-amino-4-((((2R,3S,4R,5R)-5-(6-amino-9H-purin-9-yl)-3,4-dihydroxytetrahydrofuran-2-yl)methyl)(3-(phenethylamino)propyl)amino)butanoate (75a). Compound 74a was then dissolved in 600 µL freshly prepared TFA/H$_2$O (4:1) solution and stirred at rt for 3 h, then evaporated to give the desired product 75a (14 mg, 0.026 mmol, 92%). C$_{26}$H$_{38}$N$_8$O$_5$ (542.64 g/mol). $^1$H-NMR (400 MHz, DMSO-d$_6$): δ 8.87 (s, 2H, NH$_2$), 8.73-8.51 (m, 4H, H2, NH$_3$$^+$), 8.50-8.31 (m, 2H, H8, NH), 7.35 (t, J=7.2 Hz, 2H, m-H), 7.28-7.24 (m, 3H, o-H, p-H), 6.01 (d, J=4.6 Hz, 1H, H1'), 4.62 (t, J=4.6 Hz, 1H, H2'), 4.42-4.31 (m, 1H, H4'), 4.24-4.20 (m, 1H, H3'), 4.19-4.14 (m, 1H, Hα), 3.71 (s, 3H, CH$_3$), 3.68-3.57 (m, 1H, H5'$_A$), 3.57-3.44 (m, 1H, H5'$_B$), 3.36-3.05 (m, 5H, Hγ, H1'', CH$_2$—N), 3.05-2.94 (m, 2H, H3''), 2.94-2.84 (m, 2H, CH$_2$-Ph), 2.27-2.17 (m, 1H, Hβ$_A$), 2.17-2.05 (m, 1H, Hβ$_B$), 2.04-1.91 (m, 2H, H2'').

tert-butyl (7-((3aS,4R,6R,6aR))-6-(((3-((tert-butoxycarbonyl)(3-phenoxyphenethyl)amino)propyl)amino)methyl)-2,2-dimethyltetrahydro-4H-cyclopenta[d][1,3]dioxol-4-yl)-7H-pyrrolo[2,3-d]pyrimidin-4-yl)(methyl)carbamate (73b). To a solution of aldehyde 7f (0.14 g, 0.356 mmol, 1 eq.) in dry MeOH (1.3 mL) was added 69 (0.158 g, 0.356 mmol, 1 eq.) in 0.5 mL of dry MeOH dropwise and the mixture was stirred overnight at rt. After cooling to 0° C. NaBH$_4$ (0.022 g, 0.54 mmol, 1.5 eq) was added. The reaction was stirred at rt until the bubbling stops, then the solvent was evaporated and the residue was partitioned between water and AcOEt. The aqueous phase was extracted with AcOEt (3 times). The combined organic phases were dried over Na$_2$SO$_4$, dryed and the solvent was removed under vacuum. The resulting product was purified via flash chromatography using DCM/MeOH (100/0 to 80/20) to afford the final product as a yellow oil (0.05 g, 0.065 mmol, 17.4%). C$_{43}$H$_{58}$N$_6$O$_7$ (770.97 g/mol). $^1$H-NMR (400 MHz, DMSO-d$_6$): δ 8.61 (s, 1H, H2), 7.73 (d, 1H, H8), 7.37 (t, 2H, m"-H), 7.26 (t, 1H, m-H), 7.11 (t, 1H, p"-H), 6.97 (t, 3H, o"-H, o"-H), 6.82 (d, 2H, p-H, o'-H), 6.43 (d, 1H, H7), 5.10-5.03 (m, 1H, H1'), 4.89 (t, 1H, H2'), 4.48 (t, 1H, H3'), 3.51-3.46 (m, 1H), 3.43-3.37 (m, 2H, C$\underline{H}_2$—N), 3.20-3.05 (m, 3H, N—C$\underline{H}_3$), 2.76-2.69 (m, 3H, C$\underline{H}_2$-Ph, H5'$_A$), 2.68-2.65 (m, 1H, H5'$_B$), 2.34-2.31 (m, 1H, H6'$_A$), 2.29-2.15 (m, 2H, H4',), 2.09-1.93 (m, 2H, H6'$_B$), 1.59 (m, 2H), 1.47 (s, 3H, C$\underline{H}_3$), 1.43 (s, 9H, C$\underline{H}_3$ tBu), 1.32 (d, 9H, C$\underline{H}_3$ tBu), 1.23 (s, 1H), 1.21 (s, 3H, C$\underline{H}_3$).

methyl (S)-2-amino-4-((3-((tert-butoxycarbonyl)(3-phenoxyphenethyl)amino)propyl)(((3aR,4R,6R,6aS)-6-(4-((tert-butoxycarbonyl)(methyl)amino)-7H-pyrrolo[2,3-d]pyrimidin-7-yl)-2,2-dimethyltetrahydro-4H-cyclopenta[d][1,3]dioxol-4-yl)methyl)amino)butanoate (74b). To a stirred solution of 73b (0.050 g, 0.064 mmol, 1 eq.) and 14 (0.015 g, 0.064 mmol, 1 eq.) in dry DCE (1 mL) was added AcOH (4 μL, 0.071 mmol, 1.1 eq.). The solution was stirred for 4 h at rt, then NaBH(OAc)$_3$ (0.04 g, 0.17 mmol, 2.6 eq.) was added and the mixture was stirred for 4 h at rt and 12 h at 70° C. After completion, the reaction was quenched by the addition of a 5% aq. NaHCO$_3$ solution and the phases were separated. The aqueous phase was then extracted 3 times with CH$_2$Cl$_2$ and the combined organic phases once with brine. Drying over Na$_2$SO$_4$, filtration and evaporation afforded the crude product that was subjected to silica gel column chromatography eluting with CH$_2$Cl$_2$/MeOH (99.5:0.5-90:10) to afford the target compound (3 mg, 0.003 mmol, 4.7%). C$_{53}$H$_{75}$N$_7$O$_{11}$ (986.22 g/mol).

methyl (S)-2-amino-4-((((1R,2R,3S,4R)-2,3-dihydroxy-4-(4-(methylamino)-7H-pyrrolo[2,3-d]pyrimidin-7-yl)cyclopentyl)methyl)(3-((3-phenoxyphenethyl)amino)propyl)amino)butanoate (75b). 74b was then dissolved in 500 μL freshly prepared TFA/H$_2$O (4:1) solution and stirred at rt for 6-16 h, then evaporated to give the desired product 74b (5.6 mg, 0.006 mmol, 100%). C$_{35}$H$_{47}$N$_7$O$_5$ (645.81 g/mol). $^1$H-NMR (400 MHz, DMSO-d$_6$): δ9.00-8.93 (m, 2H), 8.72-8.64 (m, 3H), 8.35-8.27 (m, 1H), 7.55-7.50 (m, 1H), 7.38-7.26 (m, 3H), 7.12-7.05 (m, 2H), 7.01-6.91 (m, 2H), 6.89-6.85 (m, 1H), 6.85-6.80 (m, 1H), 5.26-5.24 (m, 1H), 4.88-4.85 (m, 1H), 4.18-4.12 (m, 1H), 4.10-4.05 (m, 1H), 3.82-3.78 (m, 1H), 3.69 (s, 3H), 3.24-3.05 (m, 5H), 3.05-2.96 (m, 3H), 2.86-2.82 (m, 2H), 2.30-2.06 (m, 5H), 2.02-1.86 (m, 3H), 1.61-1.54 (m, 2H), 1.41-1.36 (m, 1H).

Compound 72b has the following structure:

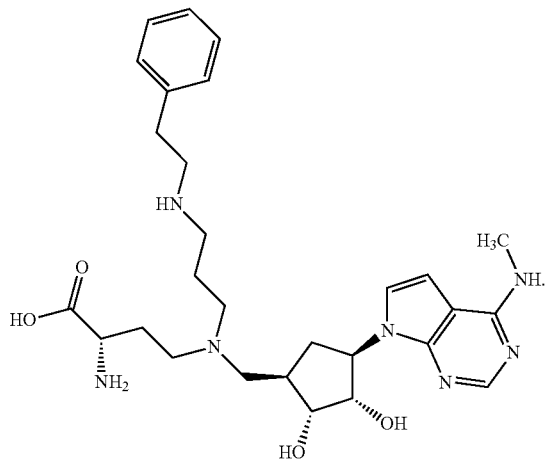 [SMILES: CNc1ncnc2c1ccn2[C@@H]1C[C@H](CN(CCCNCCc2ccccc2)CC[C@H](N)C(=O)O)[C@@H](O)[C@H]1O]

Compound 75b has the following structure:

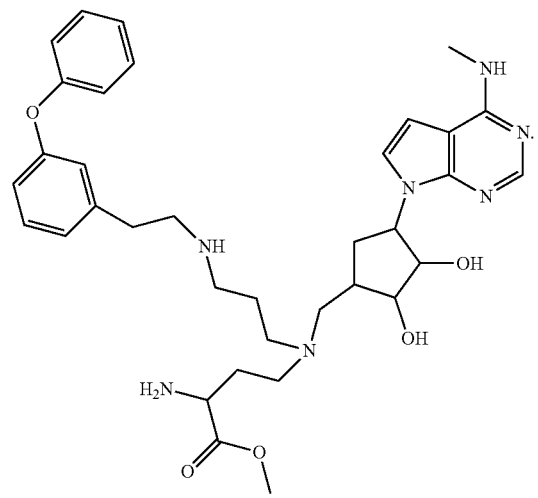 [SMILES: CNc1ncnc2c1ccn2C1CC(CN(CCCNCCc2cccc(Oc3ccccc3)c2)CCC(N)C(=O)OC)C(O)C1O]

4.10. Example 10: Testing of Compound 72b for KMT9-Inhibition, KMT9-Binding and KMT9-Specificity Methylation Assay to Test KMT9-Inhibition by Compounds of the Present Invention Methylation assays were performed to test inhibition of the KMT9 methyltransferase activity by compound 72b. To test the compound, 1 μL of the compound, dissolved in DMSO at different concentrations, was added to a 0.5 ml tube (Brand Gmbh&Co KG). Afterwards, 4 μL of assay buffer (50 mM BTP, 1 mM MgCl2, 1 mM DTT, 0.01% TX-100, pH 8.5) were added together with 10 μL of 2× solution of KMT9 diluted in assay buffer (final concentration 0.025-0.6 μM). The solutions were mixed and incubated for 20 min at room temperature, shaking at 300 rpm. Afterwards, 5 μL of 4× Protein-SAM mix was added (final concentrations: 5 μM ETF1 or histone H4, SAM: 1-2.5 μM (including 30% of radioactively labelled [3H]SAM)) to a final assay volume of 20 μL. The reaction mixtures were mixed and incubated in an Eppendorf thermomixer comfort for 2 h at 30° C., shaking at 300 rpm. The reaction was quenched using 5 µL of 50% trichloroacetic acid (TCA) in water, mixed and incubated for 5 min at room temperature without shaking. 22 µL of the solution was transferred to a filter binding plate (MultiScreenHTS FB Filter Plate, 1.0/0.65 µm, opaque, non-sterile, Merck KGaA Darmstadt), vacuum filtered using MultiScreen®HTS Vacuum Manifold (Merck KGaA Darmstadt) and washed with 4×50 µL TCA 10% followed by 2×50 µL ethanol 100%. After air-drying overnight, the filters were transferred to individual scintillation vials; 3 mL of Ultima Gold (PerkinElmer) was added and shook for 1 h. The scintillation signal was measured for 3×1 min using Tri-Carb 2910 TR (PerkinElmer) scintillation counter in [$^3$H] CPM mode. The obtained $IC_{50}$-value of the tested compound is shown in the table below as follows: $IC_{50}$-value >10 µM is denoted with a "+", $IC_{50}$-value from 10 µM to 100 nM is denoted with "++", and $IC_{50}$-value <100 nM is denoted with "+++".

Microscale Thermophoresis (MST) to Test KMT9-Binding by Compounds of the Present Invention To determine the binding affinity of the compound to KMT9, microscale thermophoresis (MST) analysis was performed with a NanoTemper Monolith NT.115 instrument (NanoTemper Technologies GmbH). KMT9 was labelled with a RED-Tris-NTA labelling kit (NanoTemper Technologies GmbH) based on the manufacturer's instructions. Buffer including 25 mM HEPES (pH 7.5), 100 mM NaCl, 1 mM DTT and 0.05% Tween was used for the reaction buffer. Varying concentrations of the compound were titrated against His-tag labelled KMT9 proteins (20 nM). Samples were loaded into standard Capillaries (NanoTemper Technologies GmbH) and MST measurements were performed using 40% MST power and 100% LED power. For each set of binding experiments, MST measurement was carried out with Binding Affinity module in MO. Control program under Nano-RED Excitation. Datasets were processed with the MO. Affinity Analysis software (NanoTemper Technologies GmbH). The obtained binding affinity of the tested compound is shown in the table below as follows: binding affinity >10 µM is denoted with a "+", binding affinity from 10 µM to 100 nM is denoted with "++", and binding affinity <100 nM is denoted with "+++".

Thermal Shift Assay to Test the Increase in Thermal Stability of KMT9 Upon Inhibitor Binding For inhibitor testing, 1 µL of the compound, dissolved in DMSO at different concentrations, were added to a 96 well hard-shell PCR plate (Bio-Rad). Afterwards 4 µL of assay buffer (50 mM BTP, 1 mM MgCl2, 1 mM DTT, pH 8.5) were added, followed by 10 µL of 2×KMT9 (final concentration 2 µM) in assay buffer. After addition of 5 µL 4×SYPRO-Orange (Sigma) (final concentration 5×), the plate was spun for 1 min at 700 rpm, then shaken at 600 rpm for 15 minutes. After another 5 spinning at 700 rpm for 1 min, measurement was performed using a CFX96 Touch Real-Time PCR Detection System (Bio-Rad). The plate was equilibrated at 20° C. for 4 minutes before heating gradually by 1° C. every 15 seconds until 95° C. After every step, the fluorescence was measured in FRET mode. The thermal shift at 500 µM is detected in K (Kelvin). For Example 9o, the thermal shift at 250 µM is detected in K (Kelvin). The obtained thermal shift obtained by adding the tested compound is shown in the table below as follows: shift ≤5 K is denoted with a "+", shift >5 and ≤15 K is denoted with "++", and shift >15 K is denoted with "+++".

| Compound number | IC50-value in methylation assay | Binding affinity in MST | Thermal shift upon KMT9 binding |
|---|---|---|---|
| 72b | +++ | +++ | ++ |

Thus, compound 72b is a potent small molecule inhibitor of KMT9.

Compound 72b was further tested against a plurality of methyltransferases as described in the following. Thus, compound 72b was tested against the methyltransferases as indicated in the table below, wherein the compound was tested in a 10-dose IC50 mode with 3-fold serial dilution, in singlet, starting at 10 µM. Control compounds, namely SAH (S-(5'-Adenosyl)-L-homocysteine), Chaetocin, LLY 507, or Ryuvidine (as also indicated in the table below) were tested in 10-dose IC50 mode with 3-fold serial dilution starting at 100 or 200 µM. Reactions were carried out at 1 µM SAM. Curve fits were performed where the enzyme activities at the highest concentration of compounds were less than 65%. Empty cells indicate no inhibition or compound activity that could not be fit to an IC50 curve. Compound 72b is referred to as KMI9542321 in the table below.

| Methyl-transferase: | Substrate: | Compound IC50* (M) KMI9542321 | Control IC50* (M): | Control ID: |
|---|---|---|---|---|
| KMT9 | Histone H4 | 2.00E−07 | | |
| DOT1L | Nucleosomes | | 3.68E−07 | SAH |
| Target2 | Core Histone | | 2.64E−05 | SAH |
| PRMT1 | Histone H4 | | 2.71E−07 | SAH |
| PRMT3 | Histone H4 | | 1.88E−06 | SAH |
| PRMT4 | Histone H3 | | 2.61E−07 | SAH |
| PRMT5/MEP50 Complex | Histone H2A | | 1.01E−06 | SAH |
| PRMT5(C449S)/MEP50 Complex | Histone H2A | | 3.96E−06 | SAH |
| PRMT6 | GST-GAR | | 1.99E−07 | SAH |
| PRMT7 | GST-GAR | | 1.05E−07 | SAH |
| PRMT8 | Histone H4 | | 1.27E−07 | SAH |
| S-COMT | RBC-DA1 | | 5.88E−10 | Tolcapone |
| S-COMT (V108M) | RBC-DA1 | | 6.83E−10 | Tolcapone |
| ASH1L | Nucleosomes | | 2.74E−08 | Chaetocin |
| DNMT1 | Poly (dI-dC) | | 2.62E−07 | SAH |
| DNMT3a | Lambda DNA | | 3.29E−07 | SAH |
| DNMT3b | Lambda DNA | | 3.52E−08 | SAH |
| DNMT3b/3L | Lambda DNA | | 3.21E−08 | SAH |
| EZH1 Complex | Core Histone | | 1.07E−05 | SAH |
| EZH2 Complex | Core Histone | | 2.01E−05 | SAH |
| EZH2 (Y641F) Complex | Core Histone | | 6.47E−05 | SAH |
| G9a | Histone H3 (1-21) | | 2.94E−06 | SAH |
| GLP | Histone H3 (1-21) | | 1.21E−06 | SAH |
| MLL1 Complex | Nucleosomes | | 1.17E−06 | SAH |
| MLL2 Complex | Nucleosomes | | 1.84E−05 | SAH |
| MLL3 Complex | Core Histone | | 2.54E−05 | SAH |
| MLL4 Complex | Nucleosomes | | 1.79E−06 | SAH |
| NRMT1 | RCC1 | | 1.07E−06 | SAH |
| NRMT2 | RCC1 | | 6.43E−07 | SAH |
| NSD1 | Nucleosomes | | 4.33E−06 | SAH |
| NSD2 | Nucleosomes | | 3.05E−06 | SAH |
| NSD2 (E1099K) | Nucleosomes | | 1.57E−06 | SAH |
| NSD2 (T1150A) | Nucleosomes | | 1.44E−06 | SAH |
| NSD3 | Nucleosomes | | 5.88E−08 | Chaetocin |
| PRDM9 | Histone H3 | | 3.54E−07 | Chaetocin |
| SET1b Complex | Core Histone | | 5.27E−06 | SAH |
| SET7/9 | Core Histone | | 2.81E−04 | SAH |

-continued

| Methyl-transferase: | Substrate: | Compound IC50* (M) KMI9542321 | Control IC50* (M): | Control ID: |
|---|---|---|---|---|
| SET8 | Nucleosomes | | 7.75E−07 | Ryuvidine |
| SETD2 | Nucleosomes | | 4.08E−06 | SAH |
| SMYD2 | Histone H4 | | 2.71E−07 | LLY 507 |
| SMYD3 | MEKK2 | | 1.29E−05 | SAH |
| SUV39H1 | Histone H3 | | 6.57E−05 | SAH |
| SUV39H2 | Histone H3 | | 1.02E−04 | SAH |
| SUV420H1TV2 | Nucleosomes | | 1.39E−04 | SAH |

These data clearly show that compound 72b is specific for KMT9-inhibition. Thus, compound 72b is a potent small molecule inhibitor of KMT9, which is selective for KMT9.

4.11. Example 11: Proliferation Block of Cancer Cells by Addition of a Small Molecule Inhibiting KMT9

Compound 75b is assumed to correspond to a prodrug and is an example of compounds that can directly be used in cells since they are membrane-permeable. Upon entering the cell, the ester-moiety (here a methyl-ester) is cleaved by cellular esterases, resulting in the acid-moiety found in compound 72b that is active and selective in vitro (see above example 4.10).

Compound 75b was tested in a proliferation assay in cell culture as described in the following. Thus, compound 75b (alternatively referred to as "KMI95423411") was added to a final concentration of 30 µM (in the controls, DMSO as added) to cells of the following cell lines: LNCaP, SW-480, A549, MDA-MB-468 and HepG2, and the cells were cultured in the presence of inhibitor or DMSO. At the time points indicated in FIG. 15, the cells were seeded in E-plates and the cell proliferation was determined using the xCelligence RTCA system (Roche) as described below. As can be derived from FIG. 15, compound 75b blocks proliferation of LNCaP prostate tumour cells, SW-480 colorectal cancer cells, MDA-MB-468 breast cancer cells, and A549 lung tumour cells. KMI95423411 does not affect proliferation of the KMT9 non-responsive HepG2 cells.

This example shows that small molecule inhibitors of KMT9 are capable of blocking the proliferation of cancer cell lines in a cellular assay.

4.12. Experimental Procedures Used in the Above Examples

Plasmids

His-C21orf127(N122A) and His-C21orf127(Y125A) (His-KMT9αY125A) were obtained by site directed mutagenesis. To construct expression plasmids for His-TRMT112 (His-KMT9β), His-C21orf127 (His-KMT9α), His-C21orf127/TRMT112 (His-KMT9α/KMT9β), His-C21orf127(D103A)/TRMT112 (His-KMT9α(D103)/KMT9β), His-C21orf127(N122A)/TRMT112 (His-KMT9α(N122A)/KMT9β), His-C21orf127(Y125A)/TRMT112 (His-KMT9α(Y125A)/KMT9β), His-TRMT12, His-TRMT11, His-TRMT5, His-KIAA1456, His-WBSCR22/TRMT112, His-METTL27, His-ETF1, His-METTL21A and His-METTL21B the corresponding cDNA fragments, obtained from GeneCopoeia, were cloned into pDEST17 or pET-Duet1. For crystallisation, His-TEV-C21orf127 and TRMT112 were cloned into Pet-Duet1. pET-H4K12A-His was obtained by site directed mutagenesis of pET-H4-His.

To construct pLenti6-miRNA KMT9α, the DNA corresponding to miRNA KMT9α (5'-TGCTGATGT-GAACTTTGTTACAGCGTGTTTTGGC-CACTGACTGACACGCT GTAAAAGTTCACAT-3' [SEQ ID NO:1] and 5'-CCTGATGTGAACTTTTA-CAGCGTGTCAGTCAGTGGCCAA AACACGCTGTA ACAAAGTTCACATC-3' [SEQ ID NO:2]) was cloned into pLenti6/V5-DEST according to the manufacturer's instruction (Life Technologies). pLenti LacZ (plenti7.3/V5-GWlacz) was obtained from Life Technologies. pLenti KMT9α, KMT9α(N122A), KMT9αY125A), and ETF1 were obtained by cloning the corresponding cDNAs into pLenti7.3-V5-DEST-EmGFP. pET-hH4-His was obtained from R. Schneider.

Cell Culture

All cell lines used herein were cultured according to standard methods. PC-3M (PC-3M-luc2, Caliper Life Sciences), LNCaP (LNCaP-luc2, Caliper Life Sciences), C4-2B, PNT2, LAPC4, LNCaP-abl, LAPC4 EnzaR, LNCaP-abl EnzaR, and DuCaP EnzaR were cultured in RPMI 1640. DU145 and Caco-2 were cultured in EMEM. HT-29, SK-N-SH, SW620, SW480, HT-29, HT-115, HCT116 p53+/+ and HCT p53−/− were cultured in DMEM. All media were supplemented with 10% foetal calf serum, penicillin/streptomycin, and glutamine (except for HT-29 and HT-115, where 15% foetal calf serum was used). RWPE1 were cultured in keratinocyte SFM (Life Technologies, cat #17005-042). The culture media for LAPC4 EnzaR, DuCAP EnzaR, and LNCaP-abl EnzaR were supplemented with 8 µM and 13 µM enzalutamide (MDV 3100, Cayman Chemical), respectively. LAPC4, LAPC4 EnzaR, DuCaP EnzaR, LNCaP-abl, and LNCaP-abl EnzaR were gifts from Z. Culig and are described[5].

Protein Expression and Purification

For protein expression of His-C21orf127/TRMT112 (His-KMT9α/KMT9β), His-C21orf127(D103A)/TRMT112 (His-KMT9αD103A)/KMT9β), His-C21orf127(N122A)/TRMT112 (His-KMT9α(N122A)/KMT9β), His-C21orf127(Y125A)/TRMT112 (His-KMT9α(Y125A)/KMT9β), His-C21orf127 (His-KMT9α), His-TRMT112 (His-KMT90), His-WBSCR22/TRMT112, His-TRMT11, His-TRMT12, His-KIAA1456, His-TRMT5, His-METTL27, H4-His, H4K12A-His, His-ETF1, His-METTL21A and His-METTL21B the corresponding plasmids were transformed into BL21-CodonPlus-RIPL. Protein expression was performed overnight at 16 or 18° C. in presence of 0.4-1 mM IPTG. Bacterial pellets were resuspended in Binding Buffer 1 (25 mM Tris-HCl pH 8.0, 200 mM NaCl, 5% glycerol, 10 mM imidazole pH 8.0, 5 mM beta-mercaptoethanol, cOmplete™ EDTA-free Protease Inhibitor Cocktail (Roche)) and disrupted with an EmulsiFlex (Avestin). Lysates were clarified by centrifugation and incubated with 5 ml Ni-NTA fast flow resin (Qiagen) for 45 min at 4° C. The resin was loaded into a gravity flow column (Bio-Rad), washed with 100 ml Wash Buffer (25 mM Tris-HCl pH 8.0, 200 mM NaCl, 5% glycerol, 20 mM imidazole pH 8.0, 5 mM beta-mercaptoethanol) and proteins were eluted with Buffer 2 (25 mM Tris-HCl pH 8.0, 200 mM NaCl, 5% glycerol, 250 mM imidazole pH 8.0, 5 mM beta-mercaptoethanol). Finally, the eluted fractions were dialyzed against 10 mM Tris-HCl pH 8.0, 100 mM NaCl, 20% glycerol, 2 mM DTT. Proteins were aliquoted, flash frozen in liquid nitrogen, and stored at −80° C.

For purification of H4-His and H4K12A-His, bacterial pellets were resuspended in sonication buffer (PBS, 1 mM DTT, 0.2 mg/ml lysozyme, 0.05 mg/ml DNAseI, cOmplete™ EDTA-free Protease Inhibitor Cocktail), disrupted by sonication, and pelleted. Pellets were resuspended in Wash Buffer (PBS, 1% Triton X-100, 1 mM DTT) and centrifuged twice followed by a final wash and centrifugation step using Wash Buffer devoid of Triton X-100. Subsequently, pellets were macerated in 1 ml DMSO for 30 min at room temperature, resuspended by addition of 10 ml extraction buffer and incubated for 60 min at 37° C. Upon centrifugation, supernatants were incubated with Ni-NTA fast flow resin (Qiagen) for 120 min at 4° C. Following centrifugation, resin was washed with Urea Washing Buffer pH 6.2 (8 M urea, 100 mM NaH2PO4, 1 mM DTT). Proteins were eluted with Urea Elution Buffer pH 4.5 (7M urea, 20 mM NaOAC, 200 mM NaCl, 1 mM DTT) and dialyzed against Dialyse Buffer 1 (50 mM Tris-HCl, 5 mM beta-mercaptoethanol) followed by a second dialysis against Dialyse Buffer 2 (50 mM Tris-HCl). Proteins were aliquoted, flash frozen in liquid nitrogen, and stored at −80° C. For crystallization, pET-Duet1-His-TEV-C21orf127/TRMT112 was transformed into BL21-CodonPlus-RIPL. Bacterial pellets were resuspended in Binding Buffer 1 and disrupted with an EmulsiFlex. Lysates were clarified by centrifugation and were firstly purified with 5 ml Ni-NTA column (Qiagen). The His tag was cleaved off by TEV protease digestion overnight during dialysis in 25 mM Tris-HCl pH 8.0, 100 mM NaCl, 5% glycerol, 2 mM beta-mercaptoethanol. The protein complex was further purified by over a HiTrap Q HP anion exchange chromatography column and (GE healthcare) and a HiLoad 16/600 Superdex 75 column (GE healthcare). Proteins were concentrated to 25 mg/ml in gel filtration buffer (20 mM Tris-HCl pH 8.0, 100 mM NaCl, 5% glycerol, 2 mM DTT), aliquoted, flash frozen in liquid nitrogen and stored at −80° C.

Chromatin Immunoprecipitation and Sequencing (ChIP-Seq)

ChIP experiments were performed essentially as previously described[26]. LNCaP and PC-3M cells were cultured as described above. Three days before harvesting, cells were transfected with siCtrl, siKMT9α, or siKMT9β using Dharmafect2 (Thermo Scientific) following the manufacturer's instructions. Immunoprecipitation was performed with specific antibodies (anti-KMT9α, (#27630, lot 20062017, Schüle Lab); anti-H4K12me1 (#27429, lot 27062017, Schüle Lab); anti-KMT9β (#28358, lot 27022018, Schüle Lab); anti-H4K20me3 (#C15410207, lot A2730P, Diagenode) in presence of spike-in chromatin (#53083, Active Motif) on GammaBind™G-Sepharose™ (GE-Healthcare). Libraries were prepared from immunoprecipitated DNA according to standard methods. ChIP-seq libraries were sequenced using a HiSeq 2000 (Illumina) at the sequencing core facility of the MPI-IE, Freiburg. Reads were aligned to the hg19 build of the human genome using STAR version 2.5[27]. Data were further analysed using the peak finding algorithm MACS 1.42[28] using input as control. All peaks with FDR greater than 10% were excluded from further analysis. The reads were used to generate the genome-wide intensity profiles, which were visualized using the IGV genome browser[29]. HOMER[30] was used to annotate peaks (annotatePeaks.pl) and to calculate overlaps between different peak files (mergePeaks). The genomic features (promoter, exon, intron, 3'UTR, and intergenic regions) were defined using Refseq. Seqplots (http://seqplots.ga/) was used to visualize the signals in heatmaps.

Western Blot Analysis

Experiments were performed as previously described[26]. Three days before harvesting, cells were transfected with siRNA as indicated. The following antibodies were used: anti-KMT9α (#27630, lot 20062017, Schüle Lab, FIG. 2a, 4m, Extended Data FIGS. 2e, 4f-m); anti-KMT9α (HEMK2 (N-18), #sc83304, lot J2708, Santa Cruz, FIGS. 2e, 4c-f, i, and Extended Data FIG. 4a-e, n); anti-KMT9α (#ab88898, abeam, Extended Data FIG. 2f); anti-KMT9β (#28358, lot 27022018, Schüle Lab), anti-ETF1 (#ab31799, lot GR314950-1, Abcam), anti-H4K12me1 (#27429, lot 27062017, Schüle Lab); anti-tubulin (alpha tubulin, #T6074, lot 03714804V, Sigma); anti-actin (#A1978, lot 012M4821, Sigma); anti-H4K20me1 (Active Motif, #39727); anti-METTL21A (anit-FAM119A, Novus Biological, #NBP1-83282); anti-GAPDH (clone 6C5, Millipore, MAB374); anti-H4 (Abcam, ab10158); anti-LMNA (Lamin A; Abcam, ab26300).

Anti-ETF1me is a gift from A. Jeltsch and was previously described[20]. The peptides H4 aa1-21K12me0/1/2, H4 aa49-69K59me0/1/2, H4 aa83-99K91me0/1/2, H4 aa72-84K79me0/1/2, H3 aa1-21K4me0/1/2/3 and H3K9me0/me1/me/me3 were obtained from PSL Peptide Specialty Laboratories GmbH. H4 aa15-20me0/me1/me2/me3 (#C16000995, #C16000034, #C16000138, #C16000057), H3 aa20-35K27me0/me1/me2/me3 (#C16000998, #C16000045, #C16000046, #C16000069), H3 aa29-43 K36 (#C16000997, #C16000089, #C16000127, #C16000058) peptides were obtained from Diagenode.

Methylation Assay

Four to eight μg of purified recombinant His-C21orf127, His-C21orf127/TRMT112, His-C21orf127(D103A)/TRMT112, His-C21orf127(N122A)/TRMT112, His-C21orf127(Y125A)/TRMT112, His-TRMT112, WBSCR22/TRMT112, His-TRMT11, His-TRMT12, His-KIAA1456, His-TRMT5, His-METTL27, His-METTL21A and His-METTL21B were incubated either with 4 μg core histones or 2 μg of histones H4, H3, H2A, H2B, H1 (BPS Bioscience), histone H4K12A, or His-ETF1 as indicated in methylation buffer (10 mM Tris-HCl pH 7.6, 50 mM KCl, 10 mM Mg(OAc)2, 1 mM DTT) supplemented as indicated with 1.5 μM SAM or 1.5 μl of radioactively labelled [³H]SAM for 60 min (METTL21A: 300 minutes, METTL21B: 18 h) at 30° C. For mass spectrometry analysis, 2 μg of histone H4 were incubated overnight with 2 μg of His-C21orf127/TRMT112 in presence of SAM, heavy SAM, or SAM/heavy SAM mixture. The reaction mixture was analysed by autoradiography, Western blotting, or mass spectrometry. For METTL21A and METTL21B, the analysis was carried out by autoradiography or Ponceau red staining as indicated in the figures.

Cell Proliferation, Migration and Invasion Assay

Cell proliferation, migration and invastion were determined using the X-Celligence RTCA system (Roche). pLenti-LacZ, pLenti-KMT9α, pLenti-KMT9α(N122A), pLenti-KMT9α(Y125A) pLenti-ETF1, pLenti-shLaZ, and pLenti-shKMT9α constructs were used to produce recombinant lentiviruses to infect LNCaP and PC-3M cells as described in Metzger et al., 2005. For real-time recording of LNCaP, LNCaP-abl, LNCaP-abl EnzaR, and C4-2B cell proliferation, 20000 cells/well were seeded in 16 well E-plates (Roche). For PC-3M, 2500 cells/well were used. For DuCaP EnzaR, LAPC4 and LAPC4 EnzaR, 40000 cells/well were used. Cells were transfected with the indicated siRNAs in presence of Dharmafect 1 (LNCaP-abl, LAPC4, LAPC4 EnzaR; Dharmacon), Dharmafect 2 (LNCaP, PC-3M), or RNAiMAx (C4-2B, LNCaP-abl EnzaR, DuCaP EnzaR; Caco-2, HT-29, SK-N-SH, SW620, SW480, HT-29, HT-115, HCT116 p53+/+ and HCT p53−/−; Life Technologies) 24 h before seeding in E-plates. Cell indices were automatically recorded every 15 minutes. Relative velocities represent the change of the cell index over time. The sequences of the siRNAs (Stealth RNAi™ siRNAs; Life Technologies) used in the experiments are as following: siCtrl:

[SEQ ID NO: 3]
5'-AAAGUCCUAGAUCCACACGCAAAU-3';

siKMT9α-3'-UTR:
[SEQ ID NO: 4]
5'-GGAACUACAUUAGACUUAGUGGAAA-3';

siKMT9α#1:
[SEQ ID NO: 5]
5'-ACGCUGUAACAAAGUUCACAUUCAA-3';

siKMT9α#2:
[SEQ ID NO: 6]
5'-CACGCUGUAACAAAGUUCACAUUCA-3';

siKMT9β:
[SEQ ID NO: 7]
5'-CCUGCUGCUGGAGGUGGAAUU-3',

[SEQ ID NO: 8]
5'-UUCCACCUCCAGCAGCAGGUG-3';

siRNA METTL21A
(identical to METTL21A#1):
[SEQ ID No. 9]
5'-CCACGGAAUUUGGGUUGCAGAAAUU-3';

siRNA METTL21B#1:
[SEQ ID No. 10]
5'-GGACAGAGAGCUUCUUUCAGCACCU-3';

siRNA METTL21B#2
[SEQ ID No. 11]
5'-CCAUCAUGUCUUCCCUGCAAACUAU-3';

siMETTL21A#2:
5'-GCCGAAUUCGCUAUGAACGGGAUAA-3'.

Growth of Xenograft Tumours in NOD/SCID Mice; Rosa26Cre/ERT2 and AOM/DSS Mouse Model pLenti6-miRNA Control and pLenti6-miRNA KMT9α constructs were used to produce recombinant lentiviruses to infect LNCaP, PC-3M and LAPC4 EnzaR cells as described[26]. Five-week-old male severe combined immunodeficient mice were purchased from Charles River Laboratories. For tumour inoculation $5\times10^6$ LNCaP, $2\times10^6$ PC-3M, and $5\times10^6$ LAPC4 EnzaR cells infected with pLenti6-miRNA Control or pLenti6-miRNA KMT9α constructs were injected in NOD/SCID mice, respectively. Mice were castrated one week before injection of LAPC4 EnzaR. Cells were resuspended in 100 µl RPMI1640 mixed with 100 µl Matrigel (BD Biosciences) on ice and administered subcutaneously in the flank of each animal. The tumour size was determined by calliper measurements two times a week[24]. Tumour volumes were calculated using the formula 4/3×π× r3. All experiments were performed according to the German Animal Protection Law with permission from the responsible local authorities.

The Rosa26Cre/ERT2 as a system for a conditional gene inactivation using the Cre/loxP system and a specific mouse strain expressing Cre-ER$^T$ from the ROSA26 locus are generally described in Vooijs et al., (2001); EMBO reports, vol. 2; no. 4, 292-297. The relevant background information on the AOM/DSS murine model for the study of colorectal carcinogenesis can be found in De Robertis et al., (2011); J. Carcinog. 10:9 (doi: 10.4103/1477-3163.782679).

RNA Sequencing (RNA-seq)

Three days before harvesting for RNA-seq cells were transfected with siRNA as indicated. RNA was isolated as previously described[31]. RNA samples were sequenced by the standard Illumina protocol to create raw sequence files (.fastq files) at the sequencing core facility of the DKFZ, Heidelberg. Reads were aligned to the hg19 build of the human genome using STAR version 2.5[27]. The aligned reads were counted with the homer software (analyzeRepeats) and differentially expressed genes were identified using EdgeR[32].

Mass Spectrometric Data Analysis

To distinguish enzymatic methylation from non-enzymatic methylation, translational errors, and spurious methylation in bacteria, in vitro methylation reactions using either [$^{12}$CH3]-SAM (SAM), [$^{13}$CD3]-SAM (hSAM) or a 1:1 mixture of both as substrates were performed. This results in a mass shift of +14 amu (atomic mass units) and +18amu respectively. All non-enzymatic methylations, translational errors or methylations that occurred before the incubation with C21orf127/TRMT112 with H4 would only show a mass shift of +14amu and were therefore excluded from further analysis. SAM and hSAM were synthesized from ATP and methionine or [$^{13}$CD3]methionine using bacterially expressed S-adenosylmethionine synthetase (Sam-S) from *D. melanogaster*[33].

To identify the site methylated by KMT9 in histone H4, 1 µg of H4 was incubated with purified KMT9 and SAM, digested for 12 hrs using Arg-C and acidified using 10% TFA. The acidified peptide mixture was then 1:10 diluted in 0.1% FA and analysed using an Ultimate 3000 NCS HPLC system coupled to a QExactive HF mass spectrometer. For peptide separation, the samples were loaded onto a nano-RP C18 separation column (120×0.075 mm, ReproSil Pur-C18 AQ, 2.4 µm, in house packed) at a flow rate of 300 nl/min using a buffer composition of 96% A (0.1% FA in water) and 4% B (80% ACN, 0.1% FA in water). After a 5 min loading phase at 4% B, a linear gradient to 50% B was applied over 50 min followed by a high organic wash of the column at 90% B for 5 min, and column reconditioning to 4% B. For the measurement of in vivo methylation (FIG. 2e and Extended FIG. 2e-i) a longer gradient (130 min) was used. The mass spectrometer was operated in data-dependent acquisition (DDA) mode throughout the complete elution period to detect peptides and perform fragmentation of suitable candidates. The MS acquisition program consisted of one survey scan with a resolution of 60,000 at 200 m/z and up to 10 MS/MS spectra with a resolution of 15,000. Suitable precursor ions had a confirmed charge state of 2-5 and a minimal intensity of 50,000 AU. Other signals were excluded from MS/MS acquisition. Dynamic precursor exclusion was enabled for 15 sec to prevent repeated selection of intense precursor signals.

To identify methylation sites within H4, m/z values for unmodified, light, and heavy methylated oligopeptides created by Arg-C mediated cleavage were calculated and manually inspected using the XCalibur QualBrowser software with a maximal precursor mass deviation of 6 ppm. For in vivo detection of H4K12me1 in PC-3M cells histones were separated by SDS-PAGE, stained by Coomassie blue and histone H4 was excised from the gel. Gel pieces were destained, treated with propionic anhydride to protect lysines (unmodified and monomethylated) from tryptic cleavage and subjected to tryptic digestion. Tryptic peptides were purified using C18 stage tips and analysed by LC-MS/MS using either data-dependent acquisition (DDA) or a targeted parallel precursor reaction monitoring (PRM) acquisition mode of selected histone peptides to specifically quantify differentially methylated peptides ions. PRM analysis was programmed for several expected modifications of histone H4 peptides aa4-17, aa24-35, and aa79-92 in 2+ charge state (for more informations see Supplementary Table S1). Identification and quantitation of the data were performed manually based on the unprocessed MS data. Localization of methylation sites was manually curated by comparing the presence of fragment ion signals to a list of theoretical fragment ions generated with the GPMAW software. Due to coelution of the peptide containing H4K8 monomethylation and H4K12 monomethylation, PRM quantitation was performed on fragment ions y6 to y9 to omit interference by overlapping spectral information. The mass spectrometry proteomics data have been deposited to the ProteomeXchange Consortium via the PRIDE partner repository with the dataset identifier PXD008965. PRM data have been deposited to PASSEL (peptide Atlas platform) with the dataset identifier PASS01154.

Stable Isotope Labelling of Cells

HEK 293 cells with genetic deletion of KMT9α (HEK 293 KMT9α$^{-/-}$) were generated as previously described[34,35]. Wild type HEK 293 cells and HEK 293 KMT9α$^{-/-}$ were first grown in normal medium for six passages followed by growth in SILAC medium containing either light ([$^{12}$CH$_3$]-methionine) and heavy methionine ([$^{13}$CD$_3$]-methionine) as described[24]. Histones of each mixture were extracted and prepared as previously described[36].

Cluster Analysis

The phylogenetic tree resulting from multiple sequence alignment of the methyltransferases domains of C21orf127, TRMT12, TRMT5, KIAA1456, WBSCR22, METTL27, DOT1L, and TRMT11 was generated by ClustalO in Jalview using PAM250. For the analysis, the amino acid sequences corresponding to C21orf127 aa1-214, TRMT12 aa100-448, TRMT5 aa121-509, KIAA1456 aa1-350, WBSCR22 aa1-298, METTL27 aa1-245, DOT1L aa1-350, and TRMT11 aa96-463 were used.

Isothermal Titration Calorimetry (ITC)

ITC experiments were performed at 20° C. with a MicroCal VP-ITC microcalorimeter (Malvern). Experiments were performed by injecting 200 μM SAM (#9003S, NEB) into the sample cell containing 20 μM C21orf127/TRMT112 (KMT9α/KMT9β), C21orf127(N122A)/TRMT112 (KMT9α(N122A)/KMT9β), C21orf127(Y125A)/TRMT112 (KMT9α(Y125A)/KMT9β), C21orf127 (KMT9α) or TRMT112 (KMT9B) in 25 mM HEPES pH 7.5, 100 mM NaCl, 2 mM beta-mercaptoethanol. ITC data were analysed and fitted with one-site binding model by using Origin 7.0.

Crystallization, Data Collection, and Structure Determination

To obtain the co-crystals of C21orf127/TRMT112-SAH, C21orf127/TRMT112 was mixed with SAH and grown in 100 mM HEPES at 20° C. Crystals appeared after one day and reached their full size within one week. Prior to flash freezing by liquid nitrogen, crystals were cryoprotected. The data was collected at the Swiss Light Source beam line PX3 using a wavelength of 1.0000 Å. Data were processed and analysed with iMosflm[37] and Aimless[38]. The crystal belongs to the space group P42212 and contains one copy of C21orf127/TRMT112 in one asymmetric unit. The structure was solved by molecular replacement with Phaser[39] using Mtq2 (PDB 3Q87) and Trm112 (PDB 4QTU) as a search model. Manual building and refinement were performed using Coot[40] and Phenix.refine[41] in the Phenix package[42]. The co-crystals with the H4aa1-21 K12me1 (SGRGKGGKGLGKmeGGAKRHRKV) peptide was obtained by soaking the C21orf127/TRMT112-SAH crystal in the reservoir condition with H4K12me1 peptide overnight before collecting. The data were collected in the beamline PX3 of Swiss Light Source using a wavelength of 1.0000 Å. The structure was solved by molecular replacement using the apo-form of C21orf127/TRMT112 model as a search model. The structure was further refined using Phenix.refine and manual rebuilding in COOT. The final models were validated by MolProbity[43] in the Phenix package and RCSB Validation server. Table 1 summarizes the statistics for data collection and refinement. Crystallographic data have been deposited in the Protein Data Bank under the accession codes 6H1D and 6H1E.

Gel Filtration Chromatography

The analysis of C21orf127/TRMT112 (KMT9α(KMT90) and C21orf127(N122A)/TRMT112 (KMT9α(N122A)/KMT90) heterodimers by gel filtration chromatography was carried out with a Superose 6 10/300 GL column (GE Healthcare). For the analysis, a total of 200 μg protein in 100 μl running buffer (20 mM Tris HCl pH 8.0, 100 mM NaCl, 2 mM DTT, 5% glycerol) was injected.

RNA Preparation and Analysis

Cells were cultured in the presence siCtrl or siKMT9α for 72 hours. RNA was isolated as previously described31. Quantitative RT-PCR was performed using the Abgene SYBR Green PCR kit (Invitrogen) according to the supplier's protocol. MTA1 was used for normalization. Primers for BIRC5, CDK1, ODF2, OSGIN2, PGHDH, RTKN2, STIL, VRK1, and MTA1 were as follows:

```
BIRC5:
                                      [SEQ ID NO: 12]
  5'-GGACCACCGCATCTCTACAT-3',

[SEQ ID NO: 13]
  5'-GAAACACTGGGCCAAGTCTG-3';

CDK1:
                                      [SEQ ID NO: 14]
  5'-TACAGGTCAAGTGGTAGCCA-3',

[SEQ ID NO: 15]
  5'-AGCACATCCTGAAGACTGACT-3';

ODF2:
                                      [SEQ ID NO: 16]
  5'-GATGAGAACACCCCTGTCCA-3',

[SEQ ID NO: 17]
  5'-CGGGCAGATGATTTTCCAGG-3';

OSGIN2:
                                      [SEQ ID NO: 18]
  5'-TCCAGTTGCAGTACTTTTCGA-3',

[SEQ ID NO: 19]
  5'-TATTATGCCAAGCCCCACCA-3';

PGHDH:
                                      [SEQ ID NO: 20]
  5'-CTGCCGGAAGATCTTGCAAG-3',

[SEQ ID NO: 21]
  5'-TCCACATTGTCCACACCTGT-3';

RTKN2:
                                      [SEQ ID NO: 22]
  5'-TTGCTAGCTCACACTACCCT-3',

[SEQ ID NO: 23]
  5'-GCATCCTCAGCCATACAAGC-3';

STIL:
                                      [SEQ ID NO: 24]
  5'-AATGTGCACTTTGGAACCCA-3',
```

```
                                            [SEQ ID NO: 25]
5'-AGCAAGTCGGATGGTCTTCT-3';

VRK1:
                                            [SEQ ID NO: 26]
5'-TCAGAGTCAGTTGGCAGTGA-3',

[SEQ ID NO: 27]
5'-GGTTTTGCAGCTCGTTGGTA-3';

MTA1:
                                            [SEQ ID NO: 28]
5'-CGAGTCGCTCAAGTCCTACC-3',

[SEQ ID NO: 29]
5'-TGGTACCGGTTTCCTACTCG-3'
```

Immunohistochemical Staining (IHC)

To assess KMT9α and H4K12me1 levels in human prostate tissues, 25 benign prostate samples, 305 radical prostatectomy specimens, 81 locally advanced/recurrent prostate tumour specimens, 31 lymph node metastasis specimens, and 104 distant metastasis specimens from patients who underwent surgery at Goppingen Medical Center, Germany between 2002 and 2014 were stained by immunohistochemistry. Tissue microarrays (TMA) from formalin-fixed, paraffin-embedded prostate tissues were constructed representing a triplicate of 0.6 mm core biopsy of each samples. Immunohistochemical staining on human prostate and colrectal cancer samples was performed using the Ventana Discovery automated staining system (Ventana Medical System) according to manufacturer's protocol. Samples were incubated at room temperature with primary antibodies: anti-H4K12me1 (#27429, lot 27062017, Schule Lab, 1:200 dilution) or (anti-KMT9α, #27630, lot 20062017, Schüle Lab; 1:160 dilution). To demonstrate specificity, control samples were pre-incubated with KMT9α or H4K12me1-specific blocking peptides for 15 minutes at room temperature prior to incubation with primary antibody. Primary antibodies were detected using the ultraView Universal DAB Detection Kit (Ventana Medical System). Stained slides were scanned (Panoramic Desk, 3DHistech) and evaluation of staining intensity was performed independently by two pathologists.

Flow Cytometry for Detection of Apoptosis and Cell Cycle

For apoptosis analysis cells were harvested by trypsinization four days after treatment with siRNA and stained with AnnexinV-APC in binding buffer together with propidium iodide (PI) for 30 min at room temperature according to manufacturer's protocol (Biolegend, Apoptosis Detection Kit). Cells positive for AnnexinV alone and double positive for AnnexinV and PI were considered apoptotic. Cell cycle phase distribution was measured via DNA staining by PI. To this end, trypsinized cells were fixed in ice-cold 70% ethanol and kept at −20° C. for at least 2 h prior to 2 wash steps in PBS. Staining was performed with 100 µg/ml RNaseA and 50 µg/ml PI for 30 min at room temperature. Subsequently, cells analysed by recording at least 10,000 events gated in PI-Area versus PI-Width channels. Cell cycle phase proportions were calculated by FlowJo software. Flow cytometry was done using BD LSR-Fortessa Cell Analyzer and data were analysed with FlowJo software.

Data Analysis

Data are represented as mean+standard error of the mean (s.e.m.) or mean+standard deviation (s.d.). Significance was calculated by a two-tailed Student's t test.

REFERENCES

1 Strahl, B. D. & Allis, C. D. The language of covalent histone modifications. *Nature* 403, 41-45, doi:10.1038/47412 (2000).

2 Dillon, S. C., Zhang, X., Trievel, R. C. & Cheng, X. The SET-domain protein superfamily: protein lysine methyltransferases. *Genome Biol* 6, 227, doi:10.1186/gb-2005-6-8-227 (2005).

3 Arrowsmith, C. H., Bountra, C., Fish, P. V., Lee, K. & Schapira, M. Epigenetic protein families: a new frontier for drug discovery. *Nat Rev Drug Discov* 11, 384-400, doi:10.1038/nrd3674 (2012).

4 van Leeuwen, F., Gafken, P. R. & Gottschling, D. E. Dot1p modulates silencing in yeast by methylation of the nucleosome core. *Cell* 109, 745-756 (2002).

5 Petrossian, T. C. & Clarke, S. G. Uncovering the human methyltransferasome. *Mol Cell Proteomics* 10, M110 000976, doi:10.1074/mcp.M110.000976 (2011).

6 Le Guen, L., Santos, R. & Camadro, J. M. Functional analysis of the hemK gene product involvement in protoporphyrinogen oxidase activity in yeast. *FEMS Microbiol Lett* 173, 175-182 (1999).

7 Cheng, X. Structure and function of DNA methyltransferases. *Annu Rev Biophys Biomol Struct* 24, 293-318, doi:10.1146/annurev.bb.24.060195.001453 (1995).

8 Yang, Z. et al. Structural characterization and comparative phylogenetic analysis of *Escherichia coli* HemK, a protein (N5)-glutamine methyltransferase. *J Mol Biol* 340, 695-706, doi:10.1016/j.jmb.2004.05.019 (2004).

9 Ratel, D. et al. Undetectable levels of N6-methyl adenine in mouse DNA: Cloning and analysis of PRED28, a gene coding for a putative mammalian DNA adenine methyltransferase. *FEBS Lett* 580, 3179-3184, doi:10.1016/j.febslet.2006.04.074 (2006).

10 Xiao, C. L. et al. N(6)-Methyladenine DNA Modification in the Human Genome. *Mol Cell*, doi:10.1016/j.molcel.2018.06.015 (2018).

11 Schiffers, S. et al. Quantitative LC-MS Provides No Evidence for m(6) dA or m(4) dC in the Genome of Mouse Embryonic Stem Cells and Tissues. *Angew Chem int Ed Engl* 56, 11268-11271, doi:10.1002/anie.201700424 (2017).

12 Liu, P. et al. Deficiency in a glutamine-specific methyltransferase for release factor causes mouse embryonic lethality. *Mol Cell Biol* 30, 4245-4253, doi:10.1128/MCB.00218-10 (2010).

13 Heurgue-Hamard, V. et al. The zinc finger protein Ynr046w is plurifunctional and a component of the eRF1 methyltransferase in yeast. *J Biol Chem* 281, 36140-36148, doi:10.1074/jbc.M608571200 (2006).

14 Figaro, S., Scrima, N., Buckingham, R. H. & Heurgue-Hamard, V. HemK2 protein, encoded on human chromosome 21, methylates translation termination factor eRF1. *FEBS Lett* 582, 2352-2356, doi:10.1016/j.febslet.2008.05.045 (2008).

15 Zorbas, C. et al. The human 18S rRNA base methyltransferases DIMT1L and WBSCR22-TRMT112 but not rRNA modification are required for ribosome biogenesis. *Mol Biol Cell* 26, 2080-2095, doi:10.1091/mbc.E15-02-0073 (2015).

16 Cai, X. C., Kapilashrami, K. & Luo, M. Synthesis and Assays of Inhibitors of Methyltransferases. *Methods Enzymol* 574, 245-308, doi:10.1016/bs.mie.2016.01.009 (2016).

17 Schubert, H. L., Blumenthal, R. M. & Cheng, X. Many paths to methyltransfer: a chronicle of convergence. *Trends Biochem Sci* 28, 329-335, doi:10.1016/S0968-0004(03)00090-2 (2003).

18 Liger, D. et al. Mechanism of activation of methyltransferases involved in translation by the Trm112 'hub' protein. *Nucleic Acids Res* 39, 6249-6259, doi:10.1093/nar/gkr176 (2011).
19 Schubert, H. L., Phillips, J. D. & Hill, C. P. Structures along the catalytic pathway of PrmC/HemK, an N5-glutamine AdoMet-dependent methyltransferase. *Biochemistry* 42, 5592-5599, doi:10.1021/bi034026p (2003).
20 Kusevic, D., Kudithipudi, S. & Jeltsch, A. Substrate Specificity of the HEMK2 Protein Glutamine Methyltransferase and Identification of Novel Substrates. *J Biol Chem* 291, 6124-6133, doi:10.1074/jbc.M115.711952 (2016).
21 Nadal, R. & Bellmunt, J. The evolving role of enzalutamide on the treatment of prostate cancer. *Future Oncol* 12, 607-616, doi:10.2217/fon.15.351 (2016).
22 Leroy, G. et al. A quantitative atlas of histone modification signatures from human cancer cells. *Epigenetics Chromatin* 6, 20, doi:10.1186/1756-8935-6-20 (2013).
23 Feller, C., Forne, I., Imhof, A. & Becker, P. B. Global and specific responses of the histone acetylome to systematic perturbation. *Mol Cell* 57, 559-571, doi:10.1016/j.molcel.2014.12.008 (2015).
24 Ong, S. E., Mittler, G. & Mann, M. Identifying and quantifying in vivo methylation sites by heavy methyl SILAC. *Nat Methods* 1, 119-126, doi:10.1038/nmeth715 (2004).
25 Hoefer, J. et al. Critical role of androgen receptor level in prostate cancer cell resistance to new generation antiandrogen enzalutamide. *Oncotarget* 7, 59781-59794, doi: 10.18632/oncotarget.10926 (2016).
26 Metzger, E. et al. LSD1 demethylates repressive histone marks to promote androgen-receptor-dependent transcription. *Nature* 437, 436-439, doi:10.1038/nature04020 (2005).
27 Dobin, A. et al. STAR: ultrafast universal RNA-seq aligner. *Bioinformatics* 29, 15-21, doi:10.1093/bioinformatics/bts635 (2013).
28 Zhang, Y. et al. Model-based analysis of ChIP-Seq (MACS). *Genome biology* 9, R137, doi:10.1186/gb-2008-9-9-r137 (2008).
29 Thorvaldsdottir, H., Robinson, J. T. & Mesirov, J. P. Integrative Genomics Viewer (IGV): high-performance genomics data visualization and exploration. *Brief Bioinform* 14, 178-192, doi:10.1093/bib/bbs017 (2013).
30 Heinz, S. et al. Simple combinations of lineage-determining transcription factors prime cis-regulatory elements required for macrophage and B cell identities. *Molecular cell* 38, 576-589, doi:10.1016/j.molcel.2010.05.004 (2010).
31 Metzger, E. et al. Assembly of methylated KDM1A and CHD1 drives androgen receptor-dependent transcription and translocation. *Nature structural & molecular biology* 23, 132-139, doi:10.1038/nsmb.3153 (2016).
32 Robinson, M. D. & Smyth, G. K. Small-sample estimation of negative binomial dispersion, with applications to SAGE data. *Biostatistics* 9, 321-332, doi:10.1093/biostatistics/kxm030 (2008).
33 Gross, A., Geresh, S. & Whitesides, G. M. Enzymatic synthesis of S-adenosyl-L-methionine from L-methionine and ATP. *Appl Biochem Biotechnol* 8, 415-422 (1983).
34 Schmid-Burgk, J. L. et al. OutKnocker: a web tool for rapid and simple genotyping of designer nuclease edited cell lines. *Genome Res* 24, 1719-1723, doi:10.1101/gr.176701.114 (2014).
35 Schmidt, T., Schmid-Burgk, J. L. & Hornung, V. Synthesis of an arrayed sgRNA library targeting the human genome. *Sci Rep* 5, 14987, doi:10.1038/srep14987 (2015).
36 Alabert, C. et al. Two distinct modes for propagation of histone PTMs across the cell cycle. *Genes Dev* 29, 585-590, doi:10.1101/gad.256354.114 (2015).
37 Battye, T. G., Kontogiannis, L., Johnson, O., Powell, H. R. & Leslie, A. G. iMOSFLM: a new graphical interface for diffraction-image processing with MOSFLM. *Acta Crystallogr D Biol Crystallogr* 67, 271-281, doi:10.1107/S0907444910048675 (2011).
38 Evans, P. R. & Murshudov, G. N. How good are my data and what is the resolution? *Acta Crystallogr D Biol Crystallogr* 69, 1204-1214, doi:10.1107/S0907444913000061 (2013).
39 McCoy, A. J. et al. Phaser crystallographic software. *J Appl Crystallogr* 40, 658-674, doi:10.1107/S0021889807021206 (2007).
40 Emsley, P., Lohkamp, B., Scott, W. G. & Cowtan, K. Features and development of Coot. *Acta Crystallogr D Biol Crystallogr* 66, 486-501, doi:10.1107/S0907444910007493 (2010).
41 Afonine, P. V. et al. Towards automated crystallographic structure refinement with phenix.refine. *Acta Crystallogr D Biol Crystallogr* 68, 352-367, doi:10.1107/S0907444912001308 (2012).
42 Adams, P. D. et al. PHENIX: a comprehensive Python-based system for macromolecular structure solution. *Acta Crystallogr D Biol Crystallogr* 66, 213-221, doi:10.1107/S0907444909052925 (2010).
43 Chen, V. B. et al. MolProbity: all-atom structure validation for macromolecular crystallography. Acta Crystallogr D Biol Crystallogr 66, 12-21, doi:10.1107/S0907444909042073 (2010).

The invention claimed is:

1. A method for treating cancer in a subject, wherein said method comprises administering a KMT9-inhibitor to the subject, wherein said KMT9-inhibitor is a selective KMT9-inhibitor, wherein said KMT9-inhibitor is a small molecule selective for KMT9-inhibition, and wherein the small molecule selective for KMT9-inhibition has the following structure:

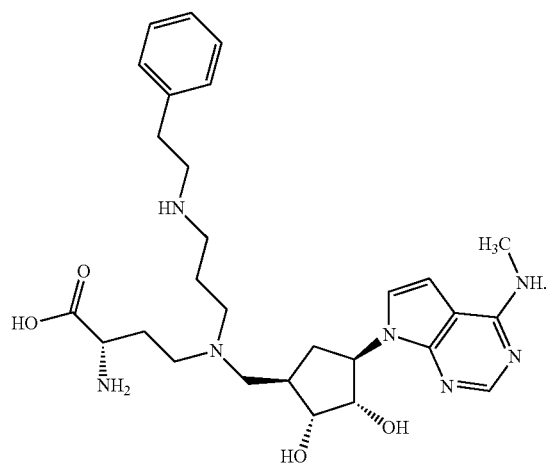 [SMILES: CNc1ncnc2c1ccn2[C@@H]1C[C@H](CN(CCCNCCc2ccccc2)CC[C@H](N)C(=O)O)[C@@H](O)[C@H]1O]

2. A method for treating cancer in a subject, wherein said method comprises administering a KMT9-inhibitor to the subject, wherein said KMT9-inhibitor is a selective KMT9-inhibitor, wherein said KMT9-inhibitor is a small molecule selective for KMT9-inhibition, and wherein the small molecule selective for KMT9-inhibition has the following structure:

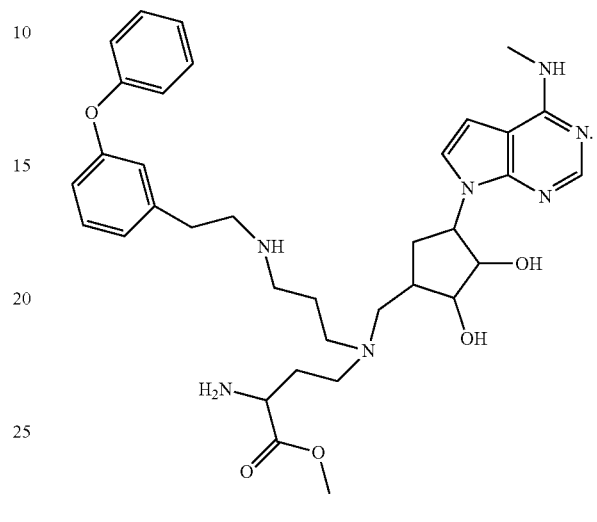

* * * * *